(12) United States Patent
Bunnelle et al.

(10) Patent No.: US 7,265,115 B2
(45) Date of Patent: Sep. 4, 2007

(54) DIAZABICYCLIC CNS ACTIVE AGENTS

(75) Inventors: William H. Bunnelle, Mundelein, IL (US); Daniela Barlocco Cristina, Milan (IT); Jerome F. Daanen, Racine, WI (US); Michael J. Dart, Highland Park, IL (US); Michael D. Meyer, Lake Villa, IL (US); Keith B. Ryther, Round Lake Park, IL (US); Michael R. Schrimpf, Grayslake, IL (US); Kevin B. Sippy, Antioch, IL (US); Richard B. Toupence, Chicago, IL (US)

(73) Assignee: Abbott Laboratories, Abbott Park, IL (US)

(*) Notice: Subject to any disclaimer, the term of this patent is extended or adjusted under 35 U.S.C. 154(b) by 823 days.

(21) Appl. No.: 10/412,510

(22) Filed: Apr. 11, 2003

(65) Prior Publication Data

US 2003/0225268 A1 Dec. 4, 2003

Related U.S. Application Data

(63) Continuation of application No. 09/466,719, filed on Dec. 17, 1999, now abandoned.

(60) Provisional application No. 60/117,807, filed on Jan. 29, 1999.

(51) Int. Cl.
  *A61P 25/00* (2006.01)
  *A61K 31/47* (2006.01)
  *A61K 31/44* (2006.01)
  *A61K 31/42* (2006.01)
  *C07D 239/00* (2006.01)

(52) U.S. Cl. ............ 514/248; 514/252.06; 514/255.05; 514/256; 514/274; 514/275; 514/301; 514/302; 514/312; 514/313; 514/314; 514/338; 514/372; 514/378; 514/380; 544/237; 544/238; 544/242; 544/315; 544/330; 544/332; 544/334; 544/335; 544/336; 544/406; 544/407; 544/408; 544/409; 544/410; 546/114; 546/115; 546/152; 546/168; 546/169; 546/170; 546/171; 546/172; 546/174; 546/175; 546/176; 546/177; 546/178; 546/179; 546/180; 546/181; 546/276.7

(58) Field of Classification Search ............... 514/248, 514/252.06, 255.05, 256, 274, 275, 301, 514/302, 312, 313, 314, 338, 372, 378, 380; 544/237, 238, 242, 315, 330, 332, 334, 335, 544/336, 406, 407, 408, 409, 410; 546/114, 546/115, 152, 168, 169, 170, 171, 172, 174, 546/175, 176, 177, 178, 179, 180, 181, 276.7; 548/206, 213, 214, 243, 245, 247, 248

See application file for complete search history.

(56) References Cited

U.S. PATENT DOCUMENTS 5,382,584 A 1/1995 Balasubramanian ........ 514/252
5,478,939 A 12/1995 Trybulski et al. ........... 544/336
5,652,258 A 7/1997 Phillips et al. .............. 514/400
6,440,970 B1* 8/2002 Clark et al. ................. 514/249
6,635,645 B1* 10/2003 Lochead et al. ........ 514/252.01

FOREIGN PATENT DOCUMENTS

| EP | 0324543 | 7/1989 |
|---|---|---|
| EP | 0345808 | 12/1989 |
| EP | 0400661 | 12/1990 |
| FR | 2531709 | 2/1984 |
| WO | 9523152 | 8/1995 |
| WO | 9717961 | 5/1997 |
| WO | 9726258 | 7/1997 |
| WO | 9854182 | 12/1998 |
| WO | 9854181 | 12/1999 |
| WO | 0034284 | 6/2000 |

OTHER PUBLICATIONS

Arneric, S. P., et al., "Cholinergic channel modulators as a novel therapeutic strategy for Alzheimer's disease", *Exp. Opin. Invest. Drugs*, 5(1):79-100 (1996).

Arneric, S. P., et al., "Neuronal Nicotinic Acetylcholine Receptors Novel Targets for Central Nervous System Therapeutics", *Psychopharmacology: The Fourth Generation of Progress*, 95-109 (1995).

Bambas, L. L., "Some Chemotherapeutically Active Sulfones", 67:668-670, 1945.

Barlocco, D., et al., "Mono- and Disubstituted-3,8-diazabicyclo[3.2.1]octane Derivatives as Analgesics Structurally Related to Epibatidine: Synthesis, Activity, and Modeling", *J. Med. Chem.*, 41:674-681 (1998).

Bouzard, D., et al., "Fluoronaphthyridines and Quinolones as Antibacterial Agents. 2. Synthesis and Structure-Activity Relationships of New 1-*tert*-Butyl 7-Substituted Derivatives", *J. Med. Chem.*, 32:1344-1352 (1990).

Ghelardini, C., et al., "Antinociceptive Profile of the New Nicotinic Agonist DBO-83", *Drug Development Research*, 40:251-258 (1997).

Hoffman, B. B., et al., "The Autonomic and Somatic Motor Nervous Systems", Chapter 6-Neurotransmission 105-139, 1996.

(Continued)

*Primary Examiner*—Brenda Coleman
(74) *Attorney, Agent, or Firm*—Gabyrleda Ferrari Dileo

(57) ABSTRACT

Compounds of formula I:

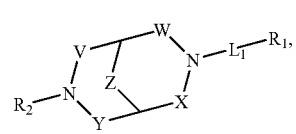

or pharmaceutically acceptable salts thereof, are useful for controlling synaptic transmission in mammals.

14 Claims, No Drawings

OTHER PUBLICATIONS

Korczyn, A. D., Parkinson's Disease, *Psychopharmacology: The Fourth Generation of Progress*, 1479-1484 (1995).

Lindstrom, J., "N icotinic Acetylcholine Receptors in Health and Disease", *Molecular Neurobiology*, 15:193-222 (1997).

Lloyd, G. K.,et al., "The Potential of Subtype-Selective Neuronal Nicotinic Acetycholine Receptor Agonists as Therapeutic Agents", *Life Sciences*, 62(17/18): 1601-1606 (1998).

McGehee, D.S. et al., "Presynaptic ionotropic receptors," Current Opinion in Neurobiology 6:342-349 (1996).

Rosen, T., et al., "Design, Synthesis, and Properties of (4S)-7-(4-Amino-2-substituted-pyrrolidin-1-yl)quiknolone-3-carboxylic Acids", *J. Med. Chem.*, 1598-1611 (1988).

Roth, R. H., et al., "Biochemical Pharmacology of Midbrain Dopamine Neurons", *Psychopharmacology: the Fourth Generation of Progress*, 227-242 (1995).

Salin-Pascual, R. J., et al., "Antidepressant Effect of Transdermal Nicotine Patches in Nonsmoking Patients with Major Depression", *J. Clin. Psyciatry*, 57(9(:387-389 (1996).

Wagaw, S., et al., "The Synthesis of Aminopyridines: A Method Employing Palladium-Catalyzed Carbon-Nitrogen Bond Formation", *J. Org. Chem.*, 61:7240-7241 (1996).

Williams, M., et al., "Beyond the tobacco debate: dissecting out the therapeutic potential of nicotine", *Exp. Opin. Invest. Drugs*, 5(8):1035-1045 (1995).

Wittenberger, S. J., et al., "Dialkyltin Oxide Mediated Addition of Trimethylsilyl Azide to Nitriles. A Novel Preparation of 5-Substituted Tetrazoles", *J. Org. Chem.*, 58:4139-4141 (1993).

Wonnacott, S., "Presynaptic nicotinic Ach receptors," TINS 20(2):92-98 (1997).

\* cited by examiner

DIAZABICYCLIC CNS ACTIVE AGENTS

REFERENCE TO RELATED APPLICATION

This application is a continuation of U.S. patent application Ser. No. 09/466,719 filed on Dec. 17, 1999, now abandoned which claims the benefit of U.S. Provisional Application No. 60/117,807 filed Jan. 29, 1999.

FIELD OF THE INVENTION

The present invention is directed to a series of N-substituted diazabicyclic compounds, methods for selectively controlling neurotransmitter release in mammals using these compounds, and pharmaceutical compositions containing these compounds.

BACKGROUND OF THE INVENTION

Compounds that selectively control chemical synaptic transmission offer therapeutic utility in treating disorders that are associated with dysfunctions in synaptic transmission. This utility may arise from controlling either pre-synaptic or post-synaptic chemical transmission. The control of synaptic chemical transmission is, in turn, a direct result of a modulation of the excitability of the synaptic membrane. Presynaptic control of membrane excitability results from the direct effect an active compound has upon the organelles and enzymes present in the nerve terminal for synthesizing, storing, and releasing the neurotransmitter, as well as the process for active re-uptake. Postsynaptic control of membrane excitability results from the influence an active compound has upon the cytoplasmic organelles that respond to neurotransmitter action.

An explanation of the processes involved in chemical synaptic transmission will help to illustrate more fully the potential applications of the invention. (For a fuller explanation of chemical synaptic transmission refer to Hoffman et,al., "Neuro-transmission: The autonomic and somatic motor nervous systems." In: *Goodman and Gilman's, The Pharmacological Basis of Therapeutics*, 9th ed., J. G. Hardman, L. E. Limbird, P. B. Molinoff, R. W. Ruddon, and A. Goodman Gilman, eds., Pergamon Press, New York, (1996), pp. 105-139).

Typically, chemical synaptic transmission begins with a stimulus that depolarizes the transmembrane potential of the synaptic junction above the threshold that elicits an all- or -none action potential in a nerve axon. The action potential propagates to the nerve terminal where ion fluxes activate a mobilization process leading to neurotransmitter secretion and "transmission" to the postsynaptic cell. Those cells which receive communication from the central and peripheral nervous systems in the form of neurotransmitters are referred to as "excitable cells." Excitable cells are cells such as nerves, smooth muscle cells, cardiac cells and glands. The effect of a neurotransmitter upon an excitable cell may be to cause either an excitatory or an inhibitory postsynaptic potential (EPSP or IPSP, respectively) depending upon the nature of the postsynaptic receptor for the particular neurotransmitter and the extent to which other neurotransmitters are present. Whether a particular neurotransmitter causes excitation or inhibition depends principally on the ionic channels that are opened in the postsynaptic membrane (i.e., in the excitable cell).

EPSPs typically result from a local depolarization of the membrane due to a generalized increased permeability to cations (notably $Na^+$ and $K^+$), whereas IPSPs are the result of stabilization or hyperpolarization of the membrane excitability due to a increase in permeability to primarily smaller ions (including $K^+$ and $Cl^-$). For example, the neurotransmitter acetylcholine excites at skeletal muscle junctions by opening permeability channels for $Na^+$ and $K^+$. At other synapses, such as cardiac cells, acetylcholine can be inhibitory, primarily resulting from an increase in $K^+$ conductance.

The biological effects of the compounds of the present invention result from modulation of a particular subtype of acetylcholine receptor. It is, therefore, important to understand the differences between two receptor subtypes. The two distinct subfamilies of acetylcholine receptors are defined as nicotinic acetylcholine receptors and muscarinic acetylcholine receptors. (See *Goodman and Gilman's, The Pharmacological Basis of Therapeutics*, op. cit.).

The responses of these receptor subtypes are mediated by two entirely different classes of second messenger systems. When the nicotinic acetylcholine receptor is activated, the response is an increased flux of specific extracellular ions (e.g. $Na^+$, $K^+$ and $Ca^{++}$) through the neuronal membrane. In contrast, muscarinic acetylcholine receptor activation leads to changes in intracellular systems that contain complex molecules such as G-proteins and inositol phosphates. Thus, the biological consequences of nicotinic acetylcholine receptor activation are distinct from those of muscarinic receptor activation. In an analogous manner, inhibition of nicotinic acetylcholine receptors results in still other biological effects, which are distinct and different from those arising from muscarinic receptor inhibition As indicated above, the two principal sites to which drug compounds that affect chemical synaptic transmission may be directed are the presynaptic membrane and the postsynaptic membrane. Actions of drugs directed to the presynaptic site may be mediated through presynaptic receptors that respond to the neurotransmitter which the same secreting structure has released (i.e., through an autoreceptor), or through a presynaptic receptor that responds to another neurotransmitter (i.e., through a heteroreceptor). Actions of drugs directed to the postsynaptic membrane mimic the action of the endogenous neurotransmitter or inhibit the interaction of the endogenous neurotransmitter with a postsynaptic receptor.

Classic examples of drugs that modulate postsynaptic membrane excitability are the neuromuscular blocking agents which interact with nicotinic acetylcholine-gated channel receptors on skeletal muscle, for example, competitive (stabilizing) agents, such as curare, or depolarizing agents, such as succinylcholine.

In the central nervous system, postsynaptic cells can have many neurotransmitters impinging upon them. This makes it difficult to know the precise net balance of chemical synaptic transmission required to control a given cell. Nonetheless, by designing compounds that selectively affect only one pre- or postsynaptic receptor, it impossible to modulate the net balance of all the other inputs. Obviously, the more that is understood about chemical synaptic transmission in CNS disorders, the easier it would be to design drugs to treat such disorders.

Knowing how specific neurotransmitters act in the CNS allows one to predict the disorders that may be treatable with certain CNS-active drugs. For example, dopamine is widely recognized as an important neurotransmitter in the central nervous systems in humans and animals. Many aspects of the pharmacology of dopamine have been reviewed by Roth and Elsworth, "Biochemical Pharmacology of Midbrain Dopamine Neurons", In: *Psychopharmacology: The Fourth Generation of Progress*, F. E. Bloom and D. J. Kupfer, Eds., Raven Press, NY, 1995, pp 227-243). Patients with Parkinson's disease have a primary loss of dopamine containing neurons of the nigrostriatal pathway, which results in profound loss of motor control. Therapeutic strategies to replace the dopamine deficiency with dopamine mimetics, as well as administering pharmacologic agents that modify dopamine release and other neurotransmitters have been found to have therapeutic benefit ("Parkinson's Disease", In: *Psychopharmacology: The Fourth Generation of Progress*, op. cit., pp 1479-1484).

New and selective neurotransmitter controlling agents are still being sought, in the hope that one or more will be useful in important, but as yet poorly controlled, disease states or behavior models. For example, dementia, such as is seen with Alzheimer's disease or Parkinsonism, remains largely untreatable. Symptoms of chronic alcoholism and nicotine withdrawal involve aspects of the central nervous system, as does the behavioral disorder Attention-Deficit Disorder (ADD). Specific agents for treatment of these and related disorders are few in number or non-existent.

A more complete discussion of the possible utility as CNS-active agents of compounds with activity as cholinergic ligands selective for neuronal nicotinic receptors, (i.e., for controlling chemical synaptic transmission) may be found in U.S. Pat. No. 5,472,958, to Gunn et al., issued Dec. 5, 1995, which is incorporated herein by reference.

Existing acetylcholine agonists are therapeutically suboptimal in treating the conditions discussed above. For example, such compounds have unfavorable pharmacokinetics (e.g., arecoline and nicotine), poor potency and lack of selectivity (e.g., nicotine), poor CNS penetration (e.g., carbachol) or poor oral bioavailability (e.g., nicotine). In addition, other agents have many unwanted central agonist actions, including hypothermia, hypolocomotion and tremor and peripheral side effects, including miosis, lachrymation, defecation and tachycardia (Benowitz et al., in: Nicotine Psychopharmacology, S. Wonnacott, M. A. H. Russell, & I. P. Stolerman, eds., Oxford University Press, Oxford, 1990, pp. 112-157; and M. Davidson, et al., in Current Research in Alzheimer Therapy, E. Giacobini and R. Becker, ed.; Taylor & Francis: New York, 1988; pp 333-336).

Williams et al. reports the use of cholinergic channel modulators to treat Parkinson's and Alzheimer's Diseases. M. Williams et al., "Beyond the Tobacco Debate: Dissecting Out the Therapeutic Potential of Nicotine", Exp. Opin. Invest. Drugs 5, pp. 1035-1045 (1996). Salin-Pascual et al. reports short-term improvement of non-smoking patients suffering from depression by treatment with nicotine patches. R. J. Salin-Pascual et al., "Antidepressant Effect of Transdermal Nicotine Patches in Non-Smoking Patients with Major Depression", J. Clin. Psychiatry, v. 57 pp. 387-389 (1996).

Some diazabicyclo[2.2.1]heptane derivatives have been disclosed for various purposes. For example, N-heteroaromatic, N-alkylaryl substituted diazabicyclo[2.2.1]heptanes have been disclosed in European Patent Application No. 0 400 661 for the prevention of disorders resulting from brain and/or spinal cord anoxia; N-heteroaromatic, N-alkylaryl diazabicyclo[2.2.1]heptane derivatives have been disclosed in European Patent Application 0 324 543 as antiarrhythmic agents; N-heteroaromatic, -alkylaryl diazabicyclo[2.2.1]heptane derivatives have been disclosed in European Patent Publication No. 0 345 808 B 1 for the treatment of depression; N-alkylamidoheteroaromatic, N-alkylaromatic diazabicyclo[2.2.1]heptane derivatives have been disclosed in U.S. Pat. No. 5,382,584 for effective anti-ischemic protection for CNS and cardiac tissue, di-N-acylheteroaromatic diazabicyclo[2.2.1]heptane derivatives have been disclosed in PCT Publication No. WO97/17961 to stimulate hematopoiesis and for the treatment of viral, fungal and bacterial infectious diseases. Moreover NH or N-methyl N-heteroaromatic diazabicyclo[2.2.1]heptane derivatives for treating central cholinergic disfunction have been disclosed in U.S. Pat. No. 5,478,939. The heteroaromatic compounds can be halo-substituted pyrazines, thiazoles, thiadiazoles, thiophene or nitrobenzene, as disclosed in U.S. Pat. No. 5,478,939.

Substituted diazabicyclo[3.2.1]octane derivatives have also been disclosed for various uses. For example, NH or N-alkyl, N-2-pyrimidinyl diazabicyclo[3.2.1] octane derivatives for sedatives have been disclosed in French Publication 2 531 709; N-acyl, -acylheteroaromatic diazabicyclo[3.2.1] octane derivatives have been disclosed in PCT Publication No. WO 95/23152 for cental analgesic activity, 3-[6-Cl-pyridazin-3-yl]-diazabicyclo[3.2.1]octane having antinociceptive effect was disclosed in *Drug Development Research*, 40:251-258 (1997); and NH, N-halosubstituted heteroaromatic diazabicyclo[3.2.1]octane derivatives as analgesics were disclosed in J. Med. Chem, 1998, 41, 674-681. However, there is still a need for even more effective N-substituted diazabicyclic compounds.

It is therefore an object of this invention to provide novel N-substituted diazabicyclic compounds. It is a further object of this invention to provide such compounds which selectively control neurotransmitter release.

SUMMARY OF THE INVENTION

The present invention discloses N-substituted diazabicyclic compounds, a method for selectively controlling neurotransmitter release in mammals using these compounds, and pharmaceutical compositions including those compounds. More particularly, the present invention is directed to compounds of formula I:

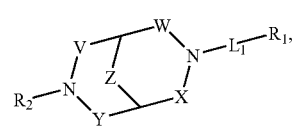

and their pharmaceutically acceptable salts wherein:

V is selected from the group consisting of a covalent bond and $CH_2$;

W is selected from the group consisting of a covalent bond, $CH_2$, and $CH_2CH_2$;

X is selected from the group consisting of a covalent bond and $CH_2$;

Y is selected from the group consisting of a covalent bond, $CH_2$, and $CH_2CH_2$;

Z is selected from the group consisting of $CH_2$, $CH_2CH_2$, and $CH_2CH_2CH_2$;

$L_1$ is selected from the group consisting of a covalent bond and $(CH_2)_n$;

n is 1-5;

$R_1$ is selected from the group consisting of

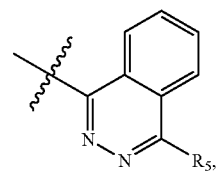 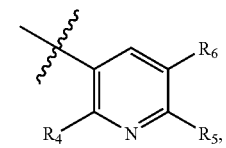

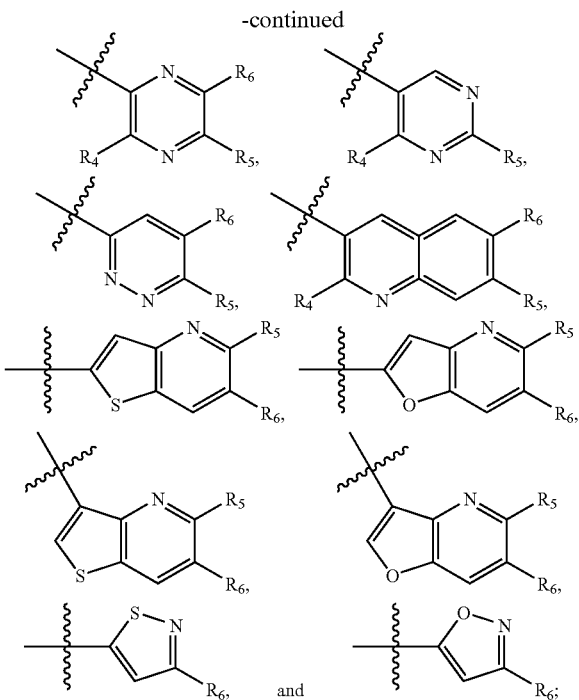

R$_2$ is selected from the group consisting of hydrogen, alkoxycarbonyl, alkyl, aminoalkyl, aminocarbonylalkyl, benzyloxycarbonyl, cyanoalkyl, dihydropyridin-3-ylcarbonyl, hydroxy, hydroxyalkyl, phenoxycarbonyl, and —NH$_2$;

R$_4$ is selected from the group consisting of hydrogen, alkyl, and halogen;

R$_5$ is selected from the group consisting of hydrogen, alkoxy, alkyl, halogen, nitro, and —NH$_2$;

R$_6$ is selected from the group consisting of hydrogen, alkenyl, alkoxy, alkoxyalkoxy, alkoxyalkyl, alkoxycarbonyl, alkoxycarbonylalkyl, alkyl, alkylcarbonyl, alkylcarbonyloxy, alkylthio, alkynyl, amino, aminoalkyl, aminocarbonyl, aminocarbonylalkyl, aminosulfonyl, carboxy, carboxyalkyl, cyano, cyanoalkyl, formyl, formylalkyl, haloalkoxy, haloalkyl, halogen, hydroxy, hydroxyalkyl, mercapto, mercaptoalkyl, nitro, 5-tetrazolyl, —NR$_7$SO$_2$R$_8$, —C(NR$_7$)NR$_7$R$_8$, —CH$_2$C(NR$_7$)NR$_7$R$_8$, —C(NOR$_7$)R$_8$, —C(NCN)R$_7$, —C(NNR$_7$R$_8$), —S(O)$_2$OR$_7$, and —S(O)$_2$R$_7$; and R$_7$ and R$_8$ are independently selected from the group consisting of hydrogen and alkyl;

with the proviso that the following compounds are excluded, 3-(6-chloro-3-pyridazinyl)-3,8-diazabicyclo [3.2.]octane;
3-(6-chloro-2-pyrazinyl)-3,8-diazabicyclo[3.2.1]octane;
8-(6-chloro-3-pyridazinyl)-3,8-diazabicyclo [3.2.1]octane; and
8-(6-chloro-2-pyrazinyl)-3,8-diazabicyclo[3.2.1]octane; and with the further proviso that when V and X are each a covalent bond; W, Y, and Z are each CH$_2$; and L$_1$ is a covalent bond; then R$_1$ is other than

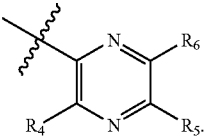

DETAILED DESCRIPTION OF THE INVENTION

In one embodiment of the present invention are disclosed compounds of formula II:

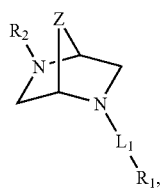

and their pharmaceutically acceptable salts wherein Z is selected from CH$_2$ and CH$_2$CH$_2$; and L$_1$, R$_1$, and R$_2$ are as defined in formula I.

Representative compounds of this embodiment include, but are not limited to:

(1S,4S)-2-(6-chloro-3-pyridazinyl)-2,5-diazabicyclo[2.2.1]heptane;
(1S,4S)-2-(6-chloro-5-methyl-3-pyridazinyl)-2,5-diazabicyclo[2.2.1]heptane;
(1S,4S)-2-(6-chloro-3-pyridazinyl)-5-methyl-2,5-diazabicyclo[2.2.1]heptane;
(1S,4S)-2-(6-chloro-5-methyl-3-pyridazinyl)-5-methyl-2,5-diazabicyclo[2.2.1]heptane;
(1S,4S)-2-(4-chloro-1-phthalazinyl)-2,5-diazabicyclo[2.2.1]heptane;
(1S,4S)-2-(4-chloro-1-phthalazinyl)-5-methyl-2,5-diazabicyclo[2.2.1]heptane;
(1S,4S)-2-(6-chloro-5-methoxycarbonyl-3-pyridazinyl)-2,5-diazabicyclo[2.2.1]heptane;
(1S,4S)-2-(3-pyridazinyl)-2,5-diazabicyclo [2.2.1]heptane;
(1S,4S)-2-(5-pyrimidinyl)-2,5-diazabicyclo [2.2.1]heptane;
(1S,4S)-2-(3-quinolinyl)-2,5-diazabicyclo[2.2.1]heptane;
(1S,4S)-2-(3-methyl-5-isothiazolyl)-2,5-diazabicyclo[2.2.1]heptane;
(1S,4S)-2-(6-chloro-3-pyridinyl)-2,5-diazabicyclo[2.2.1]heptane;
(1S,4S)-2-(6-amino-3-pyridinyl)-2,5-diazabicyclo [2.2.1]heptane;
(1S,4S)-2-(3-pyridinyl)-2,5-diazabicyclo[2.2.1]heptane;
(1S,4S)-2-[5-(benzyloxy)-3-pyridinyl]-2,5-diazabicyclo [2.2.1]heptane;
(1S,4S)-2-[5-hydroxy-3-pyridinyl]-2,5-diazabicyclo[2.2.1]heptane;
(1S,4S)-2-(6-methyl-3-pyridinyl)-2,5-diazabicyclo[2.2.1]heptane;
(1S,4S)-2-(6-nitro-3-pyridinyl)-2,5-diazabicyclo[2.2.1]heptane;
(1S,4S)-2-(6-fluoro-3-pyridinyl)-2,5-diazabicyclo[2.2.1]heptane;
(1S,4S)-2-(5-bromo-3-pyridinyl)-2,5-diazabicyclo[2.2.1]heptane;
(1S,4S)-2-(5-cyano-3-pyridinyl)-2,5-diazabicyclo[2.2.1]heptane;
(1S,4S)-2-(5-aminomethyl-3-pyridinyl)-2,5-diazabicyclo [2.2.1]heptane;
(1S,4S)-2-(5-aminocarbonyl-3-pyridinyl)-2,5-diazabicyclo [2.2.1]heptane;
(1S,4S)-2-(5-methoxy-3-pyridinyl)-2,5-diazabicyclo[2.2.1]heptane;
(1S,4S)-2-(6-chloro-5-hydroxy-3-pyridinyl)-2,5-diazabicyclo[2.2.1]heptane;

The following additional compounds, representative of formula II, may be prepared by one skilled in the art using known synthetic chemistry methodology or by using synthetic chemistry methodology described in the Schemes and Examples contained herein.

(1S,4S)-2-(thieno[3,2-b]pyridin-2-yl)-2,5-diazabicyclo[2.2.1]heptane;
(1S,4S)-2-(furo[3,2-b]pyridin-2-yl)-2,5-diazabicyclo[2.2.1]heptane;
(1S,4S)-2-(6-chloro-3-pyridinyl)-5-cyanomethyl-2,5-diazabicyclo[2.2.1]heptane;
(1S,4S)-2-(6-methoxy-3-pyridinyl)-2,5-diazabicyclo[2.2.1]heptane;
(1S,4S)-2-(6-chloro-5-methoxy-3-pyridinyl)-2,5-diazabicyclo[2.2.1]heptane;
(1S,4S)-2-(6-chloro-5-methyl-3-pyridinyl)-2,5-diazabicyclo[2.2.1]heptane;
(1S,4S)-2-(5,6-dichloro-3-pyridinyl)-2,5diazabicyclo[2.2.1]heptane;
(1S,4S)-2-(6-chloro-5-ethynyl-3-pyridinyl)-2,5diazabicyclo[2.2.1]heptane;
(1S,4S)-2-(6-chloro-5-cyano-3-pyridinyl)-2,5diazabicyclo[2.2.1]heptane;
(1S,4S)-2-(5-methoxy-3-pyridinyl)-2,5diazabicyclo[2.2.1]heptane;
(1S,4S)-2-(6-fluoro-5-methyl-3-pyridinyl)-2,5diazabicyclo[2.2.1]heptane;
(1S,4S)-2-(5-ethynyl-6-fluoro-3-pyridinyl)-2,5diazabicyclo[2.2.1]heptane;
(1S,4S)-2-(5-cyano-6-fluoro-3-pyridinyl)-2,5diazabicyclo[2.2.1]heptane;
(1S,4S)-2-(5-bromo-6-chloro-3-pyridinyl)-2,5diazabicyclo[2.2.1]heptane;
(1S,4S)-2-(5-cyano-6-chloro-3-pyridinyl)-2,5diazabicyclo[2.2.1]heptane;
(1S,4S)-2-(5-hydroxymethyl-6-chloro-3-pyridinyl)-2,5-diazabicyclo[2.2.1]heptane;
(1S,4S)-2-(5-hydroxymethyl-6-fluoro-3-pyridinyl)-2,5-diazabicyclo[2.2.1]heptane;
(1S,4S)-2-(5-hydroxymethyl-3-pyridinyl)-2,5-diazabicyclo[2.2.1]heptane;
(1S,4S)-2-(5-aminomethyl-6-chloro-3-pyridinyl)-2,5-diazabicyclo[2.2.1]heptane;
(1S,4S)-2-(5-aminomethyl-6-fluoro-3-pyridinyl)-2,5-diazabicyclo[2.2.1]heptane;
(1S,4S)-2-(5-aminomethyl-3-pyridinyl)-2,5-diazabicyclo[2.2.1]heptane;
(1S,4S)-2-(5-carboxy-6-chloro-3-pyridinyl)-2,5-diazabicyclo[2.2.1]heptane;
(1S,4S)-2-(5-carboxy-6-fluoro-3-pyridinyl)-2,5-diazabicyclo[2.2.1]heptane;
(1S,4S)-2-(5-carboxy-3-pyridinyl)-2,5-diazabicyclo[2.2.1]heptane;
(1S,4S)-2-(5-aminocarbonyl-6-fluoro-3-pyridinyl)-2,5-diazabicyclo[2.2.1]heptane;
(1S,4S)-2-(5-aminocarbonyl-6-chloro-3-pyridinyl)-2,5-diazabicyclo[2.2.1]heptane;
(1S,4S)-2-(6-chloro-5-hydroxyiminomethyl-3-pyridinyl)-2,5-diazabicyclo[2.2.1]heptane;
(1S,4S)-2-(6-fluoro-5-hydroxyiminomethyl-3-pyridinyl)-2,5-diazabicyclo[2.2.1]heptane;
(1S,4S)-2-(5-hydroxyiminomethyl-3-pyridinyl)-2,5-diazabicyclo[2.2.1]heptane;
(1S,4S)-2-(2-fluoro-3-pyridinyl)-2,5-diazabicyclo[2.2.1]heptane;
(1S,4S)-2-(5-methyl-6-fluoro-3-pyridinyl)-2,5-diazabicyclo[2.2.1]heptane;
(1S,4S)-2-(5-aminosulfonyl-6-fluoro-3-pyridinyl)-2,5-diazabicyclo[2.2.1]heptane;
(1S,4S)-2-(5-aminosulfonyl-6-chloro-3-pyridinyl)-2,5-diazabicyclo[2.2.1]heptane;
(1S,4S)-2-(5-aminosulfonyl-3-pyridinyl)-2,5-diazabicyclo[2.2.1]heptane;
(1S,4S)-2-(6-chloro-5-methyl-3-pyridinyl)-2,5-diazabicyclo[2.2.2]octane;
(1S,4S)-2-(5,6-dichloro-3-pyridinyl)-2,5-diazabicyclo[2.2.2]octane;
(1S,4S)-2-(6-chloro-5-ethynyl-3-pyridinyl)-2,5-diazabicyclo[2.2.2]octane;
(1S,4S)-2-(6-chloro-5-cyano-3-pyridinyl)-2,5-diazabicyclo[2.2.2]octane;
(1S,4S)-2-(5-methoxy-3-pyridinyl)-2,5-diazabicyclo[2.2.2]octane;
(1S,4S)-2-(6-fluoro-5-methyl-3-pyridinyl)-2,5-diazabicyclo[2.2.2]octane;
(1S,4S)-2-(6-fluoro-3-pyridinyl)-2,5-diazabicyclo[2.2.2]octane;
(1S,4S)-2-(5-ethynyl-6-fluoro-3-pyridinyl)-2,5-diazabicyclo[2.2.2]octane;
(1S,4S)-2-(5-cyano-6-fluoro-3-pyridinyl)-2,5-diazabicyclo[2.2.2]octane;
(1S,4S)-2-(5-bromo-6-chloro-3-pyridinyl)-2,5-diazabicyclo[2.2.2]octane;
(1S,4S)-2-(3-pyridinyl)-2,5-diazabicyclo[2.2.2]octane; and
(1S,4S)-2-(6-chloro-3-pyridinyl)-2,5-diazabicyclo[2.2.2]octane.

In another embodiment of the present invention are disclosed compounds of formula III:

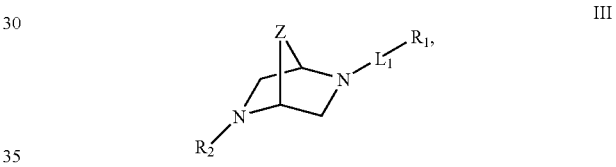

and their pharmaceutically acceptable salts wherein Z is selected from $CH_2$ and $CH_2CH_2$; and $L_1$, $R_1$, and $R_2$ are as defined in formula I.

Representative compounds of this embodiment include, but are not limited to:
(1R,4R)-2-(6-chloro-3-pyridazinyl)-2,5-diazabicyclo[2.2.1]heptane;
(1R,4R)-2-(3-pyridazinyl)-2,5-diazabicyclo[2.2.1]heptane;
2-(3-pyridinyl)-2,5-diazabicyclo[2.2.2]octane;
(1R,4R)-2-(5-cyano-3-pyridinyl)-2,5-diazabicyclo[2.2.1]heptane;
(1R,4R)-2-(thieno[3,2-b]pyridin-2-yl)-2,5-diazabicyclo[2.2.1]heptane;
(1R,4R)-2-(6-chloro-3-pyridinyl)-2,5-diazabicyclo[2.2.1]heptane;
(1R,4R)-2-(3-pyridinyl)-2,5-diazabicyclo[2.2.1]heptane;
(1R,4R)-2-(6-chloro-3-pyridinyl)-5-cyanomethyl-2,5-diazabicyclo[2.2.1]heptane;
(1R,4R)-2-(6-fluoro-3-pyridinyl)-2,5-diazabicyclo[2.2.1]heptane;
(1R,4R)-2-(5-hydroxy-3-pyridinyl)-2,5-diazabicyclo[2.2.1]heptane;
(1R,4R)-2-(6-chloro-5-hydroxy-3-pyridinyl)-2,5-diazabicyclo[2.2.1]heptane;
(1R,4R)-2-(5-cyano-3-pyridinyl)-2,5-diazabicyclo[2.2.1]heptane;
(1R,4R)-2-(6-methoxy-3-pyridinyl)-2,5-diazabicyclo[2.2.1]heptane;
(1R,4R)-2-(6-chloro-5-methyl-3-pyridinyl)-2,5-diazabicyclo[2.2.1]heptane;
(1R,4R)-2-(5,6-dichloro-3-pyridinyl)-2,5-diazabicyclo[2.2.1]heptane;

(1R,4R)-2-(5-aminocarbonyl-3-pyridinyl)-2,5-diazabicyclo [2.2.1]heptane;
(1R,4R)-2-(6-chloro-5-methoxy-3-pyridinyl)-2,5-diazabicyclo [2.2.1]heptane; and
(1R,4R)-2-(3-pyridinylmethyl)-2,5-diazabicyclo[2.2.1]heptane.

The following additional compounds, representative of formula III, may be prepared by one skilled in the art using known synthetic chemistry methodology or by using synthetic chemistry methodology described in the Schemes and Examples contained herein.

(1R,4R)-2-(furo[3,2-b]pyridin-2-yl)-2,5-diazabicyclo[2.2.1] heptane;
(1R,4R)-2-(6-chloro-5-methyl-3-pyridazinyl)-2,5-diazabicyclo[2.2.1]heptane;
(1R,4R)-2-(6-chloro-3-pyridazinyl)-5-methyl-2,5-diazabicyclo[2.2.1]heptane;
(1R,4R)-2-(6-chloro-5-methyl-3-pyridazinyl)-5-methyl-2,5-diazabicyclo [2.2.1]heptane;
(1R,4R)-2-(4-chloro-1-phthalazinyl)-2,5-diazabicyclo [2.2.1]heptane;
(1R,4R)-2-(4-chloro-1-phthalazinyl)-5-methyl-2,5-diazabicyclo[2.2.1]heptane;
(1R,4R)-2-(6-chloro-5-methoxycarbonyl-3-pyridazinyl)-2, 5-diazabicyclo[2.2.1]heptane;
(1R,4R)-2-(5-pyrimidinyl)-2,5-diazabicyclo[2.2.1]heptane;
(1R,4R)-2-(3-quinolinyl)-2,5-diazabicyclo[2.2.1]heptane;
(1R,4R)-2-(3-methyl-5-isothiazolyl)-2,5-diazabicyclo [2.2.1]heptane;
(1R,4R)-2-(5-bromo-3-pyridinyl)-2,5-diazabicyclo[2.2.1] heptane;
(1R,4R)-2-(6-methyl-3-pyridinyl)-2,5-diazabicyclo[2.2.1] heptane;
(1R,4R)-2-(6-nitro-3-pyridinyl)-2,5-diazabicyclo [2.2.1] heptane;
(1R,4R)-2-(6-fluoro-3-pyridinyl)-2,5-diazabicyclo[2.2.1] heptane;
(1R,4R)-2-(5-bromo-3-pyridinyl)-2,5-diazabicyclo[2.2.1] heptane;
(1R,4R)-2-(6-amino-3-pyridinyl)-2,5-diazabicyclo[2.2.1] heptane;
(1R,4R)-2-[5-(benzyloxy)-3-pyridinyl]-2,5-diazabicyclo [2.2.1]heptane;
(1R,4R)-2-(6-chloro-5-ethynyl-3-pyridinyl)-2,5diazabicyclo[2.2.1]heptane;
(1R,4R)-2-(6-chloro-5-cyano-3-pyridinyl)-2,5diazabicyclo [2.2.1]heptane;
(1R,4R)-2-(5-ethynyl-6-fluoro-3-pyridinyl)-2,5diazabicyclo [2.2.1]heptane;
(1R,4R)-2-(5-cyano-6-fluoro-3-pyridinyl)-2,5diazabicyclo [2.2.1]heptane;
(1R,4R)-2-(5-bromo-6-chloro-3-pyridinyl)-2,5diazabicyclo [2.2.1]heptane;
(1R,4R)-2-(5-cyano-6-chloro-3-pyridinyl)-2,5diazabicyclo [2.2.1]heptane;
(1R,4R)-2-(5-hydroxymethyl-6-chloro-3-pyridinyl)-2,5-diazabicyclo[2.2.1]heptane;
(1R,4R)-2-(5-hydroxymethyl-6-fluoro-3-pyridinyl)-2,5-diazabicyclo[2.2.1]heptane;
(1R,4R)-2-(5-hydroxymethyl-3-pyridinyl)-2,5-diazabicyclo [2.2.1]heptane;
(1R,4R)-2-(5-aminomethyl-6-chloro-3-pyridinyl)-2,5-diazabicyclo[2.2.1]heptane;
(1R,4R)-2-(5-aminomethyl-6-fluoro-3-pyridinyl)-2,5-diazabicyclo[2.2.1]heptane;
(1R,4R)-2-(5-aminomethyl-3-pyridinyl)-2,5-diazabicyclo [2.2.1]heptane;
(1R,4R)-2-(5-carboxy-6-chloro-3-pyridinyl)-2,5-diazabicyclo[2.2.1]heptane;
(1R,4R)-2-(5-carboxy-6-fluoro-3-pyridinyl)-2,5-diazabicyclo [2.2.1]heptane;
(1R,4R)-2-(5-carboxy-3-pyridinyl)-2,5-diazabicyclo[2.2.1] heptane;
(1R,4R)-2-(5-aminocarbonyl-6-fluoro-3-pyridinyl)-2,5-diazabicyclo[2.2.1]heptane;
(1R,4R)-2-(5-aminocarbonyl-6-chloro-3-pyridinyl)-2,5-diazabicyclo[2.2.1]heptane;
(1R,4R)-2-(6-chloro-5-hydroxyiminomethyl-3-pyridinyl)-2, 5-diazabicyclo [2.2.1]heptane;
(1R,4R)-2-(6-fluoro-5-hydroxyiminomethyl-3-pyridinyl)-2, 5-diazabicyclo[2.2.1]heptane;
(1R,4R)-2-(5-hydroxyiminomethyl-3-pyridinyl)-2,5-diazabicyclo[2.2.1]heptane;
(1R,4R)-2-(2-fluoro-3-pyridinyl)-2,5-diazabicyclo[2.2.1] heptane;
(1R,4R)-2-(5-methyl-6-fluoro-3-pyridinyl)-2,5-diazabicyclo[2.2.1]heptane;
(1R,4R)-2-(5-aminosulfonyl-6-fluoro-3-pyridinyl)-2,5-diazabicyclo[2.2.1]heptane;
(1R,4R)-2-(5-aminosulfonyl-6-chloro-3-pyridinyl)-2,5-diazabicyclo[2.2.1]heptane;
(1R,4R)-2-(5-aminosulfonyl-3-pyridinyl)-2,5-diazabicyclo [2.2.1]heptane;
(1R,4R)-2-(6-chloro-5-methyl-3-pyridinyl)-2,5-diazabicyclo[2.2.2]octane;
(1R,4R)-2-(5,6-dichloro-3-pyridinyl)-2,5-diazabicyclo [2.2.2]octane;
(1R,4R)-2-(6-chloro-5-ethynyl-3-pyridinyl)-2,5-diazabicyclo[2.2.2]octane;
(1R,4R)-2-(6-chloro-5-cyano-3-pyridinyl)-2,5-diazabicyclo [2.2.2]octane;
(1R,4R)-2-(5-methoxy-3-pyridinyl)-2,5-diazabicyclo[2.2.2] octane;
(1R,4R)-2-(6-fluoro-5-methyl-3-pyridinyl)-2,5-diazabicyclo[2.2.2]octane;
(1R,4R)-2-(6-fluoro-3-pyridinyl)-2,5-diazabicyclo[2.2.2] octane;
(1R,4R)-2-(5-ethynyl-6-fluoro-3-pyridinyl)-2,5-diazabicyclo[2.2.2]octane;
(1R,4R)-2-(5-cyano-6-fluoro-3-pyridinyl)-2,5-diazabicyclo [2.2.2]octane;
(1R,4R)-2-(5-bromo-6-chloro-3-pyridinyl)-2,5-diazabicyclo[2.2.2]octane;
(1R,4R)-2-(3-pyridinyl)-2,5-diazabicyclo[2.2.2]octane; and
(1R,4R)-2-(6-chloro-3-pyridinyl)-2,5-diazabicyclo [2.2.2] octane.

In another embodiment of the present invention are disclosed compounds of formula IV:

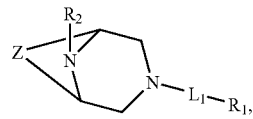

IV and their pharmaceutically acceptable salts wherein Z is selected from $CH_2CH_2$ and $CH_2CH_2CH_2$; and $L_1$, $R_1$, and $R_2$ are as defined in formula I.

Representative compounds of this embodiment include, but are not limited to:

3-(3-pyridazinyl)-3,8-diazabicyclo[3.2.1]octane;
3-(6-nitro-3-pyridinyl)-3,8-diazabicyclo[3.2.1]octane;
3-(6-amino-3-pyridinyl)-3,8-diazabicyclo[3.2.1]octane;
3-(6-chloro-3-pyridinyl)-3,8-diazabicyclo[3.2.1]octane; and
3-(3-pyridinyl)-3,8-diazabicyclo[3.2.1]octane.

The following additional compounds, representative of formula IV, may be prepared by one skilled in the art using known synthetic chemistry methodology or by using synthetic chemistry methodology described in the Schemes and Examples contained herein.

3-(6-chloro-5-methyl-3-pyridinyl)-3,8-diazabicyclo[3.2.1]octane;
3-(5,6-dichloro-3-pyridinyl)-3,8-diazabicyclo[3.2.1]octane;
3-(6-chloro-5-ethynyl-3-pyridinyl)-3,8-diazabicyclo[3.2.1]octane;
3-(6-chloro-5-cyano-3-pyridinyl)-3,8-diazabicyclo[3.2.1]octane;
3-(5-methoxy-3-pyridinyl)-3,8-diazabicyclo[3.2.1]octane;
3-(6-fluoro-5-methyl-3-pyridinyl)-3,8-diazabicyclo[3.2.1]octane;
3-(6-fluoro-3-pyridinyl)-3,8-diazabicyclo[3.2.1]octane;
3-(5-ethynyl-6-fluoro-3-pyridinyl)-3,8-diazabicyclo[3.2.1]octane;
3-(5-cyano-6-fluoro-3-pyridinyl)-3,8-diazabicyclo[3.2.1]octane;
3-(5-bromo-6-chloro-3-pyridinyl)-3,8-diazabicyclo[3.2.1]octane;
3-(5-aminomethyl-6-chloro-3-pyridinyl)-3,8-diazabicyclo[3.2.1]octane;
3-(5-aminomethyl-6-fluoro-3-pyridinyl)-3,8-diazabicyclo[3.2.1]octane; and
3-(5-aminomethyl-3-pyridinyl)-3,8-diazabicyclo[3.2.1]octane.

In another embodiment of the present invention are disclosed compounds of formula V:

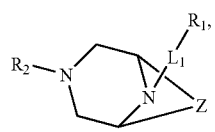

V and their pharmaceutically acceptable salts wherein Z is selected from $CH_2CH_2$ and $CH_2CH_2CH_2$; and $L_1$, $R_1$, and $R_2$ are as defined in formula I.

In another embodiment of the present invention are disclosed compounds of formula VI:

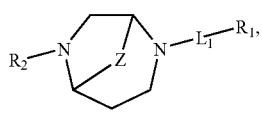

VI and their pharmaceutically acceptable salts wherein Z is selected from $CH_2$ and $CH_2CH_2$; and $L_1$, $R_1$, and $R_2$ are as defined in formula I.

A representative compound of this embodiment includes, but is not limited to:
2-(6-chloro-3-pyridinyl)-2,6-diazabicyclo[3.2.1]octane.

The following additional compounds, representative of formula VI, may be prepared by one skilled in the art using known synthetic chemistry methodology or by using synthetic chemistry methodology described in the Schemes and Examples contained herein.

2-(3-pyridinyl)-2,6-diazabicyclo[3.2.1]octane;
(1S,5R)-2-(6-chloro-5-methyl-3-pyridinyl)-2,6-diazabicyclo[3.2.1]octane;
(1S,5R)-2-(5,6-dichloro-3-pyridinyl)-2,6-diazabicyclo[3.2.1]octane;
(1S,5R)-2-(6-chloro-5-ethynyl-3-pyridinyl)-2,6-diazabicyclo[3.2.1]octane;
(1S,5R)-2-(6-chloro-5-cyano-3-pyridinyl)-2,6-diazabicyclo[3.2.1]octane;
(1S,5R)-2-(5-methoxy-3-pyridinyl)-2,6-diazabicyclo[3.2.1]octane;
(1S,5R)-2-(6-fluoro-5-methyl-3-pyridinyl)-2,6-diazabicyclo[3.2.1]octane;
(1S,5R)-2-(6-fluoro-3-pyridinyl)-2,6-diazabicyclo[3.2.1]octane;
(1S,5R)-2-(5-ethynyl-6-fluoro-3-pyridinyl)-2,6-diazabicyclo[3.2.1]octane;
(1S,5R)-2-(5-cyano-6-fluoro-3-pyridinyl)-2,6-diazabicyclo[3.2.1]octane;
(1S,5R)-2-(5-bromo-6-chloro-3-pyridinyl)-2,6-diazabicyclo[3.2.1]octane;
(1R,5S)-2-(6-chloro-5-methyl-3-pyridinyl)-2,6-diazabicyclo[3.2.1]octane;
(1R,5S)-2-(5,6-dichloro-3-pyridinyl)-2,6-diazabicyclo[3.2.1]octane;
(1R,5S)-2-(6-chloro-5-ethynyl-3-pyridinyl)-2,6-diazabicyclo[3.2.1]octane;
(1R,5S)-2-(6-chloro-5-cyano-3-pyridinyl)-2,6-diazabicyclo[3.2.1]octane;
(1R,5S)-2-(5-methoxy-3-pyridinyl)-2,6-diazabicyclo[3.2.1]octane;
(1R,5S)-2-(6-fluoro-5-methyl-3-pyridinyl)-2,6-diazabicyclo[3.2.1]octane;
(1R,5S)-2-(6-fluoro-3-pyridinyl)-2,6-diazabicyclo[3.2.1]octane;
(1R,5S)-2-(5-ethynyl-6-fluoro-3-pyridinyl)-2,6-diazabicyclo[3.2.1]octane;
(1R,5S)-2-(5-cyano-6-fluoro-3-pyridinyl)-2,6-diazabicyclo[3.2.1]octane; and
(1R,5S)-2-(5-bromo-6-chloro-3-pyridinyl)-2,6-diazabicyclo[3.2.1]octane.

In another embodiment of the present invention are disclosed compounds of formula VII:

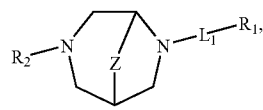

VII and their pharmaceutically acceptable salts wherein Z is selected from $CH_2$ and $CH_2CH_2$; and $L_1$, $R_1$, and $R_2$ are as defined in formula I.

The following compounds, representative of formula VII, may be prepared by one skilled in the art using known synthetic chemistry methodology or by using synthetic chemistry methodology described in the Schemes and Examples contained herein.

(1R,5R)-6-(6-chloro-5-methyl-3-pyridinyl)-3,6-diazabicyclo[3.2.1]octane;
(1R,5R)-6-(5,6-dichloro-3-pyridinyl)-3,6-diazabicyclo[3.2.1]octane;
(1R,5R)-6-(6-chloro-5-ethynyl-3-pyridinyl)-3,6-diazabicyclo[3.2.1]octane;
(1R,5R)-6-(6-chloro-5-cyano-3-pyridinyl)-3,6-diazabicyclo[3.2.1]octane;
(1R,5R)-6-(5-methoxy-3-pyridinyl)-3,6-diazabicyclo[3.2.1]octane;
(1R,5R)-6-(6-fluoro-5-methyl-3-pyridinyl)-3,6-diazabicyclo[3.2.1]octane;
(1R,5R)-6-(6-fluoro-3-pyridinyl)-3,6-diazabicyclo[3.2.1]octane;

(1R,5R)-6-(5-ethynyl-6-fluoro-3-pyridinyl)-3,6-diazabicyclo[3.2.1]octane;
(1R,5R)-6-(5-cyano-6-fluoro-3-pyridinyl)-3,6-diazabicyclo[3.2.1]octane;
(1R,5R)-6-(5-bromo-6-chloro-3-pyridinyl)-3,6-diazabicyclo[3.2.1]octane;
(1R,5R)-6-(3-pyridinyl)-3,6-diazabicyclo[3.2.1]octane;
(1R,5R)-6-(6-chloro-3-pyridinyl)-3,6-diazabicyclo[3.2.1]octane;
(1S,5S)-6-(6-chloro-5-methyl-3-pyridinyl)-3,6-diazabicyclo[3.2.1]octane;
(1S,5 S)-6-(5,6-dichloro-3-pyridinyl)-3,6-diazabicyclo[3.2.1]octane;
(1S,5 S)-6-(6-chloro-5-ethynyl-3-pyridinyl)-3,6-diazabicyclo[3.2.1]octane;
(1S,5S)-6-(6-chloro-5-cyano-3-pyridinyl)-3,6-diazabicyclo[3.2.1]octane;
(1S,5S)-6-(5-methoxy-3-pyridinyl)-3,6-diazabicyclo[3.2.1]octane;
(1S,5 S)-6-(6-fluoro-5-methyl-3-pyridinyl)-3,6-diazabicyclo[3.2.1]octane;
(1S,5 S)-6-(6-fluoro-3-pyridinyl)-3,6-diazabicyclo[3.2.1]octane;
(1S,5S)-6-(5-ethynyl-6-fluoro-3-pyridinyl)-3,6-diazabicyclo[3.2.1]octane;
(1S,5S)-6-(5-cyano-6-fluoro-3-pyridinyl)-3,6-diazabicyclo[3.2.1]octane;
(1S,5S)-6-(5-bromo-6-chloro-3-pyridinyl)-3,6-diazabicyclo[3.2.1]octane;
(1S,5 S)-6-(3-pyridinyl)-3,6-diazabicyclo[3.2.1]octane; and
(1S,5S)-6-(6-chloro-3-pyridinyl)-3,6-diazabicyclo[3.2.1]octane.

In another embodiment of the present invention are disclosed compounds of formula VIII:

and their pharmaceutically acceptable salts wherein Z is selected from $CH_2CH_2$ and $CH_2CH_2CH_2$; and $L_1$, $R_1$, and $R_2$ are as defined in formula I.

A representative compound of this embodiment includes, but is not limited to:
9-(6-chloro-3-pyridinyl)-3,9-diazabicyclo[4.2.1]nonane.

The following additional compounds, representative of formula VIII, may be prepared by one skilled in the art using known synthetic chemistry methodology or by using synthetic chemistry methodology described in the Schemes and Examples contained herein.
(1R,6S)-9-(6-chloro-5-methyl-3-pyridinyl)-3,9-diazabicyclo[4.2.1]nonane;
(1R,6S)-9-(5,6-dichloro-3-pyridinyl)-3,9-diazabicyclo[4.2.1]nonane;
(1R,6S)-9-(6-chloro-5-ethynyl-3-pyridinyl)-3,9-diazabicyclo[4.2.1]nonane;
(1R,6S)-9-(6-chloro-5-cyano-3-pyridinyl)-3,9-diazabicyclo[4.2.1]nonane;
(1R,6S)-9-(5-methoxy-3-pyridinyl)-3,9-diazabicyclo[4.2.1]nonane;
(1R,6S)-9-(6-fluoro-5-methyl-3-pyridinyl)-3,9-diazabicyclo[4.2.1]nonane;
(1R,6S)-9-(6-fluoro-3-pyridinyl)-3,9-diazabicyclo[4.2.1]nonane;
(1R,6S)-9-(5-ethynyl-6-fluoro-3-pyridinyl)-3,9-diazabicyclo[4.2.1]nonane;
(1R,6S)-9-(5-cyano-6-fluoro-3-pyridinyl)-3,9-diazabicyclo[4.2.1]nonane;
(1R,6S)-9-(5-bromo-6-chloro-3-pyridinyl)-3,9-diazabicyclo[4.2.1]nonane;
(1R,6S)-9-(6-chloro-3-pyridinyl)-3,9-diazabicyclo[4.2.1]nonane;
(1R,6S)-9-(3-pyridinyl)-3,9-diazabicyclo[4.2.1]nonane;
(1S,6R)-9-(6-chloro-5-methyl-3-pyridinyl)-3,9-diazabicyclo[4.2.1]nonane;
(1S,6R)-9-(5,6-dichloro-3-pyridinyl)-3,9-diazabicyclo[4.2.1]nonane;
(1S,6R)-9-(6-chloro-5-ethynyl-3-pyridinyl)-3,9-diazabicyclo[4.2.1]nonane;
(1S,6R)-9-(6-chloro-5-cyano-3-pyridinyl)-3,9-diazabicyclo[4.2.1]nonane;
(1S,6R)-9-(5-methoxy-3-pyridinyl)-3,9-diazabicyclo[4.2.1]nonane;
(1S,6R)-9-(6-fluoro-5-methyl-3-pyridinyl)-3,9-diazabicyclo[4.2.1]nonane;
(1S,6R)-9-(6-fluoro-3-pyridinyl)-3,9-diazabicyclo[4.2.1]nonane;
(1S,6R)-9-(5-ethynyl-6-fluoro-3-pyridinyl)-3,9-diazabicyclo[4.2.1]nonane;
(1S,6R)-9-(5-cyano-6-fluoro-3-pyridinyl)-3,9-diazabicyclo[4.2.1]nonane;
(1S,6R)-9-(5-bromo-6-chloro-3-pyridinyl)-3,9-diazabicyclo[4.2.1]nonane;
(1S,6R)-9-(6-chloro-3-pyridinyl)-3,9-diazabicyclo[4.2.1]nonane; and
(1S,6R)-9-(3-pyridinyl)-3,9-diazabicyclo[4.2.1]nonane.

In another embodiment of the present invention are disclosed compounds of formula IX:

and their pharmaceutically acceptable salts wherein Z is selected from $CH_2$ and $CH_2CH_2$; and $L_1$, $R_1$, and $R_2$ are as defined in formula I.

A representative compound of this embodiment includes, but is not limited to:
6-(6-chloro-3-pyridinyl)-2,6-diazabicyclo[3.2.1]octane.

The following additional compounds, representative of formula IX, may be prepared by one skilled in the art using known synthetic chemistry methodology or by using synthetic chemistry methodology described in the Schemes and Examples contained herein.
(1R,5S)-6-(6-chloro-5-methyl-3-pyridinyl)-2,6-diazabicyclo[3.2.1]octane;
(1R,5 S)-6-(5,6-dichloro-3-pyridinyl)-2,6-diazabicyclo[3.2.1]octane;
(1R,5S)-6-(6-chloro-5-ethynyl-3-pyridinyl)-2,6-diazabicyclo[3.2.1]octane;
(1R,5 S)-6-(6-chloro-5-cyano-3-pyridinyl)-2,6-diazabicyclo[3.2.1]octane;
(1R,5 S)-6-(5-methoxy-3-pyridinyl)-2,6-diazabicyclo[3.2.1]octane;
(1R,5 S)-6-(6-fluoro-5-methyl-3-pyridinyl)-2,6-diazabicyclo[3.2.1]octane;
(1R,5S)-6-(6-fluoro-3-pyridinyl)-2,6-diazabicyclo[3.2.1]octane;

(1R,5 S)-6-(5-ethynyl-6-fluoro-3-pyridinyl)-2,6-diazabicyclo[3.2.1]octane;
(1R,5 S)-6-(5-cyano-6-fluoro-3-pyridinyl)-2,6-diazabicyclo [3.2.1]octane;
(1R,5 S)-6-(5-bromo-6-chloro-3-pyridinyl)-2,6-diazabicyclo[3.2.1]octane;
(1R,5S)-6-(6-chloro-3-pyridinyl)-2,6-diazabicyclo[3.2.1] octane;
(1R,5 S)-6-(3-pyridinyl)-2,6-diazabicyclo[3.2.1]octane;
(1S,5R)-6-(6-chloro-5-methyl-3-pyridinyl)-2,6-diazabicyclo[3.2.1]octane;
(1S,5R)-6-(5,6-dichloro-3-pyridinyl)-2,6-diazabicyclo [3.2.1]octane;
(1S,5R)-6-(6-chloro-5-ethynyl-3-pyridinyl)-2,6-diazabicyclo[3.2.1]octane;
(1S,5R)-6-(6-chloro-5-cyano-3-pyridinyl)-2,6-diazabicyclo [3.2.1]octane;
(1S,5R)-6-(5-methoxy-3-pyridinyl)-2,6-diazabicyclo[3.2.1] octane;
(1S,5R)-6-(6-fluoro-5-methyl-3-pyridinyl)-2,6-diazabicyclo [3.2.1]octane;
(1S,5R)-6-(6-fluoro-3-pyridinyl)-2,6-diazabicyclo[3.2.1]octane;
(1S,5R)-6-(5-ethynyl-6-fluoro-3-pyridinyl)-2,6-diazabicyclo[3.2.1]octane;
(1S,5R)-6-(5-cyano-6-fluoro-3-pyridinyl)-2,6-diazabicyclo [3.2.1]octane;
(1S,5R)-6-(5-bromo-6-chloro-3-pyridinyl)-2,6-diazabicyclo [3.2.1]octane;
(1S,5R)-6-(6-chloro-3-pyridinyl)-2,6-diazabicyclo[3.2.1] octane; and
(1S,5R)-6-(3-pyridinyl)-2,6-diazabicyclo[3.2.1]octane.

In another embodiment of the present invention are disclosed compounds of formula X:

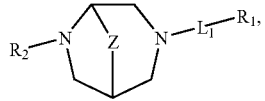

X and their pharmaceutically acceptable salts wherein Z is selected from $CH_2$ and $CH_2CH_2$; and $L_1$, $R_1$, and $R_2$ are as defined in formula I.

The following compounds, representative of formula X, may be prepared by one skilled in the art using known synthetic chemistry methodology or by using synthetic chemistry methodology described in the Schemes and Examples contained herein.
(1R,5R)-3-(6-chloro-5-methyl-3-pyridinyl)-3,6-diazabicyclo[3.2.1]octane;
(1R,5R)-3-(5,6-dichloro-3-pyridinyl)-3,6-diazabicyclo [3.2.1]octane;
(1R,5R)-3-(6-chloro-5-ethynyl-3-pyridinyl)-3,6-diazabicyclo[3.2.1]octane;
(1R,5R)-3-(6-chloro-5-cyano-3-pyridinyl)-3,6-diazabicyclo [3.2.1]octane;
(1R,5R)-3-(5-methoxy-3-pyridinyl)-3,6-diazabicyclo[3.2.1] octane;
(1R,5R)-3-(6-fluoro-5-methyl-3-pyridinyl)-3,6-diazabicyclo[3.2.1]octane;
(1R,5R)-3-(6-fluoro-3-pyridinyl)-3,6-diazabicyclo[3.2.1] octane;
(1R,5R)-3-(5-ethynyl-6-fluoro-3-pyridinyl)-3,6-diazabicyclo[3.2.1]octane;
(1R,5R)-3-(5-cyano-6-fluoro-3-pyridinyl)-3,6-diazabicyclo [3.2.1]octane;
(1R,5R)-3-(5-bromo-6-chloro-3-pyridinyl)-3,6-diazabicyclo[3.2.1]octane;
(1R,5R)-3-(6-chloro-3-pyridinyl)-3,6-diazabicyclo[3.2.1] octane;
(1R,5R)-3-(3-pyridinyl)-3,6-diazabicyclo[3.2.1]octane;
(1S,5 S)-3-(6-chloro-5-methyl-3-pyridinyl)-3,6-diazabicyclo[3.2.1]octane;
(1S,5S)-3-(5,6-dichloro-3-pyridinyl)-3,6-diazabicyclo [3.2.1]octane;
(1S,5S)-3-(6-chloro-5-ethynyl-3-pyridinyl)-3,6-diazabicyclo[3.2.1]octane;
(1S,5S)-3-(6-chloro-5-cyano-3-pyridinyl)-3,6-diazabicyclo [3.2.1]octane;
(1S,5S)-3-(5-methoxy-3-pyridinyl)-3,6-diazabicyclo[3.2.1] octane;
(1S,5S)-3-(6-fluoro-5-methyl-3-pyridinyl)-3,6-diazabicyclo [3.2.1]octane;
(1S,5S)-3-(6-fluoro-3-pyridinyl)-3,6-diazabicyclo[3.2.1]octane;
(1S,5 S)-3-(5-ethynyl-6-fluoro-3-pyridinyl)-3,6-diazabicyclo [3.2.1]octane;
(1S,5S)-3-(5-cyano-6-fluoro-3-pyridinyl)-3,6-diazabicyclo [3.2.1]octane;
(1S,5S)-3-(5-bromo-6-chloro-3-pyridinyl)-3,6-diazabicyclo [3.2.1]octane;
(1S,5S)-3-(6-chloro-3-pyridinyl)-3,6-diazabicyclo[3.2.1]octane; and
(1S,5S)-3-(3-pyridinyl)-3,6-diazabicyclo[3.2.1]octane.

In another embodiment of the present invention are disclosed compounds of formula XI:

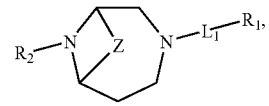

XI and their pharmaceutically acceptable salts wherein Z is selected from $CH_2CH_2$ and $CH_2CH_2CH_2$; and $L_1$, $R_1$, and $R_2$ are as defined in formula I.

Representative compounds of this embodiment include, but are not limited to:
3-(6-chloro-3-pyridinyl)-3,9-diazabicyclo[4.2.1]nonane;
9-methyl-3-(3-pyridinyl)-3,9-diazabicyclo[4.2.1]nonane; and
3-(3-pyridinyl)-3,9-diazabicyclo[4.2.1]nonane.

The following additional compounds, representative of formula XI, may be prepared by one skilled in the art using known synthetic chemistry methodology or by using synthetic chemistry methodology described in the Schemes and Examples contained herein.
(1R,6S)-3-(6-chloro-5-methyl-3-pyridinyl)-3,9-diazabicyclo [4.2.1]nonane;
(1R,6S)-3-(5,6-dichloro-3-pyridinyl)-3,9-diazabicyclo [4.2.1]nonane;
(1R,6S)-3-(6-chloro-5-ethynyl-3-pyridinyl)-3,9-diazabicyclo[4.2.1]nonane;
(1R,6S)-3-(6-chloro-5-cyano-3-pyridinyl)-3,9-diazabicyclo [4.2.1]nonane;
(1R,6S)-3-(5-methoxy-3-pyridinyl)-3,9-diazabicyclo[4.2.1] nonane;
(1R,6S)-3-(6-fluoro-5-methyl-3-pyridinyl)-3,9-diazabicyclo [4.2.1]nonane;
1R,6S)-3-(6-fluoro-3-pyridinyl)-3,9-diazabicyclo [4.2.1] nonane;
(1R,6S)-3-(5-ethynyl-6-fluoro-3-pyridinyl)-3,9-diazabicyclo[4.2.1]nonane;

(1R,6S)-3-(5-cyano-6-fluoro-3-pyridinyl)-3,9-diazabicyclo[4.2.1]nonane;
(1R,6S)-3-(5-bromo-6-chloro-3-pyridinyl)-3,9-diazabicyclo[4.2.1]nonane;
(1R,6S)-3-(6-chloro-3-pyridinyl)-3,9-diazabicyclo[4.2.1]nonane;
(1R,6S)-3-(3-pyridinyl)-3,9-diazabicyclo[4.2.1]nonane;
(1S,6R)-3-(6-chloro-5-methyl-3-pyridinyl)-3,9-diazabicyclo[4.2.1]nonane;
(1S,6R)-3-(5,6-dichloro-3-pyridinyl)-3,9-diazabicyclo[4.2.1]nonane;
(1S,6R)-3-(6-chloro-5-ethynyl-3-pyridinyl)-3,9-diazabicyclo[4.2.1]nonane;
(1S,6R)-3-(6-chloro-5-cyano-3-pyridinyl)-3,9-diazabicyclo[4.2.1]nonane;
(1S,6R)-3-(5-methoxy-3-pyridinyl)-3,9-diazabicyclo[4.2.1]nonane;
(1S,6R)-3-(6-fluoro-5-methyl-3-pyridinyl)-3,9-diazabicyclo[4.2.1]nonane;
(1S,6R)-3-(6-fluoro-3-pyridinyl)-3,9-diazabicyclo[4.2.1]nonane;
(1S,6R)-3-(5-ethynyl-6-fluoro-3-pyridinyl)-3,9-diazabicyclo[4.2.1]nonane;
(1S,6R)-3-(5-cyano-6-fluoro-3-pyridinyl)-3,9-diazabicyclo[4.2.1]nonane;
(1S,6R)-3-(5-bromo-6-chloro-3-pyridinyl)-3,9-diazabicyclo[4.2.1]nonane;
(1S,6R)-3-(6-chloro-3-pyridinyl)-3,9-diazabicyclo[4.2.1]nonane; and
(1S,6R)-3-(3-pyridinyl)-3,9-diazabicyclo[4.2.1]nonane.

In another embodiment of the present invention are disclosed compounds of formula XII:

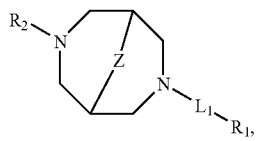

XII and their a pharmaceutically acceptable salts wherein Z is selected from $CH_2$ and $CH_2CH_2$; and $L_1$, $R_1$, and $R_2$ are as defined in formula I.

Representative compounds of this embodiment include, but are not limited to:
3-(3-pyridinyl)-3,7-diazabicyclo[3.3.1]nonane and
3-(6-chloro-3-pyridinyl)-3,7-diazabicyclo[3.3.1]nonane.

The following additional compounds, representative of formula XII, may be prepared by one skilled in the art using known synthetic chemistry methodology or by using synthetic chemistry methodology described in the Schemes and Examples contained herein.
3-(6-chloro-5-methyl-3-pyridinyl)-3,7-diazabicyclo[3.3.1]nonane;
3-(5,6-dichloro-3-pyridinyl)-3,7-diazabicyclo[3.3.1]nonane;
3-(6-chloro-5-ethynyl-3-pyridinyl)-3,7-diazabicyclo[3.3.1]nonane;
3-(6-chloro-5-cyano-3-pyridinyl)-3,7-diazabicyclo[3.3.1]nonane;
3-(5-methoxy-3-pyridinyl)-3,7-diazabicyclo[3.3.1]nonane;
3-(6-fluoro-5-methyl-3-pyridinyl)-3,7-diazabicyclo[3.3.1]nonane;
3-(6-fluoro-3-pyridinyl)-3,7-diazabicyclo[3.3.1]nonane;
3-(5-ethynyl-6-fluoro-3-pyridinyl)-3,7-diazabicyclo[3.3.1]nonane;
3-(5-cyano-6-fluoro-3-pyridinyl)-3,7-diazabicyclo[3.3.1]nonane; and
3-(5-bromo-6-chloro-3-pyridinyl)-3,7-diazabicyclo[3.3.1]nonane.

Another embodiment of the present invention relates to pharmaceutical compositions comprising a therapeutically effective amount of a compound of formula I or a pharmaceutically acceptable salt thereof in combination with a pharmaceutically acceptable carrier.

Another embodiment of the present invention relates to a method for selectively controlling neurotransmitter release in a mammal comprising administering to a mammal in need of such treatment a therapeutically effective amount of a compound of formula I.

Another embodiment of the present invention relates to a method of treating a disorder, such as Alzheimer's disease, Parkinson's disease, memory dysfunction, Tourette's syndrome, sleep disorders, attention deficit hyperactivity disorder, neurodegeneration, inflammation, neuroprotection, amyotrophic atral sclerosis, anxiety, depression, mania, schizophrenia, anorexia and other eating disorders, AIDS-induced dementia, epilepsy, urinary incontinence, Crohn's disease, migraines, premenstraul syndrome, erectile dysfunction, substance abuse, smoking cessation, inflammatory bowel syndrome, and pain, in a host mammal in need of such treatment comprising administering a therapeutically effective amount of a compound of formula I.

Definition of Terms

As used throughout this specification and the appended claims, the following terms have the following meanings.

The term "alkenyl," as used herein, refers to a straight or branched chain hydrocarbon containing from 2 to 6 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, and 4-pentenyl.

The term "alkoxy," as used herein, refers to an alkyl group, as defined herein, appended to the parent molecular moiety through an oxy moiety, as defined herein. Representative examples of alkoxy include, but are not limited to, methoxy, ethoxy, propoxy, 2-propoxy, butoxy, tert-butoxy, pentyloxy, and hexyloxy.

The term "alkoxyalkoxy," as used herein, refers to an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkyl," as used herein, refers to an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl," as used herein, refers to an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkyl," as used herein, refers to an alkoxycarbonyl group, as defined herein, appended to the parent molecular moiety through an alkyl group, as defined herein. Representative examples of alkoxycarbonylalkyl include, but are not limited to, 3-methoxycarbonylpropyl, 4-ethoxycarbonylbutyl, and 2-tert-butoxycarbonylethyl.

The term "alkyl," as used herein, refers to a straight or branched chain hydrocarbon containing from 1 to 6 carbon atoms. Representative examples of alkyl include, but are not limited to, methyl, ethyl, n-propyl, iso-propyl, n-butyl, sec-butyl, iso-butyl, tert-butyl, n-pentyl, isopentyl, and neopentyl.

The term "alkylcarbonyl," as used herein, refers to an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonyloxy," as used herein, refers to an alkylcarbonyl group, as defined herein, appended to the parent molecular moiety through an oxy moiety, as defined herein. Representative examples of alkylcarbonyloxy include, but are not limited to, acetyloxy, ethylcarbonyloxy, and tert-butylcarbonyloxy.

The term "alkylthio," as used herein, refers to an alkyl group, as defined herein, appended to the parent molecular moiety through a thio moiety, as defined herein. Representative examples of alkylthio include, but are not limited, methylsulfanyl, ethylsulfanyl, tert-butylsulfanyl, and hexylsulfanyl.

The term "alkynyl," as used herein, refers to a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "amino," as used herein, refers to —NR$_{10}$R$_{11}$, wherein R$_{10}$ and R$_{11}$, are independently selected from hydrogen, alkyl, alkylcarbonyl, and formyl, as defined herein. Representative examples of amino include, but are not limited to, amino, methylamino, ethylmethylamino, methylisopropylamino, dimethylamino, diisopropylamino, diethylamino, formylamino, and acetylethylamino.

The term "aminoalkyl," as used herein, refers to an amino group, as defined herein, appended to the parent molecular moiety through an alkyl group, as defined herein. Representative examples of aminoalkyl include, but are not limited to, aminomethyl, 2-aminoethyl, 3-aminopropyl, 4-amino-1-methylhexyl, and 2-(dimethylamino)ethyl.

The term "aminocarbonyl," as used herein, refers to an amino group, as defined herein, appended to the parent molecular moiety through a carbonyl group, as defined herein. Representative examples of aminocarbonyl include, but are not limited to, aminocarbonyl, dimethylaminocarbonyl, and ethylmethylaminocarbonyl.

The term "aminocarbonylalkyl," as used herein, refers to an aminocarbonyl group, as defined herein, appended to the parent molecular moiety through an alkyl group, as defined herein. Representative examples of aminocarbonylalkyl include, but are not limited to, 2-(aminocarbonyl)ethyl, 3-(dimethylaminocarbonyl)propyl, and ethylmethylaminocarbonylmethyl.

The term "aminosulfonyl," as used herein, refers to an amino group, as defined herein, appended to the parent molecular moiety through a sulfonyl group, as defined herein. Representative examples of aminosulfonyl include, but are not limited to, aminosulfonyl, dimethylaminosulfonyl, and ethylmethylaminosulfonyl.

The term "carbonyl," as used herein, refers to a —C(O)— group.

The term "carboxy," as used herein, refers to a —CO$_2$H group.

The term "carboxyalkyl," as used herein, refers to a carboxy group, as defined herein, appended to the parent molecular moiety through an alkyl group, as defined herein. Representative examples of carboxyalkyl include, but are not limited to, carboxymethyl, 2-carboxyethyl, and 3-carboxypropyl.

The term "cyano," as used herein, refers to a —CN group.

The term "cyanoalkyl," as used herein, refers to a cyano group, as defined herein, appended to the parent molecular moiety through an alkyl group, as defined herein. Representative examples of cyanoalkyl include, but are not limited to, cyanomethyl, 2-cyanoethyl, and 3-cyanopropyl.

The term "formyl," as used herein, refers to a —C(O)H group.

The term "formylalkyl," as used herein, refers to a formyl group, as defined herein, appended to the parent molecular moiety through an alkyl group, as defined herein. Representative examples of formylalkyl include, but are not limited to, formylmethyl and 2-formylethyl.

The term "halo" or "halogen," as used herein, refers to —Cl, —Br, —I or —F.

The term "haloalkoxy," as used herein, refers to at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl," as used herein, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "hydroxy," as used herein, refers to an —OH group.

The term "hydroxyalkyl," as used herein, refers to a hydroxy group, as defined herein, appended to the parent molecular moiety through an alkyl group, as defined herein. Representative examples of hydroxyalkyl include, but are not limited to, hydroxymethyl, 2-hydroxyethyl, and 3-hydroxypropyl.

The term "mercapto," as used herein, refers to a —SH group.

The term "mercaptoalkyl," as used herein, refers to a mercapto group, as defined herein, appended to the parent molecular moiety through an alkyl group, as defined herein. Representative examples of mercaptoalkyl include, but are not limited to, 2-mercaptoethyl and 3-mercaptopropyl.

The term "N-protecting group" or "nitrogen-protecting group," as used herein, refers to those groups intended to protect an amino group against undesirable reactions during synthetic procedures. N-protecting groups comprise carbamates, amides, alkyl derivatives, amino acetal derivatives, N-benzyl derivatives, imine derivatives, enamine derivatives, and N-heteroatom derivatives. Preferred N-protecting groups are formyl, acetyl, benzoyl, pivaloyl, phenylsulfonyl, benzyl, triphenylmethyl (trityl), t-butyloxycarbonyl (Boc), benzyloxycarbonyl (Cbz). Commonly used N-protecting groups are disclosed in T. H. Greene and P. G. M. Wuts, Protective Groups in Organic Synthesis, 2nd edition, John Wiley & Sons, New York (1991).

The term "nitro," as used herein, refers to a —NO$_2$ group.

The term "oxy," as used herein, refers to a —O— moiety.

The term "sulfonyl," as used herein, refers to a —SO$_2$— group.

The term "thio," as used herein, refers to a —S— moiety.

Compounds of the present invention can exist as stereoisomers, wherein asymmetric or chiral centers are present. Stereoisomers are designated "R" or "S," depending on the configuration of substituents around the chiral carbon atom. The terms "R" and "S" used herein are configurations as defined in *IUPAC 1974 Recommendations for Section E, Fundamental Stereochemistry, Pure Appl. Chem.*, (1976), 45: 13-30. In particular, the stereochemistry at the two bridgehead carbon atoms, shown in Formula (I), may independently be either (R) or (S), unless specifically noted otherwise. The present invention contemplates various stereoisomers and mixtures thereof and are specifically included within the scope of this invention. Stereoisomers include enantiomers, diastereomers, and mixtures of enantiomers or diastereomers. Individual stereoisomers of compounds of the present invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

The compounds of the present invention can be used in the form of pharmaceutically acceptable salts derived from inorganic or organic acids. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio.

Pharmaceutically acceptable salts are well-known in the art. For example, S. M. Berge et al. describe pharmaceutically acceptable salts in detail in *J. Pharmaceutical Sciences*, 1977, 66: 1 et seq. The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

Abbreviations

Abbreviations which have been used in the descriptions of the schemes and the examples that follow are: Ac for acetyl; AcOH for acetic acid; BINAP for 2,2'-bis(diphenylphosphino)-1,1'-binaphthyl; Boc for tert-butoxycarbonyl; (Boc)$_2$O for di-tert-butyl dicarbonate; dba for dibenzylideneacetone; DMF for N,N-dimethylformamide; dppf for 1,1'-bis (diphenylphosphino)ferrocene; EtOAc for ethyl acetate; Et$_2$O for diethyl ether; EtOH for ethanol; eq for equivalents; formalin for a solution of formaldehyde (37% by weight) in water; HPLC for high pressure liquid chromatography; LAH for lithium aluminum hydride; MeOH for methanol; Tf for SO$_2$CF$_3$; TFA for trifluoroacetic acid; THF for tetrahydrofuran; TMS for trimethylsilyl; and TsOH for para-toluenesulfonic acid monohydrate.

Preparation of Compounds of the Present Invention

The compounds and processes of the present invention will be better understood in connection with the following synthetic Schemes and methods which illustrate a means by which the compounds of the present invention can be prepared.

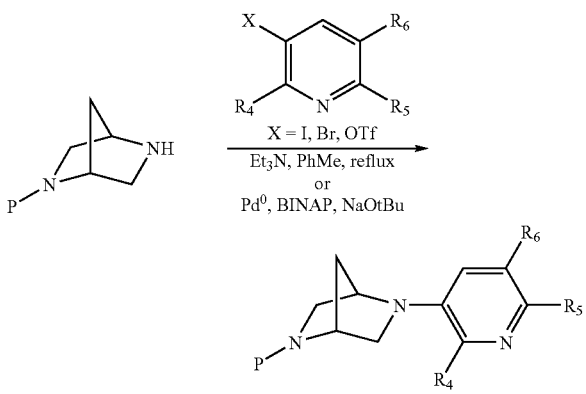

Scheme 1

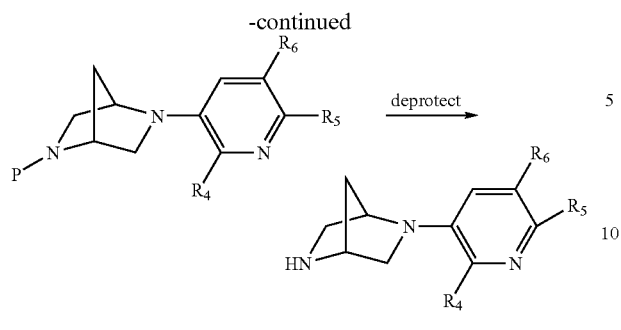

The compounds of the present invention can be prepared according to the general approach outlined in Scheme 1. Suitably protected bicyclic diamines, as shown in Scheme 1 wherein P is a nitrogen-protecting group such as alkyl, benzyl, or Boc, can be coupled with a halogenated heterocycle, wherein $R_4$, $R_5$, and $R_6$ are as defined in formula I, in the presence of an amine base. Alternatively, less-reactive heterocycles can be coupled using the procedures described in (Wagaw, S. and Buchwald, S. L., J. Org. Chem. 1996, 61, 7240-7241; Bryant, H. Y. and Buchwald, S. L., Journal of Organometallic Chemistry (1999) 576, 125-146). Deprotection under standard conditions affords the desired compounds. Diazabicycloheptanes may be prepared as generally taught and described in Examples 1, 2, 15, and 16. Diazabicyclooctanes may be prepared as generally taught and described in Examples 10, 35, 42, 49, 59, and 60. Diazabicyclononanes may be prepared as generally taught and described in Examples 36, 56, and 57. One skilled in the art would understand that the preparation of larger diazabicyclo compounds, for example decanes, etc., may be prepared synthetically by the Schemes and Examples contained herein as well as general synthetic methodology.

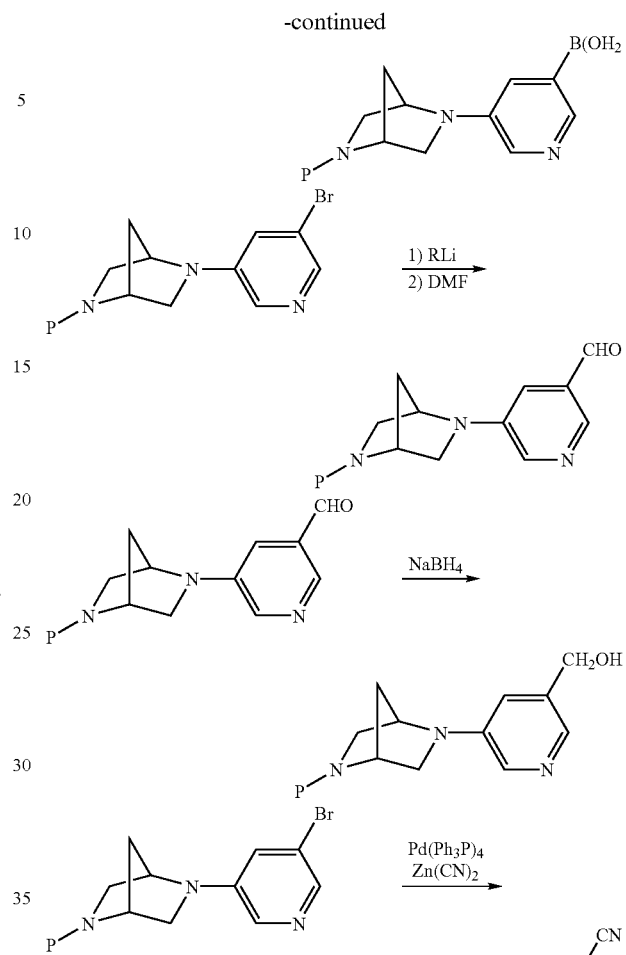

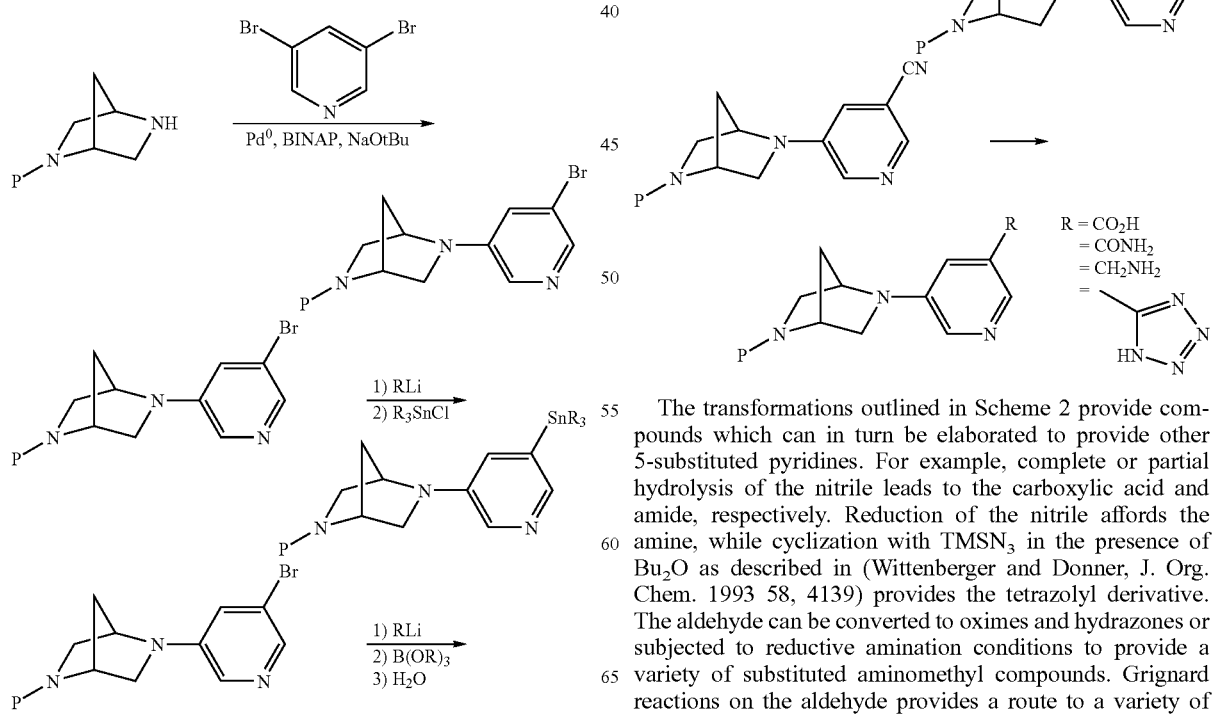

The transformations outlined in Scheme 2 provide compounds which can in turn be elaborated to provide other 5-substituted pyridines. For example, complete or partial hydrolysis of the nitrile leads to the carboxylic acid and amide, respectively. Reduction of the nitrile affords the amine, while cyclization with $TMSN_3$ in the presence of $Bu_2O$ as described in (Wittenberger and Donner, J. Org. Chem. 1993 58, 4139) provides the tetrazolyl derivative. The aldehyde can be converted to oximes and hydrazones or subjected to reductive amination conditions to provide a variety of substituted aminomethyl compounds. Grignard reactions on the aldehyde provides a route to a variety of substituted hydroxymethyl analogs.

Scheme 3

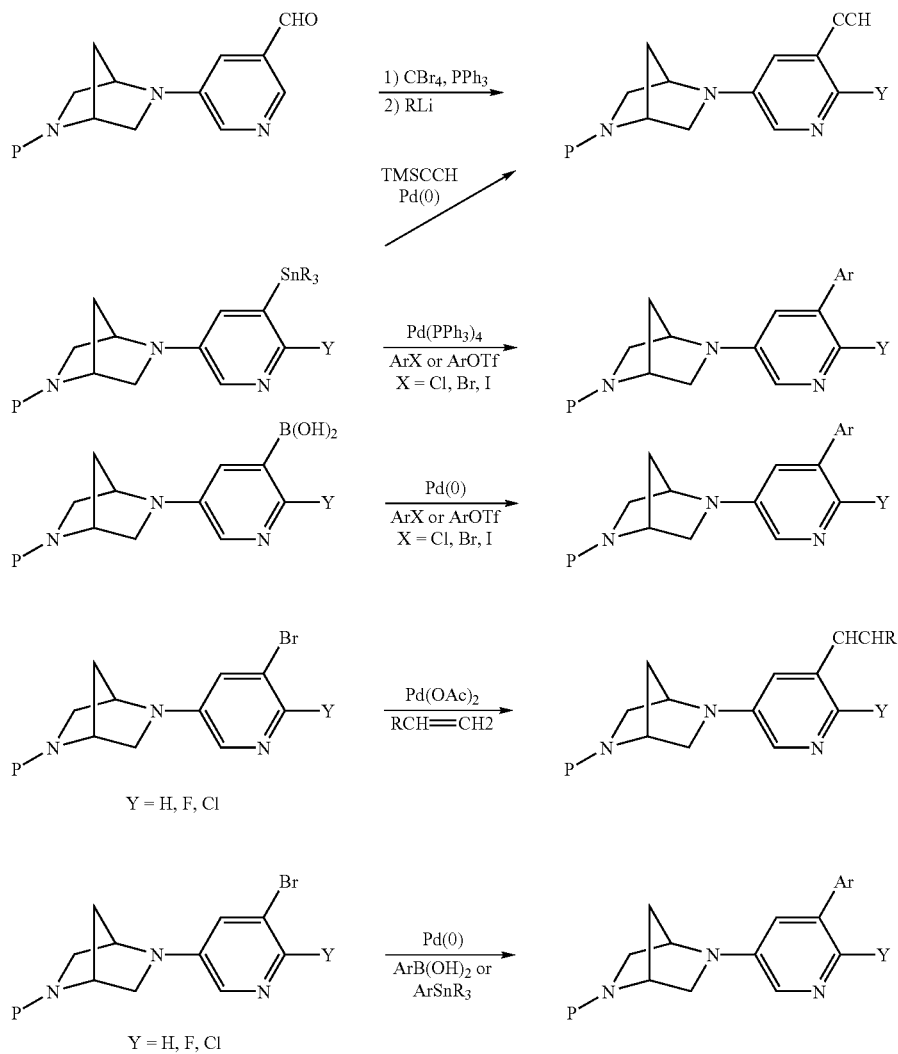

Aldehydes, as shown in Scheme 3, can be elaborated to terminal alkynes using the procedure described in (Tetrahedron Lett. (1972), 3769-3772). Additional elaborations are possible from the tin and boronic acid derivatives, from Scheme 2, which can be coupled with a variety of aryl and vinyl halides and sulfonate esters using transition metal catalysis (e.g., Stille and Suzuki couplings). The 5-bromo derivatives can be engaged in a variety of Pd-catalyzed couplings with alkenes and alkynes (Heck couplings), aryl and vinylstannanes and boronic acids (Stille and Suzuki couplings), as well as alkoxycarbonylations.

Scheme 4

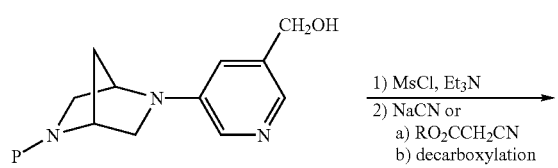

-continued

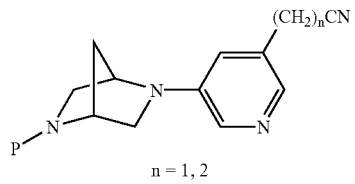

Chain extensions (CN displacement, malonic ester synthesis) can be carried out as described in Scheme 4 to provide the range of substitution patterns encompassed in the claims.

Scheme 5

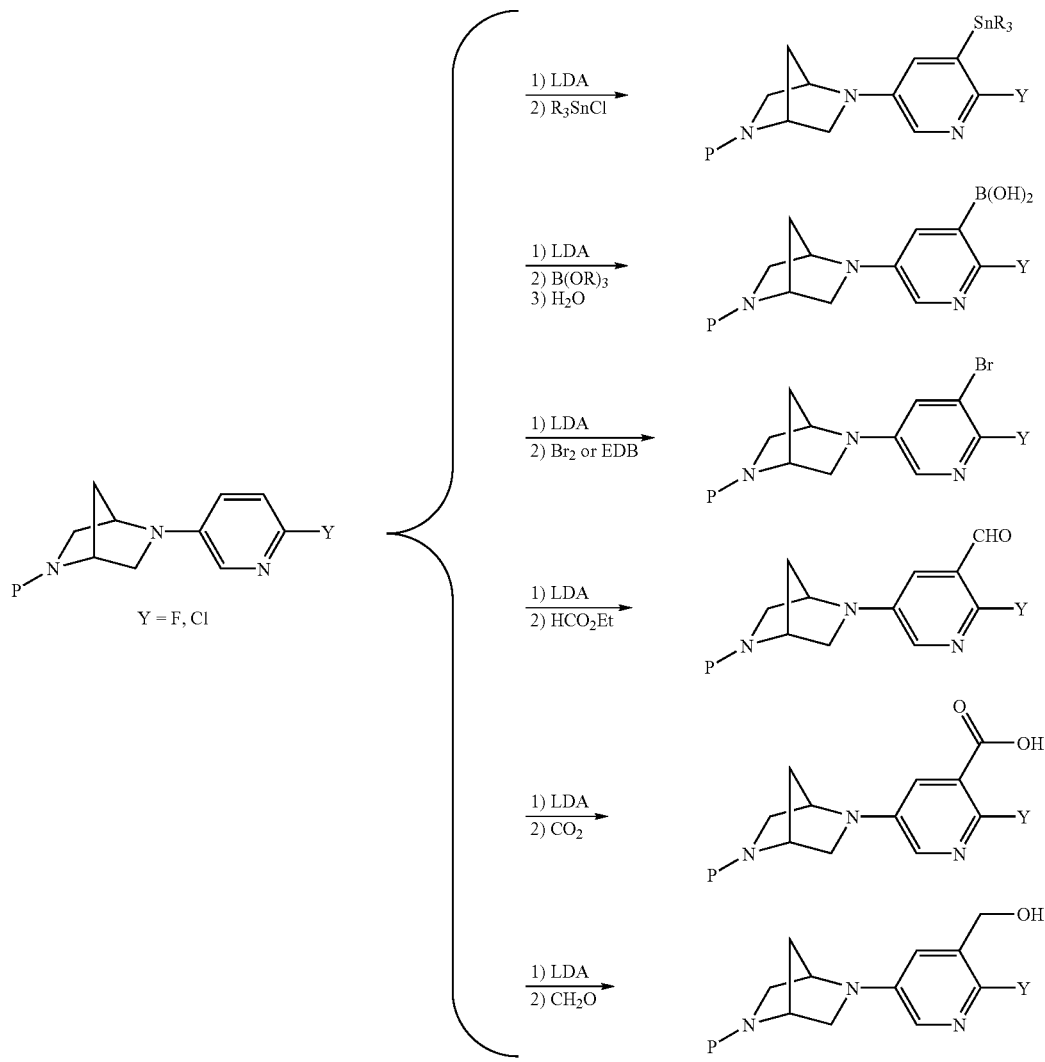

In the cases where the 6-position of the heterocycle is substituted with halogen, an alternate method for functionalizing the 5-position involves ortho-directed metalation according to (Gribble et al., Tetrahedron Lett. (1980) 21, 4137). The metalated species can be trapped with various electrophiles, as exemplified in Scheme 5, to afford intermediates which can be further elaborated as described in Schemes 3 and 4.

Scheme 6

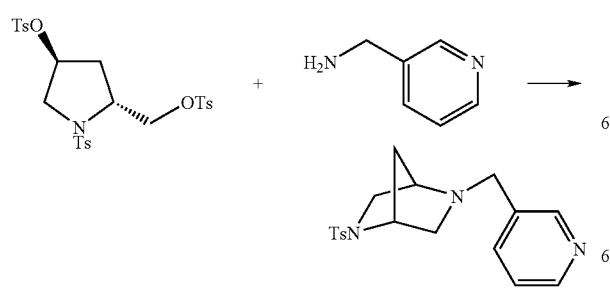

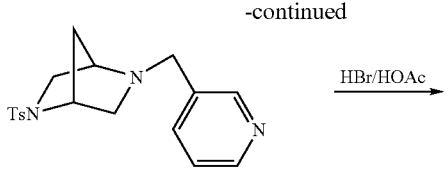

Compounds with 1-5 methylenes between the aromatic heterocycle and the diazabicyclic ring system can be prepared according to the procedure described in Scheme 6. Aminoalkyl heterocycles, prepared using standard synthetic chemistry methodology or purchased commercially, can be condensed with monocyclic precursors to provide N-substituted diazabicyclic systems. For example, (3S,5R)-1-[(4-methylphenyl)sulfonyl]-3-[(4-methylphenyl)sulfonyloxy]-

5-[(4-methylphenyl)sulfonyloxymethyl]pyrrolidine prepared as described in (J. Med. Chem., (1990) 33, 1344), can be condensed with an aminoalkylheterocycle to provide an N-substituted[2.2.1]diazabicyclic system which upon removal of the protecting group, for example with HBr/HOAc, provides the desired compounds. Other spacer lengths are possible by straightforward variation of the starting aminoalkyl heterocycle.

Scheme 7

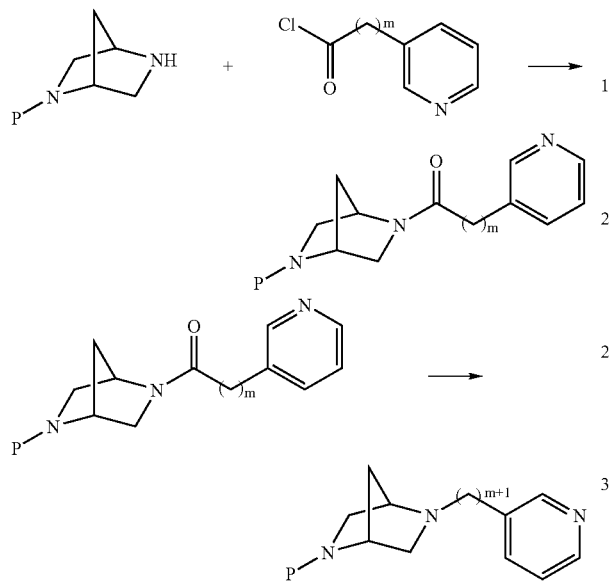

Scheme 7 describes an alternate method of preparing compounds with 1-5 methylenes between the aromatic heterocycle and the diazabicyclic ring system. Mono-protected diazabicyclic systems can be acylated with appropriate heterocyclic acid chlorides or anhydrides followed by reduction of the resultant amides using standard methods available to one skilled in the art provides the desired chain extended compounds.

The following examples are presented to describe preferred embodiments and utilities of the invention and are not meant to limit the invention unless otherwise stated in the claims appended hereto.

EXAMPLE 1

(1S,4S)-2-(6-chloro-3-pyridinyl)-2,5-diazabicyclo[2.2.1]heptane 4-methylbenzenesulfonate Example 1A tert-butyl (1S,4S)-5-(6-chloro-3-pyridinyl)-2,5-diazabicyclo[2.2.1]heptane-2-carboxylate In a dry, nitrogen-purged flask, tert-butyl (1S,4S)-2,5-diazabicyclo[2.2.1]heptane-2-carboxylate (330 mg, 1.6 mmol), prepared as described in (J. Med. Chem., (1988) 31, 1598-1611), in anhydrous toluene (6 mL) was treated with 2-chloro-5-iodopyridine (383 mg, 1.6 mmol), available as described in (Tetrahedron Lett., (1993), 34, 7493-7496), $Pd_2(dba)_3$ (156 mg, 0.16 mmol), BINAP (212 mg, 0.34 mmol), and sodium tert-butoxide (230 mg, 2.4 mmol). The mixture was heated at 70° C. for 24 hours. The reaction mixture was poured into diethyl ether (10 mL) and washed successively with 1N HCl, saturated $NaHCO_3$, and brine. The organic phase was dried ($MgSO_4$) and concentrated under reduced pressure. The residue was purified on $SiO_2$, eluting with ethyl acetate:hexanes (1:1) to provide the title compound (300 mg, 58% yield) as a light brown solid. $^1H$ NMR ($CDCl_3$, 300 MHz) δ 1.41(s, 4.5H), 1.46(s, 4.5H), 1.93-2.05(m, 2H), 3.14 (d, J=14.7 Hz, 0.5H), 3.35(d, J=14.7 Hz, 0.5H), 3.42(m, 2H), 3.57 (d, 8.45 Hz, 1H), 4.37(s, 1H), 4.53(s, 0.5H), 4.65(s, 0.5H), 6.82(dd, J=2.94, 8.83Hz, 1H), 7.13(d, J=8.46 Hz, 1H), 7.71(s, 1H); MS (DCI/$NH_3$) m/z 310 (M+H)$^+$.

Example 1B (1S,4S)-2-(6-chloro-3-pyridinyl)-2,5-diazabicyclo[2.2.1]heptane 4-methylbenzenesulfonate The product from Example 1A, tert-butyl (1S,4S)-5-(6-chloro-3-pyridinyl)-2,5-diazabicyclo[2.2.1]heptane-2-carboxylate (386 mg, 1.25 mmol), was charged to a dry, nitrogen-purged flask, and anhydrous ethanol (12 mL) was added. The solution was cooled to 0° C. and treated with 4N HCl/dioxane (1.3 mL). The mixture was allowed to warm to ambient temperature over 0.5 hours, the solvent was removed under reduced pressure, and the residue purified on $SiO_2$, eluting with 10% MeOH/$CH_2Cl_2$/1% $NH_4OH$ to afford the title compound (202 mg, 77% yield) as the free base. The free base was combined with p-toluenesulfonic acid (1 eq) and recrystallized from ethanol/ethyl acetate to provide the title compound. $^1H$ NMR (free base, $CDCl_3$, 300 MHz) δ 1.91-2.13 (AB quartet, J=17.6, 40.7 Hz, 2H), 3.03 (d, J=11.3Hz, 1H), 3.19 (s, 2H), 3.63 (dd, J=2.0, 11.3 Hz, 1H), 3.89 (s, 1H), 4.30 (s, 1H), 6.80 (dd, J=3.4, 8.9 Hz, 1H), 7.20 (d, J=8.8 Hz, 1H), 7.72 (d, J=3.3 Hz, 1H); MS (DCI/$NH_3$) m/z 210 (M+H)$^+$, 227 (M+$NH_4$)$^+$; Anal. calculated for $C_{10}H_{12}N_3Cl·1.25$ TsOH C, 52.92; H, 5.21; N, 9.69. Found: C, 52.92; H, 5.35; N, 9.64.

EXAMPLE 2

(1S,4S)-2-(6-chloro-3-pyridazinyl)-2,5-diazabicyclo[2.2.1]heptane bis(4-methylbenzenesulfonate)

Example 2A tert-butyl (1S,4S)-5-(6-chloro-3-pyridazinyl)-2,5-diazabicyclo[2.2.1]heptane-2-carboxylate tert-Butyl (1S,4S)-2,5-diazabicyclo[2.2.1]heptane-2-carboxylate (342 mg, 1.7 mmol), prepared as described in (J. Med. Chem., (1988) 31, 1598-1611), in anhydrous toluene (8.5 mL) was treated with 3,6-dichloropyridazine (256 mg, 1.7 mmol, Aldrich Chemical Company) and triethylamine (0.24 mL, 170 mg, 1.7 mmol). The reaction mixture was heated to reflux for 16 hours, concentrated under reduced pressure, and the residue purified on $SiO_2$ (5%MeOH/$CH_2Cl_2$/1%$NH_4OH$) to provide the title compound (432 mg, 81% yield) as a white solid. $^1H$ NMR ($CDCl_3$, 300 MHz) δ 1.42(s, 4.5H), 1.46(s, 4.5H), 1.91-2.05(m, 2H), 3.36-3.46 (m, 3H), 3.54-3.60 (m, 1H), 4.57(s, 0.5H), 4.70(s, 0.5H), 4.92(s, 0.5H), 5.07(s, 0.5H), 6.59(d, J=9.20 Hz, 1H), 7.34(d, J=9.56 Hz, 1H); MS (DCI/$NH_3$) m/z 311 (M+H)$^+$, 328(M+$NH_4$)$^+$.

Example 2B (1S,4S)-2-(6-chloro-3-pyridazinyl)-2,5-diazabicyclo[2.2.1]heptane bis(4-methylbenzenesulfonate)

The product from Example 2A (432 mg, 1.4 mmol) in EtOH (14 mL) at 0° C. was treated with 4M HCl/dioxane (1.4 mL). The reaction was allowed to warm to ambient temperature, concentrated under reduced pressure, and the residue was purified on $SiO_2$ (10%MeOH/$CH_2Cl_2$/1%$NH_4OH$) to provide the free base (231 mg, 79% yield). The free base was treated with p-toluenesulfonic acid (3 eq), and the resultant salt was recrystallized from ethanol/ethyl acetate. $^1H$ NMR (free base, $CDCl_3$, 300 MHz) δ 2.23 (d, J=11.77 Hz, 1H), 2.38 (d, J=11.77 Hz, 1H), 3.54 (AB quartet, J=11.77, 24.27 Hz, 2H), 3.90 (m, 2H), 4.72(s, 1H), 5.21 (s, 1H), 7.72 (d, J=9.56 Hz, 1H), 7.87 (d, J=9.92 Hz, 1H); MS (DCI/$NH_3$) m/z 211(M+H)$^+$, 228 (M+$NH_4$)$^+$; Anal. calculated for $C_9H_{11}N_4Cl.2.65$ TsOH.1.05$H_2O$, C, 48.24; H, 5.04; N, 8.17. Found: C, 48.29; H, 5.38; N, 8.18.

EXAMPLE 3

(1S,4S)-2-(6-amino-3-pyridinyl)-2,5-diazabicyclo[2.2.1]heptane trihydrochloride

Example 3A tert-butyl (1S,4S)-5-(6-nitro-3-pyridinyl)-2,5-diazabicyclo[2.2.1]heptane-2-carboxylate 5-Bromo-2-nitropyridine, prepared as described in (J. Am. Chem. Soc., (1945) 67, 668), and tert-butyl (1S,4S)-2,5-diazabicyclo[2.2.1]heptane-2-carboxylate, prepared as described in (J. Med. Chem., (1988) 31, 1598-1611), were coupled according to the procedure of Example 2A to provide the title compound.

Example 3B (1S,4S)-2-(6-amino-3-pyridinyl)-2,5-diazabicyclo[2.2.1]heptane trihydrochloride The product from Example 3A in methanol:ethanol (1:1) was treated with 10% Pd/C under a hydrogen atmosphere (1 atm) for 14 hours. The mixture was filtered, concentrated, and the residue treated with HCl/ether to provide the title compound (65% yield). $^1H$ NMR (DMSO-$d_6$, 300 MHz) δ 2.00 (m, 2H), 3.00 (br s, 2H), 3.4-3.5 (m, 2H), 4.40 (s, 1H), 4.60(s, 1H), 7.00 (d, J=6.3 Hz, 1H), 7.30 (s, 1H), 7.50 (br s, 2H, exchangeable), 7.70 (d, J=6.3 Hz 1H), 9.40 (br s, 1H, exchangeable), 9.80 (br s, 2H, exchangeable), 13.0 (br s, 1H, exchangeable).

EXAMPLE 4

(1S,4S)-2-(6-chloro-5-methyl-3-pyridazinyl)-2,5-diazabicyclo[2.2.1]heptane bis(4-methylbenzenesulfonate)

Example 4A tert-butyl (1S,4S)-5-(6-chloro-5-methyl-3-pyridazinyl)-2,5-diazabicyclo[2.2.1]heptane-2-carboxylate 3,6-Dichloro-4-methylpyridazine (Aldrich Chemical Company) and tert-butyl (1S,4S)-2,5-diazabicyclo[2.2.1]heptane-2-carboxylate, prepared as described in (J. Med. Chem., (1988) 31, 1598-1611), were processed as described in Example 2A to provide the title compound (56% yield). $^1H$ NMR ($CDCl_3$, 300 MHz) δ 1.41 (s, 4.5H), 1.43 (s, 4.5H), 1.90-2.09 (m, 2H), 2.31(s, 3H), 3.35-3.45 (m, 3H), 3.53-3.60(m, 1H), 4.56(s, 0.5H), 4.69(s, 0.5H), 4.90(s, 0.5H), 5.08(s, 0.5H), 6.48(s, 1H); MS (DCI/$NH_3$) m/z 325 (M+H)$^+$.

Example 4B (1S,4S)-2-(6-chloro-5-methyl-3-pyridazinyl)-2,5-diazabicyclo[2.2.1]heptane bis(4-methylbenzenesulfonate)

The product of Example 4A was processed as described in Example 2B to provide the title compound (81% yield). $^1H$ NMR ($CDCl_3$, 300 MHz) δ 1.84 (d, J=10.29 Hz, 1H), 1.96 (d, J=9.93 Hz,1H), 2.32 (s, 3H), 2.92-3.02 (m, 2H), 3.36 (s, 1H), 3.58 (dd, J=2.21, 9.56 Hz, 1H), 3.83 (s, 1H), 4.76-4.88 (m, 1H), 6.94 (s, 1H); MS (DCI/$NH_3$) m/z 225 (M+H)$^+$, 242 (M+$NH_4$)$^+$; Anal. calculated for $C_{10}H_{13}N_4Cl.2.0$ TsOH C, 50.63; H, 5.13; N-9.70. Found: C, 50.32; H, 5.15; N, 9.82.

EXAMPLE 5

(1S,4S)-2-(6-chloro-3-pyridazinyl)-5-methyl-2,5-diazabicyclo[2.2.1]heptane 4-methylbenzenesulfonate The product from Example 2B (1.0 eq) in formalin (0.1 M) was treated with NaCNBH$_3$ (1.2 eq) at 0° C. The reaction was allowed to warm to ambient temperature and stirred for 12 hours. The reaction mixture was quenched with saturated aqueous $K_2CO_3$, extracted with $CH_2Cl_2$, dried (MgSO$_4$), and concentrated under reduced pressure. The residue was purified on $SiO_2$ (10%MeOH/$CH_2Cl_2$/1%/$NH_4OH$) to provide the free base as a colorless oil (87% yield). The free base was treated with p-toluenesulfonic acid (1.5 eq) and the resultant salt was recrystallized from ethanol/ethyl acetate to provide the title compound. $^1H$ NMR (free base, $CD_3OD$, 300 MHz) δ 2.33 (d, J=10.30 Hz, 1H), 2.48 (s, 3H), 2.50 (d,J=11.77 Hz, 1H), 2.98-3.01 (m, 1H), 3.71-3.87 (m, 3H), 4.49 (s, 1H), 5.06 (s, 1H), 7.54 (d, J=10.26 Hz, 1H), 7.78 (d, J=8.09 Hz, 1H); MS (DCI/$NH_3$) m/z 225 (M+H)$^+$, 242 (M+$NH_4$)$^+$; Anal. calculated for $C_{10}H_{13}N_4Cl.0.95$ TsOH.0.60$H_2O$: C, 50.11; H, 5.51; N, 14.04. Found: C, 50.21; H, 5.76; N, 13.98.

EXAMPLE 6

(1S,4S)-2-(6-chloro-5-methyl-3-pyridazinyl)-5-methyl-2,5-diazabicyclo[2.2.1]heptane bis(4-methylbenzenesulfonate)

The product from Example 4B was processed as described in Example 5 to provide the title compound (39% yield). $^1H$ NMR ($CD_3OD$, 300 MHz) δ 1.89 (d, J=9.93 Hz, 1H), 2.05 (d, J=9.93 Hz, 1H), 2.29 (s, 3H), 2.45 (s, 3H), 2.76 (d, J=9.56 Hz, 1H), 2.97 (dd, J=1.83, 5.14 Hz, 1H), 3.39 (dd, J=2.21, 9.56 Hz,1H), 3.58-3.68 (m, 2H), 4.80 (br s, 1H), 6.48 (s,1H); MS (DCI/$NH_3$) m/z 239 (M+H)$^+$, 256 (M+$NH_4$)$^+$; Anal. calculated for $C_{11}H_{15}N_4Cl.2.2$ TsOH.1.80$H_2O$: C, 48.65; H, 5.62; N, 8.48. Found: C, 48.61; H, 5.50; N, 8.53.

EXAMPLE 7

(1S,4S)-2-(4-chloro-1-phthalazinyl)-2,5-diazabicyclo[2.2.1]heptane bis(4-methylbenzenesulfonate)

Example 7A tert-butyl (1S,4S)-5-(4-chloro-1-phthalazinyl)-2,5-diazabicyclo[2.2.1]heptane-2-carboxylate 1,4-Dichlorophthalazine (Aldrich Chemical Company) and tert-butyl (1S,4S)-2,5-diazabicyclo[2.2.1]heptane-2-carboxylate, prepared as described in (J. Med. Chem., (1988) 31, 1598-1611), were processed as described in Example 2A to provide the title compound (62% yield). $^1$H NMR (CDCl$_3$, 300 MHz) δ 1.44 (s, 4.5H), 1.47 (s, 4.5H), 1.95-2.08 (m, 2H), 3.46-3.58 (m, 1H), 3.64 (d, J=8.47 Hz, 0.5H), 3.75 (d, J=8.81 Hz, 0.5H), 3.91 (d, J=10.51 Hz, 1H), 4.19 (dd, J=2.03, 6.78 Hz, 1H), 4.59 (br s, 0.5H), 4.69 (br s, 0.5H), 5.15 (s, 1H), 7.26-7.81 (m, 2H), 8.04-8.12 (m, 1H), 8.21 (dd, J=1.70, 7.80 Hz, 1H); MS (DCI/NH$_3$) M/Z 361 (M+H)$^+$.

Example 7B

(1S,4S)-2-(4-chloro-1-phthalazinyl)-2,5-diazabicyclo[2.2.1]heptane bis(4-methylbenzenesulfonate)

The product of Example 7A was processed according to the procedure described in Example 2B to provide the title compound (83% yield). $^1$H NMR (free base, CDCl$_3$, 300 MHz) δ 1.91 (d, J=9.93 Hz, 1H), 2.05 (d, J=9.93 Hz, 1H), 3.22 (dd, J=1.84, 8.45 Hz, 1H), 3.55-3.70 (m, 2H), 3.95 (s, 1H), 4.21 (dd, J=2.21, 9.19 Hz, 1H), 5.07 (s, 1H), 7.76-7.94 (m, 2H), 8.06 (d, J=8.09 Hz, 1H), 8.15 (d, J=9.56 Hz, 1H); MS (DCI/NH$_3$) m/z 261 (M+H)$^+$; Anal. calculated for C$_{13}$H$_{13}$N$_4$Cl.2.105 TsOH.0.25H$_2$O: C, 53.08; H, 4.87; N, 8.94. Found: C, 53.14; H, 5.24; N, 8.87.

EXAMPLE 8

(1S,4S)-2-(4-chloro-1-phthalazinyl)-5-methyl-2,5-diazabicyclo[2.2.1]heptane bis(4-methylbenzenesulfonate)

The product of Example 7B was processed according to the procedure described in Example 5 to provide the title compound (53% yield). $^1$H NMR free base (CD$_3$OD, 300 MHz) δ 2.34 (s, 3H), 2.54 (d, J=8.47 Hz, 1H), 2.68 (d, J=10.51 Hz, 1H), 3.48 (d, J=11.19 Hz, 1H), 4.28-4.45 (m, 2H), 4.59-4.66 (m, 2H), 5.34 (s, 1H), 8.08-8.15 (m, 1H), 8.23 (t, J=7.80 Hz, 1H), 8.38-8.46 (m, 2H); MS (DCI/NH$_3$) m/z 275 (M+H)$^+$; Anal. calculated for C$_{14}$H$_{15}$N$_4$Cl.2.0 TsOH: C, 54.52; H, 5.50; N, 9.05. Found: C, 54.18; H, 4.98; N, 9.08.

EXAMPLE 9

(1S,4S)-2-(6-chloro-5-methoxycarbonyl-3-pyridazinyl)-2,5-diazabicyclo[2.2.1]heptane bis(4-methylbenzenesulfonate)

Example 9A tert-butyl (1S,4S)-5-[6-chloro-5-(methoxycarbonyl)-3-pyridazinyl]-2,5-diazabicyclo[2.2.1]heptane-2-carboxylate Methyl 3,6-dichloropyridazine-4-carboxylate and tert-butyl (1S,4S)-2,5-diazabicyclo[2.2.1]heptane-2-carboxylate, prepared as described in (J. Med. Chem., (1988) 31, 1598-1611), were processed as described in Example 2A to provide the title compound (41% yield). $^1$H NMR (CDCl$_3$, 300 MHz) δ 1.42 (s, 4.5H), 1.47 (s, 4.5H), 1.90-2.11 (m, 2H), 2.86 (d, J=9.93 Hz, 1H), 3.40-3.62 (m, 2H), 3.72 (d, J=9.90 Hz, 1H), 3.93 (s, 3H), 3.51 (s, 0.5H), 4.63 (s, 0.5H), 5.05-5.15 (m, 1H), 7.49 (s, 1H); MS (DCI/NH$_3$) m/z 368 (M+H)$^+$.

Example 9B

(1S,4S)-2-(6-chloro-5-methoxycarbonyl-3-pyridazinyl)-2,5-diazabicyclo[2.2.1]heptane bis(4-methylbenzenesulfonate)

The product from Example 9A was processed according to the procedure described in Example 2B to provide the title compound (73% yield). $^1$H NMR (CDCl$_3$, 300 MHz) δ 1.88 (d, J=10.29 Hz, 1H), 2.01 (d, J=9.92 Hz, 1H), 2.81 (d, J=9.92 Hz, 1H), 3.13-3.27 (m, 2H), 3.76 (dd, J=2.21, 9.93 Hz, 1H), 3.87 (s, 1H), 3.93 (s, 3H), 5.00 (s, 1H), 7.48 (s, 1H); MS (DCI/NH$_3$) m/z 269 (M+H)$^+$; Anal. calculated for C$_{11}$H$_{13}$N$_4$O$_2$Cl.2.5 TsOH.1.1H$_2$O: C, 47.61; H, 4.93; N, 7.79. Found: C, 47.61; H, 5.07; N, 7.75.

EXAMPLE 10

3-(6-nitro-3-pyridinyl)-3,8-diazabicyclo[3.2.1]octane dihydrochloride

Example 10A tert-butyl 3-(6-nitro-3-pyridinyl)-3,8-diazabicyclo[3.2.1]octane-8-carboxylate tert-Butyl 3,8-diazabicyclo[3.2.1]octane-8-carboxylate (0.4 g; 1.9 mmol), prepared as described in (J. Med. Chem., (1998) 41, 674), 5-bromo-2-nitropyridine (0.43 g; 2.27 mmol), prepared as described in (J. Am. Chem. Soc., (1945) 67, 668), and triethylamine (0.23 g; 2.27 mmol) in toluene (10 mL) were heated at reflux for 14 hours. After evaporation of the solvent, additional triethylamine (0.23 g) was added and the mixture further heated at 140° C. for 2 hours. The residue was purified on SiO$_2$ (CH$_2$Cl$_2$:EtOAc 9:1) to provide the title compound.

Example 10B

3-(6-nitro-3-pyridinyl)-3,8-diazabicyclo[3.2.1]octane dihydrochloride

The product from Example 10A was treated with 1M HCl/ether to provide the title compound (55% yield). $^1$H NMR (DMSO-d$_6$, 300 MHz) δ 1.9-2.0 (m, 4H), 3.4-3.5 (m, 2H), 4.00 (d, J=11 Hz, 2H), 4.20 (br s, 2H), 7.5-7.6 (m, 1H), 8.2-8.3 (m, 2H), 9.6-9.7 (br s, 3H, exchangeable).

EXAMPLE 11

3-(6-amino-3-pyridinyl)-3,8-diazabicyclo[3.2.1]octane trihydrochloride

Example 11A tert-butyl 3-(6-amino-3-pyridinyl)-3,8-diazabicyclo[3.2.1]octane-8-carboxylate The product from Example 10A (200 mg) was treated with 10% Pd/C (20 mg) in a 1:1 mixture of methanol:ethanol (5 mL) under a hydrogen atmosphere (1 atm). After filtration to remove the catalyst, the filtrate was concentrated and the residue triturated with diethyl ether to afford the title compound as a violet solid.

Example 11B 3-(6-amino-3-pyridinyl)-3,8-diazabicyclo[3.2.1]octane trihydrochloride The product from Example 11A was treated with 1M HCl/ether to provide the title compound (72% yield). $^1$H NMR (DMSO-d$_6$, 300 MHz) δ 2.00 (s, 4H), 3.2 (d, J=11 Hz, 2H), 3.4 (s, J=11 Hz, 2H), 4.20 (br s, 2H), 5.80 (s, 2H, exchangeable), 7.00, (d, J=8.5 Hz, 1H), 7.40 (br s, 1H), 7.80 (br s, 2H, exchangeable), 7.9-8.0 (m, 1H), 9.10 (br s, 2H, exchangeable).

EXAMPLE 12

3-(6-chloro-3-pyridinyl)-3,8-diazabicyclo[3.2.1]octane dihydrochloride

The product from Example 11A (0.03 g; 0.103 mmol) in 12M HCl (0.13 mL) was treated with sodium nitrite (10 mg, 0.129 mmol) at 0° C. The reaction mixture was allowed to warm to ambient temperature and stir overnight. The mixture was neutralized by addition of NaHCO$_3$ and then extracted with CH$_2$Cl$_2$. The extracts were dried (Na$_2$SO$_4$), concentrated under reduced pressure, and the residue purified on SiO$_2$ (10% MeOH/CH$_2$Cl$_2$/1% NH$_4$OH) to provide the free base. The free base was treated with 1M HCl/ether to provide the title compound (43% yield). $^1$H NMR free base (CDCl$_3$, 300 MHz) δ 1.8 (m, 4H), 2.1 (br s, 1H, exchangeable), 3.0 (d.K=11 Hz, 2H), 3.4-3.7 (br s, 2H), 7.0-7.2 (m, 2H0, 7.9 (m, 1H).

EXAMPLE 13

3-(3-pyridinyl)-3,8-diazabicyclo[3.2.1]octane dihydrochloride

The product from Example 12 was processed as described in Example 11A. The crude product was purified on SiO$_2$ (10% MeOH/CH$_2$Cl$_2$/1% NH$_4$OH) and then treated with 1M HCl/ether to provide the title compound (40% yield). $^1$H NMR (DMSO-d$_6$, 300 MHz)δ 2.20 (br s, 4H), 3.5 (d, J=11 Hz, 2H), 4.00 (d, J=11 Hz, 2H), 4.4 (br s, 1H), 7.9-8.0 (m, 1H), 8.2-8.3 (m, 2H), 8.5 (d, J=3.6 Hz, 1H); MS (DCI/NH$_3$) m/z 190 (M+H)$^+$.

EXAMPLE 14

3-(3-pyridazinyl)-3,8-diazabicyclo[3.2.1]octane dihydrochloride 3-(6-Chloro-3-pyridazinyl)-3,8-diazabicyclo[3.2.1]octane, prepared as described in (J. Med. Chem., (1998) 41, 674) was hydrogenated according to the procedure described in Example 11A. The crude product was purified on SiO$_2$ (10% MeOH/CH$_2$Cl$_2$/1% NH$_4$OH) and treated with 1M HCl/ether to afford the title compound (40% yield). $^1$H NMR (free base, CDCl$_3$, 300 MHz) δ 1.9-2.0 (m, 5H), 3.1 (d, J=11 Hz, 2H), 3.70 (br s, 2H), 4.0 (d, J=11 Hz, 2H), 6.8 (d, J=8.8 Hz, 1H), 7.2 (dd, J=8.8, 3.8 Hz, 1H), 8.6 (d, J=3.6 Hz, 1H); MS (DCI/NH$_3$) m/z 191 (M+H)$^+$.

EXAMPLE 15

(1R,4R)-2-(6-chloro-3-pyridinyl)-2,5-diazabicyclo[2.2.1]heptane 4-methylbenzenesulfonate Example 15A tert-butyl (1R,4R)-5-benzyl-2,5-diazabicyclo[2.2.1]heptane-2-carboxylate (1R,4R)-2-(benzyl)-2,5-diazabicylo[2.2.1]heptane dihydrobromide (12.4 g, 35.5 mmol), prepared as described in (J. Med. Chem., (1990) 33, 1344) and K$_2$CO$_3$ (16.2 g, 117 mmol) in 100 mL of DMF were treated with di-tert-butyl dicarbonate (8.1 g, 37 mmol) at ambient temperature. After stirring for 16 hours, the mixture was filtered and the filtrate diluted with water (500 mL). The mixture was extracted with Et$_2$O (3×300 mL). The extracts were combined, washed with 50% brine (10×20 mL), dried over MgSO$_4$, and the solvent removed under reduced pressure to provide the title compound (9.7 g, 94%). $^1$H NMR (DMSO-d$_6$, 300 MHz) δ 1.62 (m, 1H), 1.79 (d, J=9.2 Hz, 1H), 2.51 (m, 1H), 2.75 (m, 1H) 3.07 (t, J=10.2 Hz, 1H), 3.32-3.41 (m, 2H), 3.67 (s, 1H), 4.16 (d, 9.8 Hz, 1H), 7.19-7.33 (m, 5H); MS (DCI/NH$_3$) m/z 199 (M+H)$^+$, 216 (M+NH$_4$)$^+$.

Example 15B tert-butyl (1R,4R)-2,5-diazabicyclo[2.2.1]heptane-2-carboxylate

The product from Example 15A (2 g, 6.9 mmol) in 50 mL of EtOH was treated with 10% Pd/C (150 mg) under an H$_2$ atmosphere (1 atm) for 16 hours. The mixture was filtered and the solvent was evaporated under reduced pressure to yield 1.28 g (93.4%) of the title compound. $^1$H NMR (DMSO-d$_6$, MHz) δ 1.39 (s, 9H), 1.54 (d, J=5.6 Hz, 1H), 1.58 (t, J=9.5 Hz, H), 2.70-2.81 (M, 2H), 3.50 (dd, J=1.02, 10.50, 1H), 3.17 (m, 1H), 3.50 (s, 1H), 4.17 (d, J=10.17 Hz, H); MS (DCI/NH$_3$) m/z 199 (M+H)$^+$, 216 (M+NH$_4$)$^+$.

Example 15C tert-butyl (1R,4R)-5-(6-chloro-3-pyridinyl)-2,5-diazabicyclo[2.2.1]heptane-2-carboxylate The product from Example 15B (0.5 g, 2.5 mmole), 2-chloro-5-iodopyridine (0.88 g, 3.35 mmole, available as described in Tetrahedron Lett., 1993, 34, 7493-7496), Pd$_2$(dba)$_3$ (0.13 g, 0.16 mmole), BINAP (0.22 g, 0.34 mmole), and sodium tert-butoxide (0.325 g, 3.57 mmole) in anhydrous toluene (10 mL) were heated to 70° C. for 16 hours. The mixture was filtered, concentrated under reduced pressure, and the residue purified by chromatography (silica gel; hexane:EtOAc, 9:1 to 1:1) to provide the title compound (0.522 g, 67%). $^1$H NMR (DMSO-d$_6$, 300 MHz) δ 1.33-1.38 (m 9H), 2.50 (br s, 2H), 3.02 (m, 1H), 3.16 (d, J=10.17 Hz, 1H), 3.27 (m, 1H), 3.53 (m, 1H), 4.43 (m, 1H), 4.58 (br, s 1H), 7.11 (dd, J=3.05, 8.81 Hz, 1H), 7.24 (d, J=27.46 Hz, 1H), 7.77 (d, J=3.05 Hz, 1H); MS (DCI/NH$_3$) m/z 310 (M+H)$^+$.

Example 15D (1R,4R)-2-(6-chloro-3-pyridinyl)-2,5-diazabicyclo[2.2.1]heptane 4-methylbenzenesulfonate The product of Example 15C (478 mg, 1.5 mmole) in CH$_2$Cl$_2$ (3 mL) was treated with trifluoroacetic acid (3 mL).

After stirring for one hour at ambient temperature, the solvent was removed and the residue dissolved in saturated $Na_2CO_3$ (20 mL). The mixture was extracted with EtOAc (4×20 mL), dried over $MgSO_4$, concentrated under reduced pressure, and the residue purified ($SiO_2$; 10% MeOH/ $CHCl_3$/1% $NH_4OH$) to provide the free base. The free base was treated with TsOH in hot EtOAc to provide the title compound (451 mg, 71%). $[\alpha]_D^{23}$ −8.21 (c 0.21, MeOH); $^1$H NMR (DMSO-$d_6$, 300 MHz) δ 1.93 (d, J=11.52 Hz, 1H), 2.14 (d J=11.19 Hz 1H), 2.29 (s, 3H), 3.13-3.31 (m, 3H), 3.61 (dd, J=2.37, 10.85, 1H), 4.48 (s, 1H), 4.68 (s, 1H), 7.13 (d, J=8.48 Hz, 2H), 7.17 (dd, J=3.05, 8.62 Hz, 1H), 7.31 (d, J=8.82 Hz, 1H), 7.49 (d J=7.66 Hz, 2H), 7.85 (d J=3.39 Hz, 1H); MS (DCI/$NH_3$) m/z 210 (M+H)$^+$; Anal. Calcd. for $C_{10}H_{12}N_3Cl·C_7H_8O_3S$: C, 53.47; H, 5.28; N, 11.00. Found: C, 53.43; H, 5.36; N, 10.97.

EXAMPLE 16

(1R,4R)-2-(6-chloro-3-pyridazinyl)-2,5-diazabicyclo [2.2.1]heptane bis(4-methylbenzenesulfonate)

Example 16A tert-butyl (1R,4R)-5-(6-chloro-3-pyridazinyl)-2,5-diazabicyclo[2.2.1]heptane-2-carboxylate The product from Example 15B and 3,6-dichloropyridazine (purchased from Aldrich Chemical Co.) were processed as described in Example 2A to provide the title compound. $^1$H NMR (DMSO-$d_6$, 300 MHz) δ 1.48 (m 9H), 2.93 (br, s 2H), 3.18 (d, J=12.17 Hz, 1H), 3.3-3.51 (m, 2H), 3.55 (m, 1H), 4.49 (m, 1H), 4.86 (br, s 1H), 7.12 (m, 1H), 7.51 (d, J=9.49 Hz, 1H); MS (DCI/$NH_3$) m/z 311 (M+H)$^+$.

Example 16B (1R,4R)-2-(6-chloro-3-pyridazinyl)-2,5-diazabicyclo [2.2.1]heptane bis(4-methylbenzenesulfonate)

The product from Example 16A (353 mg, 1.1 mmole) and para-toluenesulfonic acid (660 mg 3.5 mmole) in EtOAc (10 mL) were heated at 70° C. for one hour and then cooled to ambient temperature. The obtained solid was washed with EtOAc (2×10 mL), ether (2×10 mL), and dried under reduced pressure to provide the title compound (597 mg, 94.7%). $[\alpha]_D^{23}$ +59.3 (c 1.0, MeOH); $^1$H NMR (DMSO-$d_6$, 300 MHz) δ 1.96 (d, J=10.51 Hz, 1H), 2.17 (d, J=10.17 Hz 1H), 2.29 (s, 6H), 3.24-3.28 (m, 2H), 3.56-3.67 (m, 2H), 4.53 (s, 1H), 4.95 (s, 1H), 7.11 (d, J=7.79 Hz, 4H), 7.21 (d, J=9.41 Hz,1H), 7.49 (d, J=8.11 Hz, 4H), 7.62 (d, J=9.49 Hz, 1H); MS (DCI/$NH_3$) m/z 211 (M+H)$^+$; Anal. Calcd. for $C_9H_{11}N_4Cl·2C_7H_8O_3S$: C, 49.77; H, 4.90; N, 10.09. Found: C, 49.77; H, 4.99; N, 9.96.

EXAMPLE 17

(1S,4S)-2-(3-pyridinyl)-2,5-diazabicyclo[2.2.1]heptane 4-methylbenzenesulfonate

Example 17A tert-butyl (1S,4S)-5-(3-pyridinyl)-2,5-diazabicyclo [2.2.1]heptane-2-carboxylate tert-Butyl (1S,4S)-2,5-diazabicyclo[2.2.1]heptane-2-carboxylate, prepared as described in J. Med. Chem., (1988) 31, 1598-1611, and 3-bromopyridine (Aldrich Chemical Company) were processed as described in Example 1A to provide the title compound (99% yield). $^1$H NMR (CDCl$_3$, 300 MHz) δ 1.42 (s, 4.5H), 1.48 (s, 4.5H), 1.91-2.03 (m, 2H),3.14 (d, J=14.7 Hz, 0.5H), 3.23 (d, J=14.7 Hz, 0.5H), 3.37-3.48 (m, 2H), 3.60 (d, 8.45 Hz, 1H), 4.41 (s, 1H), 4.53 (s, 0.5H), 4.67 (s, 0.5H), 6.85 (dd, J=2.94, 8.83 Hz, 1H), 7.09-7.21 (m, 1H), 7.95-8.06 (m, 2H); MS (DCI/$NH_3$) m/z 276 (M+H)$^+$.

Example 17B (1S,4S)-2-(3-pyridinyl)-2,5-diazabicyclo[2.2.1]heptane 4-methylbenzenesulfonate The product from Example 17A was processed as described in Example 1 B to provide the title compound (65% yield). $^1$H NMR (CDCl$_3$, free base, 300 MHz) δ 1.82-1.98 (m, 2H), 3.01 (d, J=12.0 Hz, 1H), 3.08 (s, 2H), 3.67 (dd, J=2.0, 11.5 Hz, 1H), 3.76 (s, 1H), 4.32 (s, 1H), 6.78-6.85 (m, 1H), 7.05-7.13 (m, 1H), 7.82-8.01 (m, 2H); MS (DCI/$NH_3$) m/z 176 (M+H)$^+$, 193 (M+$NH_4$)$^+$; Anal. Calcd. for $C_{10}H_{13}N_3·1.0$ TsOH·$0.4H_2O$: C, 57.58; H, 6.20; N, 11.85. Found: C, 57.85; H, 6.33; N, 11.47.

EXAMPLE 18

(1S,4S)-2-(5-chloro-2-pyridinyl)-2,5-diazabicyclo [2.2.1]heptane dihydrochloride

Example 18A tert-butyl (1S,4S)-5-(5-chloro-2-pyridinyl)-2,5-diazabicyclo[2.2.1]heptane-2-carboxylate tert-Butyl (1S,4S)-2,5-diazabicyclo[2.2.1]heptane-2-carboxylate, prepared as described in (J. Med. Chem., (1988) 31, 1598-1611), and commercially available 2,5-dichloropyridine were processed as described in Example 2A to provide the title compound (99% yield).

Example 18B (1S,4S)-2-(5-chloro-2-pyridinyl)-2,5-diazabicyclo [2.2.1]heptane dihydrochloride The product from Example 18A was treated with HCl in ether to afford the dihydrochloride salt. $^1$H NMR (DMSO-$d_6$, 300 MHz) δ 2.00 (m,2H), 3.2-3.3 (m,4H), 4.6-4.8 (m, 2H) 6.80 (d, J=7.4 Hz, 1H), 7.8 (dd, J=7.5, 3.1 Hz, 1H), 8.2 (d, J=3.1 Hz, 1H), 9.2 (br. s, 1H), 9.8 (br. s., 1H); MS (DCI/$NH_3$) m/z 210, 212 (M+H)$^+$.

EXAMPLE 19

3-(5-chloro-2-pyridinyl)-3,8-diazabicyclo[3.2.1] octane dihydrochloride

Example 19A tert-butyl 3-(5-chloro-2-pyridinyl)-3,8-diazabicyclo [3.2.1]octane-8-carboxylate tert-Butyl 3,8-diazabicyclo[3.2.1]octane-8-carboxylate, prepared as described in (J. Med. Chem., (1998) 41, 674), and 2,5-dichloropyridine were processed as described in Example 10A to provide the title compound.

Example 19B

3-(5-chloro-2-pyridinyl)-3,8-diazabicyclo[3.2.1]octane dihydrochloride

The product from Example 19A was processed as described in Example 10B to provide the title compound. $^1$H NMR (DMSO-$d_6$, 300 MHz) δ 1.9-2.0 (m, 4H), 3.2 (d, J=11 Hz, 2H), 4.0-4.2 (m, 4H), 7.0 (d, J=7.1 Hz, 1H), 7.8 (dd, J=7.5, 3.1 Hz, 1H), 8.2 (d, J=3.1 Hz, 1H), 9.4 (br. s. 2H); MS (DCI/NH$_3$) m/z 224, 226 (M+H)$^+$.

EXAMPLE 20

(1R,4R)-2-(3-pyridinylmethyl)-2,5-diazabicyclo[2.2.1]heptane trihydrobromide

Example 20A

(1R,4R)-2-[(4-methylphenyl)sulfonyl]-5-(3-pyridinylmethyl)-2,5-diazabicyclo[2.2.1]heptane ((2R,4S)-1-[(4-Methylphenyl)sulfonyl]-4-{[(4-methylphenyl)sulfonyl]oxy}pyrrolidinyl)methyl 4-methylbenzenesulfonate (1.5 g, 2.6 mmol), prepared as described in (J. Med. Chem. (1990) 33, 1344) and 3-(aminomethyl)pyridine (1.0 g, 9.3 mmol) in 20 mL of toluene were heated under reflux for 16 hours. The mixture was cooled, filtered, and the filter cake was washed with 20 mL of toluene. The filtrate was concentrated under reduced pressure and the residue was purified by chromatography (silica gel; hexanes:EtOAc, 9:1 to 1:1) to provide the title compound (410 mg, 46%). $^1$H NMR (DMSO-$d_6$, 300 MHz) δ 0.86 (d, J=8.5 Hz, 1H), 1.62 (d, J=9.7 Hz, 1H), 2.42 (s, 3H), 2.44 (m, 1H), 2.66 (dd, J=2.4, 9.5 Hz, 1H), 2.99 (dd, J=2.0, 9.5 Hz, 1H), 3.39-3.48 (m, 2H), 3.62-3.41 (d, J=9.5 Hz, 1H), 4.23 (br s, 1H), 4.35 (t, J=5.1 Hz, 1H), 7.31 (m, 1H), 7.43-7.46 (m, 2H), 7.62 (m, 1H), 7.71-7.74 (m, 2H), 8.31-8.43 (m, 2H).

Example 20B

(1R,4R)-2-(3-pyridinylmethyl)-2,5-diazabicyclo[2.2.1]heptane trihydrobromide The product from Example 20A (320 mg, 0.9 mmol) in acetic acid (3.4 mL) and 33% HBr/acetic acid (7 mL) was heated to 70° C. for 18 hours. After cooling to ambient temperature, the precipitate was filtered, washed with ether, and dried. The resulting solids were recrystallized from EtOH/EtOAc to provide the title compound (332 mg, 80%). $^1$H NMR (DMSO-$d_6$, 300 MHz) δ 2.22 (m, 1H), 2.47 (m, 1H), 3.29-3.48 (m, 2H), 3.35 (m, 1H), 3.69 (m, 1H), 4.19-4.53 (m, 2H), 5.59 (m, 2H), 8.05 (m, 1H), 8.62 (m, 1H), 8.78-8.88 (m, 2H); MS (DCI/NH$_3$) m/z 190 (M+H)$^+$; Anal. Calcd. for $C_{11}H_{15}N_3$·3.0 HBr·0.1H$_2$O: C, 30.46; H, 4.23; N, 9.69. Found: C, 30.83; H, 4.25; N, 9.30.

EXAMPLE 21

(1S,4S)-2-[5-(benzyloxy)-3-pyridinyl]-2,5-diazabicyclo[2.2.1]heptane 4-methylbenzenesulfonate

Example 21A tert-butyl (1S,4S)-5-[5-(benzyloxy)-3-pyridinyl]-2,5-diazabicyclo[2.2.1]heptane-2-carboxylate tert-Butyl (1S,4S)-2,5-diazabicyclo[2.2.1]heptane-2-carboxylate, prepared as described in (J. Med. Chem., (1988) 31, 1598-1611) and 3-(benzyloxy)-5-bromopyridine, prepared as described in (U.S. Pat. No. 5,733,912) were coupled according to the procedure described in Example 1A to provide the title compound. MS (DCI/NH$_3$) m/z 382 (M+H)$^+$.

Example 21B

(1S,4S)-2-[5-(benzyloxy)-3-pyridinyl]-2,5-diazabicyclo[2.2.1]heptane 4-methylbenzenesulfonate The product of Example 21A was processed as described in Example 2B to provide the title compound. $^1$H NMR (CDCl$_3$, 300 MHz) δ 1.78-2.00 (m, 4H), 2.97 (d, J=12.0 Hz, 1H), 3.05 (s, 2H), 3.62 (dd, J=3.0, 10.0 Hz, 1H), 3.81 (s, 1H), 4.28 (s, 1H), 6.42 (dd, J=2.0, 8.0 Hz, 1H), 7.31-7.51 (m, 5H), 7.65 (d, J=3.0 Hz, 1H), 7.78 (d, J=3.0 Hz, 1H); MS (DCI/NH$_3$) m/z 282 (M+H)$^+$; Anal. calculated for $C_{24}H_{27}N_3O_4S$·0.30 TsOH·0.55H$_2$O: C, 60.86; H, 5.97; N, 8.16. Found: C, 60.83; H, 6.00; N, 8.12.

EXAMPLE 22

(1S,4S)-2-[5-hydroxy-3-pyridinyl]-2,5-diazabicyclo[2.2.1]heptane 4-methylbenzenesulfonate

Example 22A tert-butyl (1S,4S)-5-(5-hydroxy-3-pyridinyl)-2,5-diazabicyclo[2.2.1]heptane-2-carboxylate The product from Example 21A (0.50 g, 1.31 mmol) in EtOH (15 mL) was treated with 10%Pd/C (0.02 g) under a hydrogen atmosphere (1 atm) at 40° C. for 6 hours. The reaction mixture was allowed to cool to ambient temperature and the catalyst was removed by filtration. The filtrate was diluted with diethyl ether (125 mL), washed with brine, dried (MgSO$_4$), and concentrated under reduced pressure. The residue was purified by chromatography on SiO$_2$ (5% MeOH/CH$_2$Cl$_2$) to provide the title compound (0.345 g, 90% yield) as a yellow oil. MS (DCI/NH$_3$) m/z 292 (M+H)$^+$.

Example 22B

(1S,4S)-2-[5-hydroxy-3-pyridinyl]-2,5-diazabicyclo[2.2.1]heptane 4-methylbenzenesulfonate The product from Example 22A was processed as described in Example 2B to provide the title compound. $^1$H NMR (MeOD, 300 MHz) δ 2.07 (d, J=12.0 Hz, 1H), 2.28 (d, J=13.0 Hz, 1H), 3.32-3.42 (m, 3H), 3.71 (dd, J=4.0, 10.0 Hz, 1H), 4.51 (s, 1H), 4.68 (s, 1H), 6.62 (t, J=2.0 Hz, 1H), 7.51-7.56 (m, 2H); MS (DCI/NH$_3$) m/z 192 (M+H)$^+$; Anal. calculated for $C_{17}H_{21}N_3O_4S$·0.55 TsOH·2.35H$_2$O: C, 50.04; H, 6.06; N, 8.40. Found: C, 50.09; H, 6.35; N, 8.38.

EXAMPLE 23

(1S,4S)-2-(6-methyl-3-pyridinyl)-2,5-diazabicyclo[2.2.1]heptane 4-methylbenzenesulfonate

Example 23A tert-butyl (1S,4S)-5-(6-methyl-3-pyridinyl)-2,5-diazabicyclo[2.2.1]heptane-2-carboxylate tert-Butyl (1S,4S)-2,5-diazabicyclo [2.2.1]heptane-2-carboxylate, prepared as described in (J. Med. Chem., (1988)

31, 1598-1611), and 5-bromo-2-methyl-pyridine (purchased from Emka Chemie) were coupled according to the procedure described in Example 1A to provide the title product. MS (DCI/NH$_3$) m/z 290 (M+H)$^+$.

Example 23B (1S,4S)-2-(6-methyl-3-pyridinyl)-2,5-diazabicyclo [2.2.1]heptane 4-methylbenzenesulfonate The product from Example 23A was processed as described in Example 2B to provide the title compound. $^1$H NMR (CDCl$_3$, 300 MHz) δ 1.84 (d, J=9.0 Hz, 1H), 1.93 (d, J=9.0 Hz, 1H), 2.42 (s, 3H), 2.92 (d, J=7.0 Hz, 1H), 3.03-3.10 (m, 2H), 3.65 (dd, J=2.0, 6.0 Hz, 1H), 3.78 (s, 1H), 4.28 (s, 1H), 6.78 (dd, J=4.0, 7.0 Hz, 1H), 6.97 (d, J=4.0 Hz, 1H), 7.85 (d, J=2.0 Hz, 1H); MS (DCI/NH$_3$) m/z 190 (M+H)$^+$; Anal. calculated for C$_{18}$H$_{23}$N$_3$O$_3$S.0.5 TsOH.0.5H$_2$O: C, 56.56; H, 6.18; N, 9.20. Found: C, 56.57; H, 6.03; N, 9.28.

EXAMPLE 24

(1R,4R)-2-(3-pyridinyl)-2,5-diazabicyclo[2.2.1]heptane 4-methylbenzenesulfonate

Example 24A tert-butyl (1R,4R)-5-(3-pyridinyl)-2,5-diazabicyclo [2.2.1]heptane-2-carboxylate The product from Example 15B and 3-bromopyridine (available from Aldrich Chemical Co.) were coupled according to the procedure described in Example 15C to provide the title compound. MS (DCI/NH$_3$) m/z 276 (M+H)$^+$.

Example 24B (1R,4R)-2-(3-pyridinyl)-2,5-diazabicyclo[2.2.1]heptane 4-methylbenzenesulfonate The product from Example 24A was processed as described in Example 2B to provide the title compound. $^1$H NMR (CDCl$_3$, 300 MHz) δ 1.90 (dd, J=12.0, 30.0 Hz, 2H), 2.98 (d, J=9.0 Hz, 1H), 3.08 (s, 2H), 3.63 (dd, J=3.0, 10.0 Hz, 1H), 3.82 (s, 1H), 4.32 (s, 1H), 6.78-6.84 (m, 1H), 7.08-7.15 (m, 1H), 7.95 (dd, 2.0, 8.0 Hz, 1H), 8.00 (d, J=3.0 Hz, 1H); MS (DCI/NH$_3$) m/z 176 (M+H)$^+$; Anal. calculated for C$_{17}$H$_{21}$N$_3$O$_3$S.0.45H$_2$O: C, 57.43; H, 6.21; N, 11.82. Found: C, 57.64; H, 6.11; N, 11.43.

EXAMPLE 25

(1R,4R)-2-(3-pyridazinyl)-2,5-diazabicyclo[2.2.1] heptane 4-methylbenzenesulfonate Example 25A tert-butyl (1R,4R)-5-(3-pyridazinyl)-2,5-diazabicyclo[2.2.1]heptane-2-carboxylate The product from Example 16A was process according to the procedure described in Example 29A to provide the title compound. MS (DCI/NH$_3$) m/z 277 (M+H)$^+$.

Example 25B (1R,4R)-2-(3-pyridazinyl)-2,5-diazabicyclo[2.2.1] heptane 4-methylbenzenesulfonate The product from Example 25A was processed as described in Example 2B to provide the title compound. $^1$H NMR (MeOH, 300 MHz) δ 2.11 (d, J=12.0 Hz, 1H), 2.26-2.39 (m, 3H), 3.65-3.82 (m, 2H), 4.60 (s, 1H), 5.09 (s, 1H), 7.30 (dd, J=1.0, 9.0 Hz, 1H), 7.57-7.65 (m, 1H), 8.56 (dd, J=1.0, 6.0 Hz, 1H); MS (DCI/NH$_3$) m/z 176 (M+H)$^+$; Anal. calculated for C$_{16}$H$_{20}$N$_4$O$_3$S.0.25 TsOH.0.85H$_2$O: C, 52.41; H, 5.87; N, 13.77. Found: C, 52.45; H, 5.88; N, 13.69.

EXAMPLE 27

(1R,4R)-2-(6-chloro-3-pyridinyl)-5-cyanomethyl-2, 5-diazabicyclo[2.2.1]heptane 4-methylbenzene-sulfonate The product from Example 15D (140 mg, 0.37 mmole) in DMF (5 mL) was treated with triethylamine (0.26 mL, 1.8 mmole) and bromoacetonitrile (0.03 mL, 0.43 mmole) under a nitrogen atmosphere. After stirring for 72 hours at ambient temperature, the reaction mixture was poured into saturated aqueous Na$_2$CO$_3$ (30 mL) and extracted with ether (5×50 mL). The organic phase was dried (MgSO$_4$) and concentrated under reduced pressure. The residue was purified on SiO$_2$ (CHCl$_3$/MeOH/NH$_4$OH 95:4.5:0.5) and combined with 4-methylbenzenesulfonic acid (21 mg, 0.11 mmole) to provide the title compound (47 mg, 30% yield). $^1$H NMR (D$_2$O, 300 MHz) δ 2.14 (m, 2H), 2.39 (s, 3H), 3.34-3.48 (m, 2H), 3.36 (d, J=9.03 Hz 1H), 3.62 (m, 1H), 3.93-3.95 (m, 2H), 4.10 (br s, 1H), 4.52 (br s, 1H), 7.17 (dd, J=2.84, 7.72 Hz, 1H) 7.28-7.38 (m, 3H), 7.69 (d, J=8.11 Hz, 2H)7.77 (d, J=2.94 Hz, 1H); MS (DCI/NH$_3$) m/z 249 (M+H)$^+$, 266 (M+NH$_4$)$^+$; Anal calculated for C$_{12}$H$_{13}$N$_4$Cl.C$_7$H$_8$O$_3$ S.0.1H$_2$O: C, 53.99; H, 5.05; N, 13.25. Found: C, 53.99; H, 5.19; N, 13.19.

EXAMPLE 28

(1S,4S)-2-(6-nitro-3-pyridinyl)-2,5-diazabicyclo [2.2.1]heptane

The product from Example 3A was treated with trifluoroacetic acid:methylene chloride (1:2) at ambient temperature for 2 hours. The volatiles were removed under reduced pressure, and the residue was purified on SiO$_2$ (5% MeOH/CH$_2$Cl$_2$/1%NH$_4$OH) to provide the title compound as a yellow gum. MS (DCI/NH$_3$) m/z 221 (M+H)$^+$, 238 (M+NH$_4$)$^+$.

EXAMPLE 29

(1S,4S)-2-(3-pyridazinyl)-2,5-diazabicyclo[2.2.1] heptane 4-methylbenzenesulfonate Example 29A tert-butyl (1S,4S)-5-(3-pyridazinyl)-2,5-diazabicyclo [2.2.1]heptane-2-carboxylate The product from Example 2A (0.885 g, 2.85 mmol) in MeOH (14 mL) and triethylamine (0.55 mL) was treated with 10% Pd/C (0.02 g) and stirred under a hydrogen atmosphere (60 psi) at 50° C. for 80 minutes. The catayst was removed by filtration and the filtrate was concentrated. The residue was purified on $SiO_2$ (5% $MeOH/CH_2Cl_2$) to provide the title compound (0.72 g, 92%) as a white solid. MS ($DCI/NH_3$) m/z 276 $(M+H)^+$.

Example 29B

(1S,4S)-2-(3-pyridazinyl)-2,5-diazabicyclo[2.2.1]heptane 4-methylbenzenesulfonate The product from Example 29A was processed as described in Example 2B to provide the title compound. $^1H$ NMR (MeOH, 300 MHz) δ 2.13 (d, J=13.0 Hz, 1H), 2.28-2.40 (m, 3H), 3.68-3.87 (m, 2H), 4.62 (s, 1H), 5.11 (s, 1H), 7.36 (dd, J=1.0, 9.0 Hz, 1H), 7.60-7.68 (m, 1H), 8.60 (dd, J=1.0, 5.0 Hz, 1H); MS ($DCI/NH_3$) m/z 176 $(M+H)^+$; Anal. calculated for $C_{16}H_{20}N_4O_3S.0.25$ $TsOH.0.85H_2O$: C, 52.34; H, 5.85; N, 13.49. Found: C, 52.29; H, 6.03; N, 13.52.

EXAMPLE 30

(1S,4S)-2-(6-fluoro-3-pyridinyl)-2,5-diazabicyclo[2.2.1]heptane bis(4-methylbenzenesulfonate)

Example 30A tert-butyl (1S,4S)-5-(6-fluoro-3-pyridinyl)-2,5-diazabicyclo[2.2.1]heptane-2-carboxylate tert-Butyl (1S,4S)-2,5-diazabicyclo[2.2.1]heptane-2-carboxylate (0.300 g, 1.01 mmol), prepared as described in (J. Med. Chem., (1988) 31, 1598-1611), in anhydrous toluene (30 ml) was treated with 2-fluoro-5-iodopyridine (0.34 g, 1.52 mmol), available as described in (U.S. Pat. No. 5,733, 912), $Pd_2(dba)_3$ (0.028 g, 0.03 mmol), (S)-(-)-2-(diphenylphosphino)-2'-methoxy-1,1'-binaphthyl (0.028 g, 0.06 mmol), available from Strem Chemicals, and sodium tert-butoxide (0.248 g, 2.58 mmol). The reaction mixture was heated at 80° C. for 5 hours. The reaction mixture was poured into diethyl ether (100 mL), washed with brine (100 ml), dried ($MgSO_4$), and concentrated under reduced pressure. The residue was purified by chromatography on $SiO_2$ (3% $MeOH/CH_2Cl_2$) to provide the title compound (0.095 g, 21% yield) as a yellow oil. MS ($DCI/NH_3$) m/z 276 $(M+H)^+$.

Example 30B

(1S,4S)-2-(6-fluoro-3-pyridinyl)-2,5-diazabicyclo[2.2.1]heptane bis(4-methylbenzenesulfonate)

The product from Example 30A was processed as described in Example 2B to provide the title compound. $^1H$ NMR (MeOD, 300 MHz) δ 2.06 (d, J=12.0 Hz, 1H), 2.29 (d, J=12.0 Hz, 1H), 3.25-3.30 (m, 1H). 3.35 (s, 2H), 3.73 (dd, J=3.0, 12.0 Hz, 1H), 4.50 (s, 1H), 4.68 (3, 1H), 6.96 (dd, J=3.0, 9.0 Hz, 1H), 7.28-7.38 (m, 1H), 7.52-7.54 (m, 1H); MS ($DCI/NH_3$) m/z 194 $(M+H)^+$; Anal. calculated for $C_{24}H_{28}N_3O_6S_2F.0.75$ $TsOH.1.15H_2O$: C, 51.10; H, 5.32; N, 6.11. Found: C, 51.11; H, 5.54; N, 6.10.

EXAMPLE 31

(1S,4S)-2-(5-bromo-3-pyridinyl)-2,5-diazabicyclo[2.2.1]heptane 4-methylbenzenesulfonate

Example 31A tert-butyl (1S,4S)-5-(5-bromo-3-pyridinyl)-2,5-diazabicyclo[2.2.1]heptane-2-carboxylate tert-Butyl (1S,4S)-2,5-diazabicyclo [2.2.1]heptane-2-carboxylate, prepared as described in (J. Med. Chem., (1988) 31, 1598-1611), and 3,5-dibromopyridine (purchased from Avocado Research Chemicals, Ltd.) were coupled according to the procedure described in Example 1A to provide the title compound. MS ($DCI/NH_3$) m/z 354 $(M+H)^+$.

Example 31B

(1S,4S)-2-(5-bromo-3-pyridinyl)-2,5-diazabicyclo[2.2.1]heptane 4-methylbenzenesulfonate The product of Example 31 A was processed as described in Example 2B to provide the title compound. $^1H$ NMR ($CDCl_3$, 300 MHz) δ 1.92-2.10 (m, 2H), 3.21 (s, 2H), 3.60-3.71 (m, 2H), 4.05 (s, 1H), 4.38 (s, 1H), 6.97 (t, J=1.0 Hz, 1H), 7.90 (d, J=2.0 Hz, 1H), 8.03 (d, J=1.0 Hz, 1H); MS ($DCI/NH_3$) m/z 254 $(M+H)^+$; Anal. calculated for $C_{17}H_{20}N_3O_3SBr.0.30$ TsOH: C, 47.99; H, 4.72; N, 8.79. Found: C, 48.02; H, 4.95; N, 8.87.

EXAMPLE 32

(1S,4S)-2-(5-cyano-3-pyridinyl)-2,5-diazabicyclo[2.2.1]heptane 4-methylbenzenesulfonate

Example 32A tert-butyl (1S,4S)-5-(5-cyano-3-pyridinyl)-2,5-diazabicyclo[2.2.1]heptane-2-carboxylate The product of Example 31A (2.89 g, 8.2 mmol) in anhydrous/degassed DMF (60 ml) was treated with $Zn(CN)_2$ (0.481 g, 4.1 mmol), and tetrakis(triphenylphosphine)palladium(0) (0.95 g, 0.8 mmol). The mixture was heated at 80° C. for 16 hours under a nitrogen atmosphere. The reaction mixture was allowed to cool to ambient temperature and poured into diethyl ether (150 ml). The organics were washed with brine/$H_2O$ (1/1) (200 ml), dried ($MgSO_4$), and concentrated under reduced pressure. The residue was purified on $SiO_2$ (5% $MeOH/CH_2Cl_2$) to provide the title compound (1.90 g, 77% yield) as a white solid. MS ($DCI/NH_3$) m/z 301 $(M+H)^+$.

Example 32B

(1S,4S)-2-(5-cyano-3-pyridinyl)-2,5-diazabicyclo[2.2.1]heptane 4-methylbenzenesulfonate The product from Example 32A was processed as described in Example 2B to provide the title compound. $^1H$ NMR (MeOD, 300 MHz) δ 2.0 (d, J=13.0 Hz, 1H), 2.21 (d, J=13.0 Hz, 1H), 3.38 (s, 2H), 3.42 (d, J=1.0 Hz, 1H), 3.75 (dd, J=3.0, 12.0 Hz, 1H), 4.56 (s, 1H), 4.82 (s, 1H), 7.48 (t, J=1.0 Hz, 1H), 8.19-8.31 (m, 2H); MS ($DCI/NH_3$) m/z 201 $(M+H)^+$; Anal. calculated for $C_{18}H_{20}N_4O_3S$: C, 58.05; H, 5.41; N, 15.04. Found: C, 57.84; H, 5.47; N, 14.81.

EXAMPLE 33

(1R,4R)-2-(6-fluoro-3-pyridinyl)-2,5-diazabicyclo [2.2.1]heptane 4-methylbenzenesulfonate

Example 33A tert-butyl (1R,4R)-5-(6-fluoro-3-pyridinyl)-2,5-diazabicyclo[2.2.1]heptane-2-carboxylate The product from Example 15B and 2-fluoro-5-iodopyridine were processed as described in Example 30A to provide the title compound. MS (DCI/NH$_3$) m/z 294 (M+H)$^+$.

Example 33B (1R,4R)-2-(6-fluoro-3-pyridinyl)-2,5-diazabicyclo [2.2.1]heptane 4-methylbenzenesulfonate The product of Example 33A was processed as described in Example 2B to provide the title compound. $^1$H NMR (CDCl$_3$, 300 MHz) δ 1.75 (d, J=12.0 Hz, 1H), 1.96 (d, J=12.0 Hz, 1H), 2.92 (d, J=9.0 Hz, 1H), 3.07 (s, 2H), 3.66 (dd, J=3.0, 9.0 Hz, 1H), 3.81 (s, 1H), 4.26 (s, 1H), 6.78 (dd, J=1.0, 6.0 Hz, 1H), 6.92-7.0 (m, 1H), 7.45 (t, J=1.0 Hz, 1H); MS (DCI/NH$_3$) m/z 194 (M+H)$^+$, 211 (M+NH$_4$)$^+$; Anal. calculated for C$_{17}$H$_{20}$N$_3$O$_3$SF: C, 55.20; H, 5.59; N, 11.36. Found: C, 55.21; H, 5.61; N, 11.13.

EXAMPLE 34

(1S,4S)-2-(5-aminomethyl-3-pyridinyl)-2,5-diazabicyclo[2.2.1]heptane trihydrochloride

Example 34A tert-butyl (1S,4S)-5-(5-aminomethyl-3-pyridinyl)-2, 5-diazabicyclo [2.2.1]heptane-2-carboxylate The product from Example 32A (0.267 g, 0.89 mmol) in 30% NH$_3$/methanol was treated with Raney-Nickel (0.1 Og). The reaction mixture was stirred at ambient temperature under a hydrogen atmosphere (60 psi) for 4 hours. The mixture was filtered and concentrated under reduced pressure. The residue was purified by chromatography (SiO$_2$; 10% MeOH/CH$_2$Cl$_2$/1% NH$_4$OH) to provide the title compound (0.199 g, 73% yield) as a white solid. MS (DCI/NH$_3$) m/z 305 (M+H)$^+$.

Example 34B (1S,4S)-2-(5-aminomethyl-3-pyridinyl)-2,5-diazabicyclo[2.2.1]heptane trihydrochloride The product from Example 34A (0.199 g, 0.65 mmol) in EtOH (5 mL) was treated with 4N HCl/dioxane (5 mL). After stirring at ambient temperature for 1 hour, the volatiles were removed under reduced pressure to provide the title compound (0.042 g, 20% yield) as a white solid. $^1$H NMR (CDCl$_3$, 300 MHz) δ 2.18 (d, J=12.0 Hz, 1H), 2.34 (d, J=12.0 Hz, 1H), 3.45-3.58 (m, 3H), 3.83 (d, J=15.0 Hz, 1H), 4.32 (s, 2H), 4.68 (s, 1H), 4.89 (s, 1H), 7.68 (s, 1H), 8.11 (s, 1H), 8.15 (s, 1H); MS (DCI/NH$_3$) m/z 205 (M+H)$^+$; Anal. calculated for C$_{11}$H$_{16}$N$_4$.3.6 HCl.0.45 EtOH: C, 40.12; H, 6.31; N, 15.73. Found: C, 40.22; H, 6.20; N, 15.72.

EXAMPLE 35

2-(6-chloro-3-pyridinyl)-2,6-diazabicyclo[3.2.1] octane trihydrochloride

Example 35A benzyl 3-oxo-2,6-diazabicyclo[3.2.1]octane-6-carboxylate

Benzyl 5-oxo-2-azabicyclo[2.2.1]heptane-2-carboxylate (2.46 g, 10.0 mmol), prepared according to the procedures described by (Carroll, F. I.; et. al., J. Med. Chem. (1992) 35, 2184), in 50 mL of 95% aqueous ethanol at ambient temperature was treated with sodium acetate (2.47 g, 30.1 mmol) and hydroxylamine hydrochloride (3.48 g, 50.1 mmol). After 45 minutes, the mixture was concentrated under reduced pressure and the residue was diluted with saturated aqueous NaHCO$_3$ and extracted with EtOAc. The organic extract was dried (MgSO$_4$) and concentrated to afford 2.50 grams (96%) of a mixture of the desired oximes as a white solid. A portion of this material (1.57 g, 6.03 mmol) was stirred in a 5:1 solution of CH$_2$Cl$_2$/trimethylsilylpolyphosphate for 12 hours at ambient temperature. The solution was diluted with H$_2$O and extracted twice with EtOAc. The combined organic extracts were dried (MgSO$_4$) and concentrated under reduced pressure. The residue was purified by chromatography (silica gel; 95:5 CH$_2$Cl$_2$/ MeOH) to provide 1.08 grams (68%) of the title compound as a white solid. MS (DCI/NH$_3$) m/z 261 (M+H)$^+$, 278 (M+NH$_4$)$^+$.

Example 35B benzyl 2,6-diazabicyclo[3.2.1]octane-6-carboxylate

The product from example 35A (800 mg, 3.07 mmol) in THF (12 mL) at 0° C. was treated dropwise with a 2.0 M solution of borane-methyl sulfide complex in THF (3.4 mL, 6.8 mmol). The solution was stirred for 14 hours at ambient temperature, then recooled to 0° C. and quenched by the careful addition of MeOH and concentrated under reduced pressure. The residue was dissolved in toluene (12 mL) and treated with n-propylamine (1.7 mL). The mixture was stirred for 3 hours at 60° C., allowed to cool to ambient temperature, and concentrated under reduced pressure. The residue was diluted with saturated aqueous NaHCO$_3$ and extracted with CH$_2$Cl$_2$ (4×). The organic extracts were combined, dried (K$_2$CO$_3$), and concentrated. The residue was purified by chromatography (silica gel; 90:10:1 CH$_2$Cl$_2$/MeOH/NH$_4$OH) to provide 453 mg (60%) of the title compound as a colorless oil. MS (DCI/NH$_3$) m/z 247 (M+H)$^+$.

Example 35C benzyl 2-(6-chloro-3-pyridinyl)-2,6-diazabicyclo [3.2.1]octane-6-carboxylate The product from Example 35B and 2-chloro-5-iodopyridine were processed as described in Example 1A to provide the title compound (30% yield) as a light yellow oil. MS (DCI/NH$_3$) m/z 358, 360 (M+H)$^+$.

Example 35D

2-(6-chloro-3-pyridinyl)-2,6-diazabicyclo[3.2.1]octane trihydrochloride

The product from Example 35C (62 mg, 0.17 mmol) in acetonitrile (3 mL) at 0° C. was treated with iodotrimethylsilane (37 mL, 0.26 mmol). The solution was stirred at 0° C. for 3 hours, quenched with MeOH, and concentrated under reduced pressure. The residue was diluted with 1N aqueous HCl and extracted with EtOAc (2×). The aqueous phase was basified with 10% aqueous NaOH and extracted with 3:1 $CH_2Cl_2$/iPrOH (4×). The extracts were combined, dried ($K_2CO_3$), and concentrated to provide a light yellow oil. The oil was diluted with EtOH and treated with a solution of HCl in diethyl ether. The resulting precipitate was collected, triturated with diethyl ether, and dried under high vacuum to provide the title compound as a light yellow solid. $^1$H NMR (DMSO-$d_6$, 300 Hz) δ 1.80-2.02 (m, 4H), 3.00 (m, 1H), 3.34-3.40 (m, 2H), 3.60 (m, 1H), 4.15 (m, 1H), 4.68 (m, 1H), 7.33 (d, J=8.8 Hz, 1H), 7.43 (dd, J=3.3, 8.8 Hz, 1H), 8.08 (d, J=3.0 Hz, 1H); MS (CI/$NH_3$) m/z 224, 226 (M+H)$^+$; Anal. Calcd. for $C_{11}H_{14}ClN_3$.3 HCl.1.2$H_2O$: C, 37.25; H, 5.51; N, 11.85. Found: C, 36.99; H, 5.21; N, 12.13.

EXAMPLE 36

3-(6-chloro-3-pyridinyl)-3,9-diazabicyclo[4.2.1]nonane hydrochloride

The product from Example 37A (1.15 g, 4.6 mmol) in chloroform (10 mL) was treated with α-chloroethyl chloroformate (1.1 eq.) at 0° C. The solution was allowed to warm to ambient temperature over 0.5 hours and then heated at reflux for one hour. The mixture was allowed to cool to ambient temperature and concentrated under reduced pressure. The residue was dissolved in methanol (20 mL) and heated at reflux for one hour. The solvent was removed under reduced pressure to provide a solid that was recrystallized from ethanol to provide the title compound (1.03 g, 83% yield). $^1$H NMR (CD$_3$OD, 300 MHz) δ 1.72-1.84 (m, 1H), 1.87-2.0 (m, 1H), 2.0-2.36 (m, 4H), 3.5-3.65 (m, 2H), 3.65-3.78 (m, 1H), 3.8-3.9 (br d, J=15 Hz, 1H), 4.22 (br s, 2H), 7.25 (d, J=12 Hz, 1H), 7.38 (dd, J=4.5, 12 Hz, 1H), 7.97 (d, J=4.5 Hz, 1H); MS (DCI/NH$_3$) m/z 238 (M+H)$^+$, 255 (M+NH$_4$)$^+$; Anal. Calcd. for $C_{12}H_{16}ClN_3$.HCl: C, 52.57; H, 6.25; N, 15.32. Found: C, 52.82; H, 6.33; N, 15.32.

EXAMPLE 37

9-methyl-3-(3-pyridinyl)-3,9-diazabicyclo[4.2.1]nonane 4-methylbenzenesulfonate

Example 37A

9-methyl-3-(6-chloro-3-pyridinyl)-3,9-diazabicyclo[4.2.1]nonane

9-Methyl-3,9-diazabicyclo[4.2.1]nonane (prepared as described in U.S. Pat. No. 2,999,091) and 2-chloro-5-iodopyridine were coupled according the procedure of Example 15C to provide the title compound (78% yield). $^1$H NMR (free base, CDCl$_3$, 300 MHz) δ 1.23-1.48 (m, 2H), 1.65-1.76 (m, 1H), 1.91-2.27 (m, 3H), 2.44 (s, 3H), 3.18-3.35 (m, 3H), 3.48-3.54 (m, 2H), 3.65 (br d, J=13.5 Hz, 1H), 6.98 (dd, J=3, 8.25 Hz, 1H), 7.06 (d, J=8.25 Hz, 1H), 7.87 (d, J=3 Hz, 1H); MS (DCI/NH$_3$) m/z 252 (M+H)$^+$, 269 (M+NH$_4$)$^+$; Anal. Calcd. for $C_{13}H_{18}ClN_3$.$C_7H_8O_3S$: C, 56.66; H, 6.18; N, 9.91. Found: C, 56.76; H, 6.15; N, 9.77.

Example 37B

9-methyl-3-(3-pyridinyl)-3,9-diazabicyclo[4.2.1]nonane 4-methylbenzenesulfonate The product from Example 37A (641 mg), was treated with 10% Pd/C (61.8 mg) in methanol (11 mL) and triethyl amine (0.64 mL) under a hydrogen atmosphere (60 psi) at 50° C. for one hour. The mixture was filtered and concentrated under reduced pressure to provide a solid. The resulting solid was taken up in EtOAc and washed with saturated NaHCO$_3$ and brine. The organic phase was dried (MgSO$_4$) and concentrated under reduced pressure to provide the free base (91% yield). The free base was treated with 4-methylbenzenesulfonate (1.0 eq) and the obtained solid was recrystallized from ethanol/ethyl acetate. $^1$H NMR (CD$_3$OD, 300 MHz) δ 1.83-1.93 (m, 1H), 1.93-2.11 (m, 2H), 2.15-2.29 (m, 1H), 2.37 (s, 3H), 2.44-2.56 (m, 2H), 2.95 (s, 3H), 3.61-3.82 (m, 4H), 4.02-4.15 (m, 2H), 7.23 (d, J=7.5 Hz, 2H), 7.29 (dd, J=4.5, 7.5 Hz, 1H), 7.69 (d, J=7.5 Hz, 2H), 7.94 (dd, J=1.5, 4.5 Hz, 1H), 8.2 (d, J=3 Hz, 1H); MS (DCI/NH$_3$) m/z 218 (M+H)$^+$, 235 (M+NH$_4$)$^+$; Anal. Calcd. for $C_{13}H_{19}N_3$.$C_7H_8O_3S$: C, 61.67; H, 6.99; N, 10.79. Found: C, 61.50; H, 7.03; N, 10.76.

EXAMPLE 38

(1S,4S)-2-(5-aminocarbonyl-3-pyridinyl)-2,5-diazabicyclo[2.2.1]heptane bis(4-methylbenzenesulfonate)

Example 38A tert-butyl (1S,4S)-5-(5-aminocarbonyl-3-pyridinyl)-2,5-diazabicyclo[2.2.1]heptane-2-carboxylate The product of Example 32A (0.43 g, 1.43 mmol) in ethanol (20 mL) was treated with 30% $H_2O_2$ (1.40 mL) and 6N NaOH (1.40 mL) and heated at 50° C. for 2 hours. The mixture was poured into 15% NaOH (50 mL) and extracted with $CH_2Cl_2$ (150 mL). The organic phase was dried (MgSO$_4$) and concentrated under reduced pressure. The residue was purified on SiO$_2$ (5% MeOH/$CH_2Cl_2$) to provide the title compound (0.20 g, 44%) as a white solid. MS (DCI/NH$_3$) m/z 319 (M+H)$^+$.

Example 38B

(1S,4S)-2-(5-aminocarbonyl-3-pyridinyl)-2,5-diazabicyclo[2.2.1]heptane bis(4-methylbenzenesulfonate)

The product of Example 38A was processed as described in Example 2B to provide the title compound. $^1$H NMR (MeOD, 300 MHz) δ 2.12 (d, J=15.0 Hz, 1H), 2.32 (d, J=15.0 Hz, 1H), 3.42 (s, 2H), 3.79 (dd, J=2.0, 10.0 Hz, 1H), 4.60 (s, 1H), 4.88 (s, 1H), 7.70 (t, J=1.0 Hz, 1H), 8.21 (d, J=3.0 Hz, 1H), 8.42 (d, J=1.0 Hz, 1H); MS (DCI/NH$_3$) m/z 219 (M+H)$^+$; Anal. calculated for $C_{24}H_{30}N_4O_6S_2$: C, 52.27; H, 5.73; N, 11.55. Found: C, 51.92; H, 5.66; N, 10.48.

EXAMPLE 39

(1R,4R)-2-(5-hydroxy-3-pyridinyl)-2,5-diazabicyclo[2.2.1]heptane 4-methylbenzenesulfonate

Example 39A tert-butyl (1R,4R)-5-(5-benzyloxy-3-pyridinyl)-2,5-diazabicyclo[2.2.1]heptane-2-carboxylate The product from Example 15B and 5-(benzyloxy)-3-bromo-pyridine, prepared as described in (U.S. Pat. No. 5,733,912) were coupled according to the procedure described in Example 15C to provide the title compound. MS (DCI/NH$_3$) m/z 382 (M+H)$^+$.

Example 39B (1R,4R)-2-(5-benzyloxy-3-pyridinyl)-2,5-diazabicyclo[2.2.1]heptane The product from Example 39A (0.52 g, 1.36 mmol) in EtOH (10 mL) was treated with 4N HCl/dioxane (10 mL) and stirred at ambient temperature for 1 hour. The volatiles were removed under reduced pressure and the residue was purified on SiO$_2$ (10% MeOH/CH$_2$Cl$_2$/1% NH$_4$OH) to provide the title compound (0.347 g, 90% yield) as a white solid. MS (DCI/NH$_3$) m/z 282 (M+H)$^+$.

Example 39C (1R,4R)-2-(5-hydroxy-3-pyridinyl)-2,5-diazabicyclo[2.2.1]heptane The product from Example 39B (0.347 g, 1.23 mmol) in EtOH (10 mL) was treated with 10% Pd/C (10 mg) and stirred at ambient temperature under a hydrogen atmosphere (1 atm) for 16 hours. The catalyst was filtered, washed with EtOH (10 mL) and the combined filtrate was concentrated under reduced pressure. The residue was purified by chromatography on SiO$_2$ (10% MeOH/CH$_2$Cl$_2$/1% NH$_4$OH) to provide the free base of the title compound (0.168 g, 71% yield) as a light yellow solid. The free base was dissolved in EtOH and treated with a solution of para-toluenesulfonic acid (0.167 g, 1 eq) in a minimum volume of EtOH. The solution was concentrated under reduced pressure to provide the title compound (330 mg, 71% yield) as an off-white foam. $^1$H NMR (MeOD, 300 MHz) δ 2.05(d, J=13.0 Hz, 1H), 2.28 (d, J=13.0 Hz, 1H), 3.32-3.36 (m, 3H), 3.70 (dd, J=3.0, 10.0 Hz, 1H), 4.51 (s, 1H), 4.67 (s, 1H), 6.55 (t, J=2.0 Hz, 1H), 7.51 (d, J=2.0 Hz, 1H), 7.53 (d, J=2.0 Hz, 1H); MS (DCI/NH$_3$) m/z 192 (M+H)$^+$; Anal. calculated for C$_{17}$H$_{21}$N$_3$O$_4$S.0.8H$_2$O: C, 54.04; H, 6.03; N, 11.12. Found: C, 54.15; H, 6.11; N, 10.83.

EXAMPLE 40

(1R,4R)-2-(6-chloro-5-hydroxy-3-pyridinyl)-2,5-diazabicyclo[2.2.1]heptane 4-methylbenzenesulfonate

Example 40A 5-bromo-3-pyridinol 3-(Benzyloxy)-5-bromopyridine (15.0 g, 56.8 mmol), prepared as described in (U.S. Pat. No. 5,733,912), and 30% HBr/HOAc (200 mL) were stirred at ambient temperature for 16 hours. The reaction mixture was diluted with diethyl ether (500 mL) and the resulting white solid (12.9 g) was isolated by filtration. The solid, in methanol (300 ml), was treated with concentrated NH$_4$OH (50 mL). After stirring at ambient temperature for 12 hours, the reaction mixture was concentrated under reduced pressure to provide the title compound (9.8 g, 89%) as a white solid. MS (DCI/NH$_3$) m/z 174, 176 (M+H)$^+$.

Example 40B 5-bromo-2-chloro-3-pyridinol

The product from Example 40A (9.8 g, 56.3 mmol) and NaOH (2.40 g, 100 mmol) in water (100 mL) were treated with NaOCl (35 ml of 10% solution). The reaction mixture was stirred at ambient temperature for 16 hours and then quenched with acetic acid (5 ml), extracted with ethyl acetate (500 mL), dried (MgSO$_4$), and concentrated under reduced pressure. The residue was purified on SiO$_2$ (3% MeOH/CH$_2$Cl$_2$) to provide the title compound (11.20 g, 96% yield) as a yellow solid. MS (DCI/NH$_3$) m/z 208, 210 (M+H)$^+$.

Example 40C 5-bromo-2-chloro-3-(methoxymethoxy)pyridine

The product from Example 40B (11.2 g, 53.1 mmol) in diethyl ether (50 mL) was added to a suspension of NaH (1.69 g, 70 mmol) in DMF (300 mL) and diethyl ether (60 mL). The mixture was stirred at ambient temperature for 30 minutes and then treated with a solution of chloromethyl methyl ether (5.65 g, 70 mmol, Aldrich Chemical Co.) in diethyl ether (30 mL). After stirring at ambient temperature for 2 hours, the mixture was quenched by cautious addition of water (200 mL). The aqueous mixture was extracted with diethyl ether (300 mL), and the organic phase was dried (MgSO$_4$) and concentrated under reduced pressure. The residue was purified on SiO$_2$ (ethyl acetate/hexane (1/4)) to provide the title compound (8.29 g, 61% yield) as a colorless oil. MS (DCI/NH$_3$) m/z 252, 254 (M+H)$^+$.

Example 40D tert-butyl (1R,4R)-5-(6-chloro-5-methoxymethoxy-3-pyridinyl)-2,5-diazabicyclo[2.2.1]heptane-2-carboxylate The product from Example 15B (1.0 g, 5.0 mmol) in anhydrous toluene (50 mL) was treated with the product from Example 40C (1.27 g, 5.0 mmol), Pd$_2$(dba)$_3$ (0.093 g, 0.1 mmol), BINAP (0.126 g, 0.2 mmol) and sodium tert-butoxide (0.83 g, 8.6 mmol). The reaction mixture was heated at 80° C. for 4 hours. The mixture was allowed to cool to ambient temperature, diluted with ether (100 mL), washed with brine (100 mL), dried (MgSO$_4$), and concentrated under reduced pressure. The residue was purified by chromatography on SiO$_2$ (5% MeOH/CH$_2$Cl$_2$) to provide the title compound (1.0 g, 52% yield) as a yellow oil. MS (DCI/NH$_3$) m/z 370 (M+H)$^+$.

Example 40E (1R,4R)-2-(6-chloro-5-hydroxy-3-pyridinyl)-2,5-diazabicyclo[2.2.1]heptane 4-methylbenzenesulfonate The product from Example 40D (0.60 g, 1.62 mmol) in acetonitrile (8 mL) was treated with Amberlist resin (7.5 g)

and shaken at ambient temperature for 48 hours. The resin was removed by filtration and the filtrate was concentrated under reduced pressure. The residue was purified on $SiO_2$ (10% $MeOH/CH_2Cl_2$/1% $NH_4OH$) to provide the free base of the title compound (0.121 g) as a white solid. The free base in EtOH was treated with 4-methylbenzenesulfonic acid (0.102 g, 1 eq.) for 10 minutes. The solvent was removed under reduced pressure to provide the title compound (222 mg, 33% yield) as a white solid: $^1H$ NMR (MeOD, 300 MHz) δ 2.06 (d, J=12.0 Hz, 1H), 2.37 (d, J=12.0 Hz, 1H), 3.28-3.35 (m, 3H), 3.70 (dd, J=3.0, 12.0 Hz, 1H), 4.51 (s, 1H), 4.65 (s, 1H), 6.65 (d, J=3.0 Hz, 1H), 7.35 (d, J=3.0 Hz, 1H); MS ($DCI/NH_3$) m/z 226 $(M+H)^+$, 243 $(M+NH_4)^+$; Anal. Calculated for $C_{17}H_{20}N_3O_4SC1.0.2$ $TsOH.0.60H_2O$: C, 49.87; H, 5.19; N, 9.48. Found: C, 49.86; H, 5.36; N, 9.52.

EXAMPLE 41

3-(3-pyridinyl)-3,9-diazabicyclo[4.2.1]nonane bis(4-methylbenzenesulfonate)

The product from Example 36 (1.6 mmol) was hydrogenated according to the procedure of Example 37B to provide the free base (86% yield). This was combined with 4-methylbenzenesulfonate (2.0 eq) and the obtained solid was recrystallized from ethanol/ethyl acetate to provide the title compound. $^1H$ NMR ($CD_3OD$, 300 MHz) δ 1.73-1.83 (m, 1H), 1.92-2.35 (m, 5H), 2.47 (s, 3H), 3.71-3.82 (m, 3H), 3.94 (br d, J=15 Hz, 1H), 4.27 (br d, J=15 Hz, 2H), 7.23 (d, J=7.5 Hz, 4H), 7.69 (d, J=7.5 Hz, 4H), 7.80 (m, 1H), 8.0-8.09 (m, 2H), 8.48 (d, J=3 Hz, 1H); MS ($DCI/NH_3$) m/z 204 $(M+H)^+$, 221 $(M+NH_4)^+$; Anal. Calcd. for $C_{12}H_{17}N_3.C_{14}H_{16}O_6S_2$: C, 57.02; H, 6.07; N, 7.67. Found: C, 56.88; H, 6.17; N, 7.57.

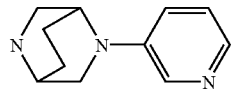

EXAMPLE 42

2-(3-pyridinyl)-2,5-diazabicyclo[2.2.2]octane dihydrochloride

Example 42A tert-butyl 5-(3-pyridinyl)-2,5-diazabicylo[2.2.2]octane-2-carboxylate 2-5-Diazabicyclo[2.2.2]octane (390 mg, 3.5 mmole), prepared by the method of Sturm and Henry (J. Med. Chem. (1974), 17, 481), was treated with 3-bromopyridine (545 mg, 3.5 mmole), BINAP (92 mg, 0.14 mmole), $Pd_2(dba)_3$ (40 mg, 0.07 mmole) and sodium tert-butoxide (431 mg 4.5 mmole) in toluene (10 mL) under a nitrogen atmosphere. After heating the mixture at 75° C.□5° C. for 2 hours, the mixture was allowed to cool to ambient temperature and treated with di-tert-butyl-dicarbonate (1.5 g, 6.9 mmole) and then allowed to stir an additional 16 hours. The reaction mixture was filtered and concentrated under reduced pressure. The residue was purified by chromatography ($SiO_2$, hexanes:ethyl acetate 9:1 to 1:1) to provide the title compound (193 mg, 19% yield). MS ($DCI/NH_3$) m/z 290 $(M+H)^+$, 307 $(M+NH_4)^+$.

Example 42B 2-(3-pyridinyl)-2,5-diazabicyclo[2.2.2]octane dihydrochloride

The product from Example 42A (137 mg, 0.6 mmole) was treated with a 1:1 mixture of $CH_2Cl_2$ and TFA (3 mL). After two hours, the solvent was removed under reduced pressure and the residue purified by chromatography ($SiO_2$, $CHCl_3$: $MeOH:NH_4OH$ 95:5:0 to 95:4.5:0.5) to provide the free base. The free base was treated with excess 1M HCl in diethyl ether to provide the title compound (65 mg, 37% yield). $^1H$ NMR ($CD_3OD$, 300 MHz) δ 2.04-2.17 (m, 2H), 2.21-2.25 (m, 2H), 3.5-3.69 (m, 3H), 3.90 (d, J=11.63 Hz 1H), 4.00 (br s, 1H), 4.45 (br s, 1H), 7.87 (dd, J=5.01, 8.82 Hz, 1H), 7.94 (dd, J=1.01, 9.16 Hz, 1H), 8.00 (d, J=5.08 Hz, 1H), 8.28 (d, J=1.70 Hz, 1H); MS ($DCI/NH_3$) m/z 190 $(M+H)^+$, 207 $(M+NH_4)^+$; Anal. Calculated for $C_{11}H_{15}N_3.2.1$ HCl.0.4 $C_4H_8O_2$: C, 50.27; H, 6.80; N, 13.96. Found: C, 50.05; H, 7.12; N, 14.34.

EXAMPLE 43

(1S,4S)-2-(5-methoxy-3-pyridinyl)-2,5-diazabicyclo [2.2.1]heptane bis(4-methylbenzenesulfonate)

Example 43A 3-bromo-5-methoxypyridine

A suspension of NaH (0.47 g, 19.6 mmol) in DMF (20 mL) was cautiously treated with methanol (0.59 g, 18.4 mmol). After 30 minutes, the mixture was treated with a solution of 3,5-dibromopyridine (4.0 g, 16.9 mmol) in DMF (5.0 mL). After stirring overnight, the reaction mixture was quenched with saturated aqueous $NH_4Cl$ and extracted with diethyl ether (200 mL). The organic phase was dried ($MgSO_4$) and concentrated under reduced pressure. The residue was purified by chromatography on $SiO_2$ ($CH_2Cl_2$) to provide the title compound (2.24 g, 70% yield) as a yellow solid.

Example 43B tert-butyl (1S,4S)-5-(5-methoxy-3-pyridinyl)-2,5-diazabicyclo[2.2.1]heptane-2-carboxylate tert-Butyl (1S,4S)-2,5-diazabicyclo[2.2.1]heptane-2-carboxylate, prepared as described in (J. Med. Chem., (1988) 31, 1598-1611), and the product from Example 43A were coupled according to the procedure described in Example 1A to provide the title compound. MS ($DCI/NH_3$) m/z 306 $(M+H)^+$.

Example 43C (1S,4S)-2-(5-methoxy-3-pyridinyl)-2,5-diazabicyclo [2.2.1]heptane bis(4-methylbenzenesulfonate)

The product from Example 43B was processed as described in Example 2B to provide the title compound. $^1H$ NMR ($CDCl_3$, 300 MHz) δ 1.82-2.01 (m, 2H), 3.02 (d, J=10 Hz, 1H), 3.08 (s, 2H), 3.63 (dd, J=3.0, 9.0 Hz, 1H), 3.82 (s, 3H), 3.87 (s, 1H), 4.32 (s, 1H), 6.33 (t, J=2.0 Hz, 1H), 7.64 (d, J=3.0 Hz, 1H), 7.68 (d, J=2.0 Hz, 1H); MS ($DCI/NH_3$) m/z 206 $(M+H)^+$; Anal. calculated for $C_{25}H_{31}N_3O_7S_2$. $0.78H_2O$: C, 52.89; H, 5.86; N, 7.40. Found: C, 52.63; H, 5.91; N, 7.12.

EXAMPLE 44

(1R,4R)-2-(5-cyano-3-pyridinyl)-2,5-diazabicyclo[2.2.1]heptane 4-methylbenzenesulfonate

Example 44A tert-butyl (1R,4R)-5-(5-bromo-3-pyridinyl)-2,5-diazabicyclo[2.2.1]heptane-2-carboxylate The product from Example 15B and 3,5-dibromopyridine were processed as described in Example 1A to provide the title compound.

Example 44B tert-butyl (1R,4R)-5-(5-cyano-3-pyridinyl)-2,5-diazabicyclo[2.2.1]heptane-2-carboxylate The product from Example 44A was processed as described in Example 32A to provide the title compound. MS (DCI/NH$_3$) m/z 301 (M+H)$^+$.

Example 44C (1R,4R)-2-(5-cyano-3-pyridinyl)-2,5-diazabicyclo[2.2.1]heptane 4-methylbenzenesulfonate The product of Example 44B was processed as described in Example 2B to provide the title compound. $^1$H NMR (MeOD, 300 MHz) δ 2.10 (dt, J=1.0, 11.0 Hz, 1H), 2.31 (dt, J=1.0, 11.0 Hz, 1H), 3.38 (d, J=2.0 Hz, 2H), 3.42 (d, J=1.0 Hz, 1H), 3.75 (dd, J=3.0, 9.0 Hz, 1H), 4.56 (s, 1H), 4.82(s, 1H), 7.50 (dd, J=1.0, 4.0 Hz, 1H), 8.23 (d, J=4.0 Hz, 1H), 8.25 (d, J=3.0 Hz, 1H); MS (DCI/NH$_3$) m/z 201 (M+H)$^+$, 218 (M+NH$_4$)$^+$; Anal. calculated for C$_{18}$H$_{21}$N$_4$O$_3$S.0.50H$_2$O: C, 56.68; H, 5.55; N, 14.69. Found: C, 56.92; H, 5.48; N, 14.29.

EXAMPLE 45

(1S,4S)-2-(6-chloro-5-hydroxy-3-pyridinyl)-2,5-diazabicyclo[2.2.1]heptane 4-methylbenzenesulfonate

Example 45A tert-butyl (1S,4S)-5-(6-chloro-5-methoxymethoxy-3-pyridinyl)-2,5-diazabicyclo[2.2.1]heptane-2-carboxylate tert-Butyl (1S,4S)-2,5-diazabicyclo[2.2.1]heptane-2-carboxylate, prepared as described in (J. Med. Chem. (1988) 31, 1598-1611), and the product from Example 40C were processed as described in Example 40D to provide the title compound. MS (DCI/NH$_3$) m/Z 370 (M+H)$^+$.

Example 45B (1S,4S)-2-(6-chloro-5-hydroxy-3-pyridinyl)-2,5-diazabicyclo[2.2.1]heptane 4-methylbenzenesulfonate The product from Example 45A (1.00 g, 2.7 mmol) in EtOH (2.0 mL) was treated with 4N HCl/dioxane (5 mL) and then heated at 60° C. for 4 hours. The reaction mixture was allowed to cool to ambient temperature and then concentrated under reduced pressure. The residue was purified on SiO$_2$ (10% MeOH/CH$_2$Cl$_2$/1% NH$_4$OH) to provide the free base of the title compound (0.424 g) as a light yellow solid. The free base was treated with 4-methylbenzenesulfonic acid (0.356 g, 1 eq) in a minimum amount of EtOH for 10 minutes then concentrated under reduced pressure to produce the title compound (0.78 g, 72% yield) as a white solid. $^1$H NMR (MeOD, 300 MHz) δ 2.08 (d, J=12.0 Hz, 1H), 2.28 (d, J=12.0 Hz, 1H), 3.32-3.38 (m, 3H), 3.70 (dd, J=3.0, 12.0 Hz, 1H), 4.52 (t, J=10.0 Hz, 1H), 4.65 (s, 1H), 6.64 (d, J=3.0 Hz, 1H), 7.32 (d, J=3.0 Hz, 1H); MS (DCI/NH$_3$) m/z 226 (M+H)$^+$, 243 (M+NH$_4$)$^+$; Anal. calculated for C$_{17}$H$_{20}$N$_3$ClO$_4$S.3.0H$_2$O: C, 45.18; H, 5.80; N, 9.30. Found: C, 45.12; H, 5.68; N, 9.29.

EXAMPLE 46

(1R,4R)-2-(6-methoxy-3-pyridinyl)-2,5-diazabicyclo[2.2.1]heptane 4-methylbenzenesulfonate

Example 46A tert-butyl (1R,4R)-5-(6-methoxy-3-pyridinyl)-2,5-diazabicyclo[2.2.1]heptane-2-carboxylate The product from Example 15B and 2-methoxy-5-bromopyridine (purchased from Frontier Scientific) were processed as described in Example 15C to provide the title compound. MS (DCI/NH$_3$) m/z 306 (M+H)$^+$.

Example 46B (1R,4R)-2-(6-methoxy-3-pyridinyl)-2,5-diazabicyclo[2.2.1]heptane 4-methylbenzenesulfonate The product from Example 46A was processed as described in Example 2B to provide the title compound. $^1$H NMR (MeOD, 300 MHz) δ 2.05 (d, J=11.0 Hz, 1H), 2.28 (d, J=11.0 Hz, 1H), 3.25 (dd, J=3.0, 12.0 Hz, 1H), 3.35 (s, 2H), 3.72 (dd, J=3.0, 12.0 Hz, 1H), 3.78(s, 3H), 4.48 (t, J=1.0 Hz, 1H), 4.61 (s, 1H), 6.84 (d, J=11.0 Hz, 1H), 7.28 (dd, J=3.0, 9.0 Hz, 1H), 7.53 (d, J=3.0 Hz, 1H); MS (DCI/NH$_3$) m/z 206 (M+H)$^+$; Anal. calculated for C$_{18}$H$_{23}$N$_3$O$_4$S.0.45.0H$_2$O: C, 56.07; H, 6.25; N,10.90. Found: C, 56.14; H, 6.12; N, 10.52.

EXAMPLE 47

(1R,4R)-2-(6-chloro-5-methyl-3-pyridinyl)-2,5-diazabicyclo[2.2.1]heptane 4-methylbenzenesulfonate

Example 47A tert-butyl (1R,4R)-5-(6-chloro-5-methyl-3-pyridinyl)-2,5-diazabicyclo[2.2.1]heptane-2-carboxylate The product from Example 15B and 2-chloro-5-iodo-3-methylpyridine, prepared as described in (U.S. Pat. No. 5,733,912) were processed as described in Example 15C to provide the title compound. MS (DCI/NH$_3$) m/z 324 (M+H)$^+$.

Example 47B (1R,4R)-2-(6-chloro-5-methyl-3-pyridinyl)-2,5-diazabicyclo[2.2.1]heptane 4-methylbenzenesulfonate The product from Example 47A was processed as described in Example 2B to provide the title compound. $^1$H NMR (CDCl$_3$, 300 MHz) δ 1.89 (d, J=10.0 Hz, 1H), 1.98 (d, J=10.0 Hz, 1H), 2.31 (s, 3H), 3.00 (dd, J=1.0, 10.0 Hz, 1H), 3.09 (s, 2H), 3.63 (dd, J=3.0, 9.0 Hz, 1H), 3.88 (s, 1H), 4.29 (s, 1H), 6.72 (d, J=2.0 Hz, 1H), 7.56 (d, J=3.0 Hz, 1H); MS (DCI/NH$_3$) m/z 224 (M+H)$^+$; Anal. calculated for C$_{18}$H$_{22}$N$_3$O$_3$SCl.0.2H$_2$O: C, 54.12; H, 5.65; N, 10.52. Found: C, 54.21; H, 5.80; N, 10.18.

EXAMPLE 48

(1R,4R)-2-(5,6-dichloro-3-pyridinyl)-2,5-diazabicyclo[2.2.1]heptane 4-methylbenzenesulfonate

Example 48A tert-butyl (1R,4R)-5-(5,6-dichloro-3-pyridinyl)-2,5-diazabicyclo[2.2.1]heptane-2-carboxylate The product from Example 15B and 2,3-dichloro-5-iodopyridine, prepared as described in (U.S. Pat. No. 5,733,912) were processed as described in Example 15C to provide the title compound. MS (DCI/NH$_3$) m/z 344 (M+H)$^+$.

Example 48B (1R,4R)-2-(5,6-dichloro-3-pyridinyl)-2,5-diazabicyclo[2.2.1]heptane 4-methylbenzenesulfonate The product from Example 48A was processed as described in Example 2B to provide the title compound. $^1$H NMR (MeOD, 300 MHz) δ 2.07 (m, 1H), 2.30 (m, 1H), 3.28-3.34 (m, 1H), 3.47 (s, 2H), 3.72 (dd, J=2.0, 10.0 Hz, 1H), 4.53 (t, J=1.0 Hz, 1H), 4.75 (s, 1H), 7.36 (d, J=3.0 Hz, 1H), 7.77 (d, J=3.0 Hz, 1H); MS (DCI/NH$_3$) m/z 244 (M+H)$^+$; Anal. calculated for C$_{17}$H$_{19}$N$_3$O$_3$SCl$_2$.0.05 EtOH: C, 49.06; H, 4.65; N, 10.04. Found: C, 49.22; H, 5.04; N, 11.05.

EXAMPLE 49

6-(6-chloro-3-pyridinyl)-2,6-diazabicyclo[3.2.1]octane bis(4-methylbenzenesulfonate)

Example 49A tert-butyl 2,6-diazabicyclo[3.2.1]octane-2-carboxylate

The product from Example 35B (140 mg, 0.568 mmol) in CH$_2$Cl$_2$ at ambient temperature was treated with triethylamine followed by di-tert-butyl dicarbonate. The solution was stirred for 2 hours, diluted with saturated aqueous K$_2$CO$_3$, and extraced with CH$_2$Cl$_2$ (2×). The organic extracts were combined, dried (Na$_2$SO$_4$), and concentrated under reduced pressure to provide 190 mg a colorless oil. A suspension of the oil and 10% Pd/C (20 mg) in MeOH (10 mL) were stirred under one atmosphere of hydrogen (balloon) for 6 hours. The catalyst was removed by filtration through a plug of Celite (CH$_2$Cl$_2$ wash). The filtrate was concentrated to provide (106 mg, 91%) the title compound as a colorless oil. MS (DCI/NH$_3$) m/z 213 (M+H)$^+$, 230 M+NH$_4$)$^+$.

Example 49B tert-butyl 6-(6-chloro-3-pyridinyl)-2,6-diazabicyclo[3.2.1]octane-2-carboxylate The product from Example 49A and 2-chloro-5-iodopyridine were processed as described in Example 1A to provide the title compound (30% yield) as a light yellow oil. MS (DCI/NH$_3$) m/z 324, 326 (M+H)$^+$.

Example 49C 6-(6-chloro-3-pyridinyl)-2,6-diazabicyclo[3.2.1]octane bis(4-methylbenzenesulfonate)

The product from Example 49B (40 mg, 0.12 mmol) in EtOAc (3 mL) was treated with p-toluenesulfonic acid-monohydrate (59 mg, 0.31 mmol). The solution was refluxed for 2 hours and allowed to cool to ambient temperature resulting in formation of a precipitate. The precipitate was triturated with diethyl ether (2×) and placed under high vacuum to provide 70 mg (85%) of the title compound as a white solid. $^1$H NMR (D$_2$O) δ 1.92 (m, 1H), 2.14-2.28 (m, 3H), 2.99 (s, 6H), 2.99 (dt, J=5.5, 12.9 Hz, 1H), 3.31 (dd, J=6.6, 13.4 Hz, 1H), 3.56 (d, J=12.1 Hz, 1H), 3.77 (dd, J=4.4, 12.1 Hz, 1H), 4.38 (m, 2H), 7.25 (dd, J=3.2, 9.0 Hz, 1H), 7.36 (d, J=8.5 Hz, 4H), 7.40 (d, J=9.2 Hz, 1H), 7.68 (d, J=8.5 Hz, 4H), 7.78 (d, J=2.9 Hz, 1H); MS (CI/NH3) m/z 224, 226 (M+H)$^+$; Anal. Calcd. for C$_{11}$H$_{14}$ClN$_3$.2.5C$_7$H$_8$O$_3$S.0.5H$_2$O: C, 51.61; H, 5.32; N, 6.34. Found: C, 51.31; H, 5.43; N, 6.21.

EXAMPLE 50

(1R,4R)-2-(5-aminocarbonyl-3-pyridinyl)-2,5-diazabicyclo[2.2.1]heptane bis(4-methylbenzenesulfonate)

Example 50A tert-butyl (1R,4R)-5-(5-aminocarbonyl-3-pyridinyl)-2,5-diazabicyclo[2.2.1]heptane-2-carboxylate The product from Example 44A was processed according to the procedure described in Example 38A to provide the title compound. MS (DCI/NH$_3$) m/z 319 (M+H)$^+$.

Example 50B (1R,4R)-2-(5-aminocarbonyl-3-pyridinyl)-2,5-diazabicyclo[2.2.1]heptane bis(4-methylbenzenesulfonate)

The product from Example 50A was processed as described in Example 2B to provide the title compound. $^1$H NMR (MeOD, 300 MHz) δ 2.26 (d, J=12.0 Hz, 1H), 2.25 (d, J=12.0 Hz, 1H), 3.41-3.52 (m, 3H), 3.82 (dd, J=2.0, 10.0 Hz, 1H), 4.65 (t, J=1.0 Hz, 1H), 5.96 (s, 1H), 8.14 (dd, J=1.0, 3.0 Hz,1H), 8.32 (d, J=2.0 Hz, 1H), 8.47 (d, J=1.0 Hz, 1H); MS (DCI/NH$_3$) m/z 219 (M+H)$^+$; Anal. calculated for C$_{24}$H$_{30}$N$_4$O$_7$S$_2$.0.40 TsOH.1.0 H$_2$O: C, 50.49; H, 5.57; N, 8.79. Found: C, 50.53; H, 5.75; N, 8.76.

EXAMPLE 51

(1R,4R)-2-(6-chloro-5-methoxy-3-pyridinyl)-2,5-diazabicyclo[2.2.1]heptane 4-methylbenzenesulfonate

Example 51A 5-bromo-2-chloro-3-methoxypyridine

The product from Example 40B (1.2 g, 5.8 mmol) in diethyl ether (5 mL) was added to a suspension of NaH (181 mg, 7.5 mmol) in dry DMF (30 mL) and diethyl ether (6 mL). After stirring at ambient temperature for 30 minutes, the mixture was treated with a solution of iodomethane (1.06 g, 7.5 mmol) in diethyl ether (3 mL) and stirring was continued for an additional 30 minutes. The reaction mixture was quenched with water (20 mL), extracted with diethyl ether (100 mL), dried ($MgSO_4$), and concentrated under reduced pressure. The residue was purified on $SiO_2$ (ethyl acetate/hexane, 1/4) to provide the title compound (0.32 g, 25%) as a colorless oil. MS ($DCI/NH_3$) m/z 222/224/226 $(M+H)^+$.

Example 51B tert-butyl (1R,4R)-5-(6-chloro-5-methoxy-3-pyridinyl)-2,5-diazabicyclo[2.2.1]heptane-2-carboxylate The product from Example 15B and the product from Example 51A were processed as described in Example 15C to provide the title compound (74% yield). MS ($DCI/NH_3$) m/z 340 $(M+H)^+$.

Example 51C (1R,4R)-2-(6-chloro-5-methoxy-3-pyridinyl)-2,5-diazabicyclo[2.2.1]heptane 4-methylbenzenesulfonate The product from Example 51 B was processed as described in Example 2B to provide the title compound (50% yield). $^1$H NMR (MeOD, 300 MHz) δ 1.82 (d, J=12.0 Hz, 1H), 1.96 (d, J=12.0 Hz, 1H), 2.97 (s, 3H), 3.58 (dd, J=3.0, 12.0 Hz, 1H), 3.78-3.82 (m, 2H), 3.89 (s, 1H), 4.46 (s, 1H), 4.79 (s, 1H), 6.68 (d, J=2.0 Hz, 1H), 7.28 (d, J=2.0 Hz, 1H); MS ($DCI/NH_3$) m/z 240 $(M+H)^+$; Anal. calculated for $C_{18}H_{22}N_3O_4SCl.0.25$ TsOH.0.60$H_2O$: C, 50.93; H, 5.45; N, 9.02. Found: C, 50.94; H, 5.57; N, 8.95.

EXAMPLE 52

(1S,4S)-2-(5-pyrimidinyl)-2,5-diazabicyclo[2.2.1]heptane 4-methylbenzenesulfonate

Example 52A tert-butyl (1S,4S)-5-(5-pyrimidinyl)-2,5-diazabicyclo[2.2.1]heptane-2-carboxylate tert-Butyl (1S,4S)-2,5-diazabicyclo[2.2.1]heptane-2-carboxylate (330 mg, 1.6 mmol), prepared as described in (J. Med. Chem., (1988) 31, 1598-1611), and 5-bromopyrimidine (purchased from Acros Scientific) were processed as described in Example 15C to provide the title compound (99% yield). MS ($DCI/NH_3$) m/z 277 $(M+H)^+$.

Example 52B (1S,4S)-2-(5-pyrimidinyl)-2,5-diazabicyclo[2.2.1]heptane 4-methylbenzenesulfonate The product from Example 52B was processed as described in Example 2B to provide the title compound (33% yield). $^1$H NMR (MeOD, 300 MHz) δ 1.87-2.01 (m, 2H), 3.01-3.16 (m, 3H), 3.67 (dd, J=2.0, 8.0 Hz, 1H), 3.79 (s, 1H), 4.37 (s, 1H), 8.06 (s, 2H), 8.57 (s, 1H); MS ($DCI/NH_3$) M/Z 177 $(M+H)^+$; Anal. calculated for $C_{16}H_{20}N_4O_3S.0.10$ TsOH.0.25$H_2O$: C, 54.19; H, 5.80; N, 15.14. Found: C, 54.24; H, 5.89; N, 15.17.

EXAMPLE 53

(1S,4S)-2-(3-guinolinyl)-2,5-diazabicyclo[2.2.1]heptane acetate

Example 53A tert-butyl (1S,4S)-5-(3-quinolinyl)-2,5-diazabicyclo[2.2.1]heptane-2-carboxylate tert-Butyl (1S,4S)-2,5-diazabicyclo[2.2.1]heptane-2-carboxylate, prepared as described in (J. Med. Chem., (1988) 31, 1598-1611), and 3-bromoquinoline (purchased from the Aldrich Chemical Co.) were coupled according to the procedure described in Example 1A to provide the title compound.

Example 53B (1S,4S)-2-(3-guinolinyl)-2,5-diazabicyclo[2.2.1]heptane acetate

The product from Example 53A was processed as described in Example 34B to provide the crude hydrochloride. The crude hydrochloride was purified by preparative HPLC (Waters Nova-Pak HR C18 6 μm 60 Å 25×100 mm, 0-95% $CH_3CN$/10 mM $NH_4OAc$ over 10 minutes at 40 mL/minute) to provide the title compound after removal of solvents under reduced pressure. $^1$H NMR (MeOD, 300 MHz) δ 1.90 (s, 3H), 2.06 (br d, J=11 Hz, 1H), 2.24 (br d, J=11 Hz, 1H), 3.30, (br s, 2H), 3.41 (d, J=10 Hz, 1H), 3.84 (d, J=10 Hz, 1H), 4.33 (br s, 1H), 4.80 (br s, 1H), 7.34 (m, 1H), 7.46 (m, 2H), 7.73 (br d, J=7 Hz, 1H), 7.87 (br d, J=7 Hz, 1H), 8.51 (br d, J=3 Hz, 1H).

EXAMPLE 54

(1S,4S)-2-(3-methyl-5-isothiazolyl)-2,5-diazabicyclo[2.2.1]heptane acetate

Example 54A tert-butyl (1S,4S)-5-(3-methyl-5-isothiazolyl)-2,5-diazabicyclo[2.2.1]heptane-2-carboxylate tert-Butyl (1S,4S)-2,5-diazabicyclo[2.2.1]heptane-2-carboxylate, prepared as described in (J. Med. Chem., (1988) 31, 1598-1611) and 5-bromo-3-methylisothiazole, prepared as described in (U.S. Pat. No. 3,840,665) were coupled according to the procedure described in Example 1A to provide the title compound.

Example 54B

(1S,4S)-2-(3-methyl-5-isothiazolyl)-2,5-diazabicyclo[2.2.1]heptane acetate

The product from Example 54A was processed as described in Example 53B to provide the title compound. $^1$H NMR (MeOD, 300 MHz) δ 1.84(s, 3H), 1.86 (m, 1H), 2.04 (br d, J=11 Hz, 1H), 2.18 (s, 3H), 3.06 (m, 2H), 3.16 (br d, J=10 Hz, 1H), 3.30 (m, 1H), 4.05 (br s, 1H), 4.17 (br s, 1H), 5.99 (s, 1H).

EXAMPLE 55

(1R,4R)-2-(thieno[3,2-b]pyridin-2-yl)-2,5-diazabicyclo[2.2.1]heptane acetate

Example 55A tert-butyl (1R,4R)-5-(thieno[3,2-b]pyridin-2-yl)-2,5-diazabicyclo[2.2.1]heptane-2-carboxylate The product from Example 15B and 2-bromothieno[3,2-b]pyridine, prepared as described in (J. Het. Chem. (1984), 785-789), were processed as described in Example 1A to provide the title compound.

Example 55B

(1R,4R)-2-(thieno[3,2-b]pyridin-2-yl)-2,5-diazabicyclo[2.2.1]heptane acetate The product from Example 55A was processed as described in Example 53B to provide the title compound. $^1$H NMR (MeOD, 300 MHz) δ 1.92 (s, 3H), 2.04 (br d, J=11 Hz, 1H), 2.26 (br d, J=11 Hz, 1H), 3.28 (m, 1H), 3.41 (m, 2H), 3.74 (dd, J=10, 2 Hz, 1H), 4.33 (br s, 1H), 4.53 (br s, 1H), 6.18 (s, 1H), 7.01 (dd, J=8, 4 Hz, 1H), 8.01 (br d, J=8 Hz, 1H), 8.29 (br d, J=4 Hz, 1H).

EXAMPLE 56

9-(6-chloro-3-pyridinyl)-3,9-diazabicyclo[4.2.1]nonane fumarate

Example 56A tert-butyl 9-methyl-3,9-diazabicyclo[4.2.1]nonane-3-carboxylate

9-Methyl-3,9-diazabicyclo[4.2.1]nonane (4.60 g, 33 mmol), prepared as described in (U.S. Pat. No. 2,999,091), in CHCl$_3$ (50 mL) at 0° C., was treated with triethyl amine (6.7 g, 66 mmol) and di-t-butyl dicarbonate (14.4 g, 66 mmol). The mixture was allowed to warm to ambient temperature and stir for 12 hours. The reaction mixture was washed in succession with saturated NaHCO$_3$ and brine. The organic phase was dried (MgSO$_4$) and concentrated under reduced pressure to provide the title compound (99% yield). MS (DCI/NH$_3$) m/z 241 (M+H)$^+$.

Example 56B t-butyl 3,9-diazabicyclo[4.2.1]nonane-3-carboxylate

The product of Example 56A was processed (on 33 mmol scale) according to the procedure of Example 36 to provide the title compound (51% yield). MS (DCI/NH$_3$) m/z 227 (M+H)$^+$, 241 (M+NH$_4$)$^+$.

Example 56C t-butyl 9-(6-chloro-3-pyridinyl)-3,9-diazabicyclo[4.2.1]nonane-3-carboxylate The product of Example 56B (17 mmol) and 2-chloro-5-iodopyridine (21 mmol) were coupled according the procedure of Example 15C to provide the title compound (21% yield). MS (DCI/NH$_3$) m/z 338 (M+H)$^+$, 355 (M+NH$_4$)$^+$.

Example 56D

9-(6-chloro-3-pyridinyl)-3,9-diazabicyclo[4.2.1]nonane fumarate

The product of Example 56C was treated with trifluoroacetic acid according to the procedure of Example 15D. After purification by chromatography (SiO$_2$; 10% MeOH: 89% CH$_2$Cl$_2$:1% NH$_4$OH), the free base was combined with fumaric acid (1.1 eq.) in hot EtOAc. Upon cooling, the title compound separated as a solid in 97% yield. $^1$H NMR (CD$_3$OD, 300 MHz) δ 1.84-2.08 (m, 3H), 2.22-2.56 (m, 3H), 2.92-3.02 (m, 1H), 3.16-3.29 (m, 2H), 3.58 (d, J=4.5, 13.5 Hz, 1H), 4.47-4.55 (m, 1H), 4.57-4.66 (m, 1H), 6.67 (s, 2H), 7.25 (s, 2H), 7.86 (s, 1H); MS (DCI/NH$_3$) m/z 238 (M+H)$^+$, 255 (M+NH$_4$)$^+$; Anal. Calcd. for C$_{12}$H$_{16}$ClN$_3$.C$_4$H$_4$O$_4$: C, 54.32; H, 5.70; N, 11.88. Found: C, 54.33; H, 5.77; N, 11.77.

EXAMPLE 57

3-(3-pyridinyl)-3,7-diazabicyclo[3.3.1]nonane bis(4-methylbenzenesulfonate)

Example 57A

3-(3-pyridinyl)-3,7-diazabicyclo[3.3.1]nonane 3,7-Diazabicyclo[3.3.1]nonane, prepared as described in (Garrison, G. L. et. al., J. Org. Chem. 58, 27, (1993) 7670), and 3-bromopyridine were processed as described in Example 1A. The proportions of reagents were changed from Example 1A to the following: Pd$_2$(dba)$_3$ (0.02 eq), BINAP (0.05 eq), and NaOt-Bu (1.7 eq). The title compound was obtained in 25% yield after purification by flash chromatography (silica gel; CHCl$_3$:MeOH:NH$_4$OH; 90:5:1). MS (DCI/NH$_3$) m/z 204 (M+H)$^+$.

Example 57B

3-(3-pyridinyl)-3,7-diazabicyclo[3.3.1]nonane bis(4-methylbenzenesulfonate)

The product from Example 57A was treated with p-toluenesulfonic acid (2.0 eq) and the obtained solid recrystallized from ethanol/ether to provide the title compound (53% yield). $^1$H NMR (CD$_3$OD, 300 MHz) δ 2.04 (m, 2H), 2.37 (s, 6H), 2.39 (m, 2H), 3.23 (m, 2H), 3.31 (m, 2H), 3.59 (bd, J=13.24 Hz, 2H), 4.04 (bd, 12.14 Hz, 2H), 7.23 (d, J=8.09 Hz, 4H), 7.67(d, J=8.09 Hz, 4H), 7.88 (dd, J=5.52, 8.83 Hz, 1H), 8.20-8.24(m, 2H), 8.50 (d, J=2.57 Hz, 1H); MS (DCI/NH$_3$) m/z 204 (M+H)$^+$; Anal. calculated for C$_{12}$H$_{17}$N$_3$.2.2 TsOH.H$_2$O C, 56.01; H, 6.04; N, 7.15. Found: C, 56.25; H, 6.10; N, 6.79.

EXAMPLE 58

3-(6-Chloro-3-pyridinyl)-3,7-diazabicyclo[3.3.1]nonane 4-methylbenzenesulfonate

Example 58A 3-(6-Chloro-3-pyridinyl)-3,7-diazabicyclo[3.3.1]nonane 3,7-Diazabicyclo[3.3.1]nonane, prepared as described in (Garrison, G. L. et. al., J. Org. Chem. 58, 27, (1993) 7670), and 2-chloro-5-iodopyridine were processed as described in Example 57A. The crude was purified by flash chromatography (silica gel; CHCl₃:MeOH:NH₄OH; 90:5:1) to provide the title compound (10% yield). MS (DCI/NH₃) m/z 238 (M+H)⁺.

Example 58B 3-(6-Chloro-3-pyridinyl)-3,7-diazabicyclo[3.3.1]nonane 4-methylbenzenesulfonate The product of Example 58A was treated with p-toluenesulfonic acid (1.0 eq) and the obtained solid recrystallized from ethanol/ether to provide the title compound (53% yield) $^1$H NMR (CD₃OD, 300 MHz) δ 2.00 (m, 2H), 2.31 (bs, 2H), 2.37 (s, 3H), 3.10 (m, 2H), 3.35 (m,2H), 3.57 (bd, J=13.22 Hz, 2H), 3.85 (bd, 11.19 Hz, 2H), 7.23 (d, J=8.14 Hz, 2H), 7.34 (d, J=8.13 Hz, 1H), 7.57 (dd, J=3.05, 8.81 Hz, 1H), 7.70 (d, J=8.13 Hz, 2H), 8.15 (d, J=3.39 Hz, 1H); MS (DCI/NH₃) m/z 238 (M+H)⁺; Anal. calculated for C₁₂H₁₆ClN₃.1.1 TsOH.0.5 H₂O C, 54.25; H, 5.96; N, 9.63. Found: C, 54.05; H, 5.60; N, 9.61.

EXAMPLE 59

6-(3-pyridinyl)-3,6-diazabicyclo[3.2.1]octane

Example 59A

2-[(2-nitrophenyl)sulfonyl]-2-azabicyclo[2.2.1]hept-5-ene

2-Azabicyclo[2.2.1]hept-5-ene (52.5 g, 54 mmole), prepared as described in (J Am Chem. Soc., (1985) 107, 1768), 2-nitrobenzenesulfonyl chloride (119.6, 54 mmole), and triethylamine (75 mL, 0.54 mmole) were combined in methylene chloride (500 mL) under a nitrogen atmosphere and stirred for 16 hours. The reaction mixture was quenched with water (500 mL) and the phases separated. The organic phase was washed with 2M HCl (5×100 mL), dried (MgSO₄), and concentrated under reduced pressure. The residue was purified by chromatography on silica gel (chloroform then hexane:EtOAc 95:5 to 8:2) to provide the title compound (23 g, 23% yield). MS (DCI/NH₃) m/e 281 (M+H)⁺, 298 (M+NH₄)⁺.

Example 59B 3-benzyl-6-[(2-nitrophenyl)sulfonyl]-3,6-diazabicyclo[3.2.1]octane Ozone (O₃/O₂) was bubbled through a solution of the product from Example 59A (5.6 g, 2 mmol) in methanol (100 mL) at −78° C. After one hour, a stream of oxygen was bubbled through the reaction mixture to remove excess ozone. The mixture was treated with dimethyl sulfide (2 mL) and the reaction mixture was allowed to warm to ambient temperature. After 30 minutes, benzylamine hydrochloride (25 g, 170 mmol) and 3A molecular sieves (30 g) were added. After 2 hours, NaBH₃CN (6.3 g, 10 mmol) was added and the reaction mixture stirred for an additional 16 hours. The solids were removed by filtration, and the filtrate was concentrated under reduced pressure. The residue was diluted with water (150 mL), acidified with 6N HCl (200 mL), and allowed to stir for 16 hours. Solid NaOH was added to bring the mixture to pH ~13. The mixture was extracted with EtOAc (5×200 mL). The extracts were combined, dried (K₂CO₃), and concentrated. The residue was purified by chromatography on silica gel (CHCl₃:MeOH 100:0 to 95:5) to provide the title compound (2.0 g, 28% yield). MS (DCI/NH₃) m/e 288 (M+H)⁺.

Example 59C 3-benzyl-3,6-diazabicyclo [3.2.1]octane

The product of Example 59B (1.98 g, 5 mmole) in DMF (5 mL) was treated with mercaptoacetic acid (0.7 ml, 10 mmole) and lithium hydroxide (0.48 g, 20 mmole). After stirring under a nitrogen atmosphere for 2 hours, the reaction mixture was poured into saturated Na₂CO₃ (20 mL) and extracted with EtOAc (5×20 mL). The organic extracts were combined, dried (K₂CO₃), and concentrated under reduced pressure. The residue was purified on silica gel (CHCl₃:MeOH:NH₄OH 95:5:0 to 9:1:0.1) to provide the title compound (450 mg, 45% yield). MS (DCI/NH₃) m/e 203 (M+H)⁺.

Example 59D 3-benzyl-6-(3-pyridinyl)-3,6-diazabicyclo[3.2.1]octane

The product of Example 59C (290 mg, 1.4 mmole) and 3-bromopyridine (340 mg, 2.15 mmole) were coupled using the procedure of Example 1A to provide the title compound (306 mg, 90% yield). MS (DCI/NH₃) m/e 280 (M+H)⁺.

Example 59E 6-(3-pyridinyl)-3,6-diazabicyclo[3.2.1]octane

The product from Example 59D (290 mg, 1.1 mmole), in ethanol (2.9 mL) was treated with 20% Pd(OH)₂/C (117 mg) under a hydrogen atmosphere (60 psi) for 36 hours. The reaction mixture was filtered and the solvent removed under reduced pressure. The residue was purified by chromatography (SiO₂, CHCl₃:MeOH:NH₄OH, 9:1:0 to 9:1:0.1) to provide the title compound (42 mg, 21% yield). $^1$H NMR (CD₃OD, 300 MHz) δ 2.17 (br s, 1H), 2.91 (br s, 1H), 3.40-3.70 (m, 8H) 4.51 (m, 1H), 7.84-7.85 (m, 2H), 8.09 (m, 1H), 8.19 (br s, 1H); MS (DCI/NH₃) m/e 190 (M+H)⁺.

EXAMPLE 60

3-(3-pyridinyl)-3,6-diazabicyclo[3.2.1]octane bis(4-methylbenzenesulfonate)

Example 60A t-butyl 3-benzyl-3,6-diazabicyclo[3.2.1]octane-6-carboxylate

The product of Example 59C can be treated with di-t-butyl dicarbonate (1.1 eq.) in methylene chloride for 4 hours.

The solvent is removed under reduced pressure and the residue purified by chromatography to provide the title compound.

Example 60B t-butyl 3,6-diazabicyclo[3.2.1]octane-6-carboxylate

The product from Example 60A can be processed according to the procedure of Example 59E to provide the title compound.

Example 60C 3-(3-pyridinyl)-3,6-diazabicyclo[3.2.1]octane bis(4-methylbenzenesulfonate)

The product from Example 60B can be processed according to the procedure of Example 2B to provide the title compound.

In Vitro Data

Determination of Nicotinic Acetylcholine Receptor Binding Potencies

Compounds of the invention were subjected to in vitro assays against the nicotinic acetylcholine receptor as described below and were found to be effective binders to the receptor. The In Vitro protocols for determination of nicotinic acetylcholine channel receptor binding potencies of ligands were determined as follows.

Binding of [$^3$H]-cytisine ([$^3$H]-CYT) to neuronal nicotinic acetylcholine receptors was accomplished using crude synaptic membrane preparations from whole rat brain (Pabreza et al., Molecular Pharmacol., 1990, 39:9). Washed membranes were stored at −80° C. prior to use. Frozen aliquots were slowly thawed and resuspended in 20 volumes of buffer (containing: 120 mM NaCl, 5 mM KCl, 2 mM MgCl$_2$, 2 mM CaCl$_2$ and 50 mM Tris-Cl, pH 7.4 @4° C.). After centrifuging at 20,000×g for 15 minutes, the pellets were resuspended in 30 volumes of buffer.

The test compounds were dissolved in water to make 10 mM stock solutions. Each solution was then diluted (1:100) with buffer (as above) and further taken through seven serial log dilutions to produce test solutions from $10^{-5}$ to $10^{-11}$ M.

Homogenate (containing 125-150 μg protein) was added to triplicate tubes containing the range of concentrations of test compound described above and [$^3$H]-CYT (1.25 nM) in a final volume of 500 μL. Samples were incubated for 60 minutes at 4° C., then rapidly filtered through Whatman GF/B filters presoaked in 0.5% polyethyleneimine using 3×4 mL of ice-cold buffer. The filters are counted in 4 mL of Ecolume® (ICN). Nonspecific binding was determined in the presence of 10 μM (−)-nicotine and values were expressed as a percentage of total binding. IC$_{50}$ values were determined with the RS-1 (BBN) nonlinear least squares curve-fitting program and IC$_{50}$ values were converted to Ki values using the Cheng and Prusoff correction ($K_i$=IC$_{50}$/(1+[ligand]/Kd of ligand).

The results are detailed in Table 1. Each Example Number corresponds to the synthetic Examples described above. Examples 1-17 and 20-59 are compounds of the present invention. Examples 18 and 19 are comparative. Example 18 is the 6-chloro-2-pyridinyl [2.2.1]derivative, corresponding to Example 1, the 6-chloro-3-pyridinyl derivative; and Example 19 is the 6-chloro-2-pyridinyl[3.2.1] derivative, corresponding to Example 12, the 6-chloro-3-pyridinyl [3.2.1]derivative. As a lower $K_i$ value is more desirable, the binding data suggest that the 3-pyridinyl derivative compounds of the present invention have higher affinity for the neuronal nicotinic acetylcholine receptor than 2-pyridinyl derivative compounds.

TABLE 1

| Binding Data | |
|---|---|
| Example Number | Average $K_i$ (nM) |
| 1 | 0.041 |
| 2 | 6.0 |
| 3 | 20 |
| 4 | 3.8 |
| 5 | 65 |
| 6 | 22 |
| 7 | 1900 |
| 8 | 2600 |
| 9 | >10,000 |
| 10 | 37 |
| 11 | 37 |
| 12 | 93 |
| 13 | 0.41 |
| 14 | 11 |
| 15 | 0.01 |
| 16 | 24 |
| 17 | 0.063 |
| 18 | 400 |
| 19 | >10,000 |
| 20 | 52 |
| 21 | 0.33 |
| 22 | 4.1 |
| 23 | 1.6 |
| 24 | 0.012 |
| 25 | 0.40 |
| 27 | 0.05 |
| 28 | 109 |
| 29 | 37 |
| 30 | 0.17 |
| 31 | 1.2 |
| 32 | 1.6 |
| 33 | 0.03 |
| 34 | 140 |
| 35 | 1.5 |
| 36 | 0.06 |
| 37 | 0.55 |
| 38 | 24 |
| 39 | 0.04 |
| 40 | 0.17 |
| 41 | 0.03 |
| 42 | 0.02 |
| 43 | 0.57 |
| 44 | 0.03 |
| 45 | 1.6 |
| 46 | 0.25 |
| 47 | 0.009 |
| 48 | 0.01 |
| 49 | 2.7 |
| 50 | 0.83 |
| 51 | 0.10 |
| 52 | 1.0 |
| 53 | 17 |
| 54 | 5.0 |
| 55 | 0.84 |
| 56 | 0.21 |
| 57 | 0.02 |
| 58 | 0.02 |
| 59 | 2.2 |

In Vivo Data

Determination of Effectiveness of Nicotinic Acetylcholine Receptor Ligands as Analgesic Agents in the Mouse Hot Plate Paradigm An in vivo protocol was utilized to determine the effectiveness of nicotinic acetylcholine receptor ligands as analgesic agents in the mouse hot plate paradigm.

Separate groups of mice, (n=8/group) were utilized for each dose group. All drugs were administered by the intraperitoneal route of administration. Test drugs were dissolved in water to make a 6.2 mM stock solution. Animals were dosed with this solution (10 mL/kg body weight) for a 62 micromol/kg dose. Lower doses were administered similarly, following serial dilution of the stock solution in half-log increments. Animals were dosed 30 minutes prior to testing in the hot plate. The hot-plate utilized was an automated analgesia monitor (Model #AHP16AN, Omnitech Electronics, Inc. of Columbus, Ohio). The temperature of the hot plate was maintained at 55° C. and a cut-off time of 180 seconds was utilized. Latency until the tenth jump was recorded as the dependent measure. An increase in the tenth jump latency relative to the control was considered an effect.

Table 2 shows the minimally effective dose (MED), among the doses tested, at which a significant effect, as defined above, was observed for the present compounds. The data shows that selected compounds of the invention show a significant antinociceptive effect at doses ranging from 0.62 to 62 µmol/kg.

TABLE 2

Mouse Hot Plate Data

| Example Number | (MED) µmol/kg |
|---|---|
| 1 | 6.2 |
| 4 | 62 |
| 15 | 0.62 |
| 16 | 6.2 |
| 20 | 62 |
| 22 | 19 |
| 23 | 62 |
| 24 | 6.2 |
| 25 | 19 |
| 27 | 1.9 |
| 30 | 1.9 |
| 31 | 62 |
| 33 | 0.19 |
| 35 | 19 |
| 36 | 1.9 |
| 37 | 6.2 |
| 38 | 19 |
| 39 | 62 |
| 40 | 19 |
| 41 | 6.2 |
| 44 | 0.62 |
| 46 | 6.2 |
| 47 | 6.2 |
| 48 | 6.2 |
| 57 | 1.9 |
| 58 | 0.62 |

Dosage forms for topical administration of a compound of this invention include powders, sprays, ointments and inhalants. The active compound is mixed under sterile conditions with a pharmaceutically acceptable carrier and any needed preservatives, buffers or propellants which can be required. Opthalmic formulations, eye ointments, powders and solutions are also contemplated as being within the scope of this invention.

Actual dosage levels of active ingredients in the pharmaceutical compositions of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required for to achieve the desired therapeutic effect and to gradually increase the dosage until the desired effect is achieved.

When used in the above or other treatments, a therapeutically effective amount of one of the compounds of the present invention can be employed in pure form or, where such forms exist, in pharmaceutically acceptable salt, ester or prodrug form. Alternatively, the compound can be administered as a pharmaceutical composition containing the compound of interest in combination with one or more pharmaceutically acceptable excipients. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal may range from about 0.001 to about 1000 mg/kg/day. For purposes of oral administration, more preferable doses can be in the range of from about 0.001 to about 5 mg/kg/day. If desired, the effective daily dose can be divided into multiple doses for purposes of administration; consequently, single dose compositions may contain such amounts or submultiples thereof to make up the daily dose.

The present invention also provides pharmaceutical compositions that comprise compounds of the present invention formulated together with one or more non-toxic pharmaceutically acceptable carriers. The pharmaceutical compositions can be specially formulated for oral administration in solid or liquid form, for parenteral injection or for rectal administration.

The pharmaceutical compositions of this invention can be administered to humans and other mammals orally, rectally, parenterally, intracistemally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., *Methods in Cell Biology*, Volume XIV, Academic Press, New York, N.Y. (1976), p. 33 et seq.

Compounds of the present invention that are formed by in vivo conversion of a different compound that was administered to a mammal are intended to be included within the scope of the present invention.

The compounds of the invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

The present compounds may have activity against disorders which are mediated through the central nervous system. The following references describe various disorders affected by nicotinic acetylcholine receptors: 1) Williams, M.; Arneric, S. P.: *Beyond the Tobacco Debate: dissecting out the therapeutic potential of nicotine*. Exp. Opin. Invest. Drugs (1996)5(8): 1035-1045; 2) Arneric, S. P.; Sullivan, J. P.; Williams, W.: *Neuronal nicotinic acetylcholine receptors. Novel targets for central nervous system theraputics*. In: Psychopharmacology: The Fourth Generation of Progress. Bloom F E, Kupfer D J (Eds.), Raven Press, New York (1995): 95-109; 3) Arneric, S. P.; Holladay, M. W.; Sullivan, J. P.: *Cholinergic channel modulators as a novel therapeutic strategy for Alzheimer's disease*. Exp. Opin. Invest. Drugs (1996) 5(1): 79-100; 4) Lindstrom, J.: *Nicotinic Acetylcholine Receptors in Health and Disease*. Molecular Neurobiology (1997) 15: 193-222; and 5) Lloyd, G K; Menzaghi, F; Bontempi B; Suto, C; Siegel, R; Akong, M; Stauderman, K; Velicelebi, G; Johnson, E; Harpold, M M; Rao, T S; Sacaan, A I; Chavez-Noriega, L E; Washburn, M S; Vernier, J M; Cosford, N D P; McDonald, L A: *The potential of subtype-selective neuronal nicotinic acetylcholine receptor agonists as therapeutic agents*. Life Sciences (1998)62(17/18): 1601-1606. These disorders include, but are not limited to the following: pain (references 1 and 2), Alzheimer's disease (references 1-5), Parkinson's disease (references 1, 4 and 5), memory dysfunction, Tourette's syndrome (references 1, 2 and 4), sleep disorders (reference 1), attention deficit hyperactivity disorder (references 1 and 3), neurodegeneration, inflammation, neuroprotection (references 2 and 3), amyotrophic atral sclerosis, anxiety (references 1, 2 and 3), depression (reference 2), mania, schizophrenia (references 1, 2 and 4), anorexia and other eating disorders, AIDS-induced dementia, epilepsy (references 1, 2 and 4), urinary incontinence (reference 1), Crohn's disease, migraines, PMS, erectile disfunction, substance abuse, smoking cessation (references 1 and 2) and inflammatory bowel syndrome (references 1 and 4) among others.

The present invention is illustrated by way of the foregoing description and examples. The foregoing description is intended as a non-limiting illustration, since many variations will become apparent to those skilled in the art in view thereof. It is intended that all such variations within the scope and spirit of the appended claims be embraced thereby.

Changes can be made in the composition, operation and arrangement of the method of the present invention described herein without departing from the concept and scope of the invention as defined in the following claims:

We claim:
1. A compound of formula I

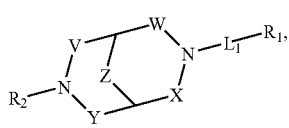

or a pharmaceutically acceptable salt thereof wherein:

V is selected from the group consisting of a covalent bond and $CH_2$;

W is selected from the group consisting of a covalent bond and $CH_2$;

X is selected from the group consisting of a covalent bond and $CH_2$;

Y is selected from the group consisting of a covalent bond and $CH_2$;

Z is $CH_2$;

$L_1$ is selected from the group consisting of a covalent bond and $(CH_2)_n$;

n is 1-5;

$R_1$ is selected from the group consisting of

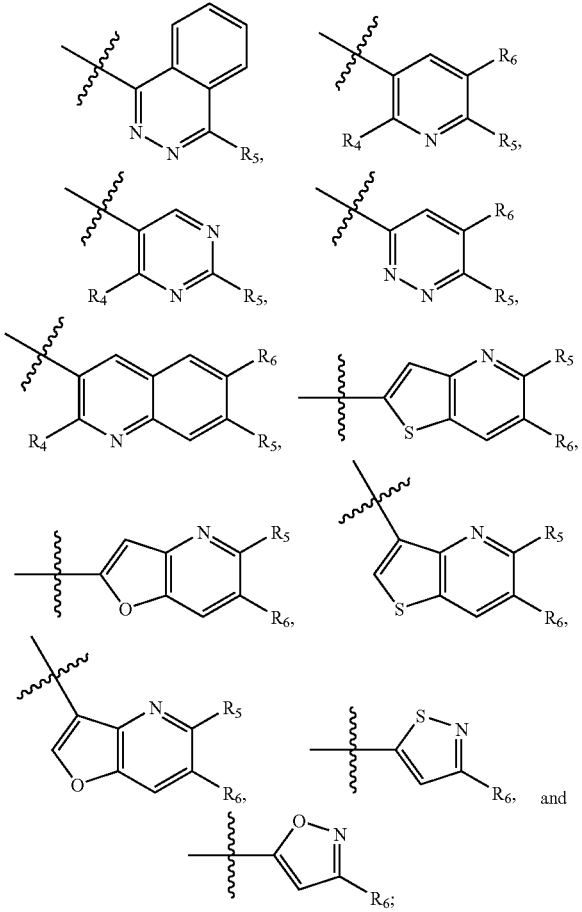

$R_2$ is selected from the group consisting of hydrogen, alkoxycarbonyl, alkyl, aminoalkyl, aminocarbonylalkyl, benzyloxycarbonyl, cyanoalkyl, dihydro-3-pyridinylcarbonyl, hydroxy, hydroxyalkyl, phenoxycarbonyl, and $—NH_2$;

R₄ is selected from the group consisting of hydrogen, alkyl, and halogen;

R₅ is selected from the group consisting of hydrogen, alkoxy, alkyl, halogen, nitro, and —NH₂;

R₆ is selected from the group consisting of hydrogen, alkenyl, alkoxy, alkoxyalkoxy, alkoxyalkyl, alkoxycarbonyl, alkoxycarbonylalkyl, alkyl, alkylcarbonyl, alkylcarbonyloxy, alkylthio, alkynyl, amino, aminoalkyl, aminocarbonyl, aminocarbonylalkyl, aminosulfonyl, carboxy, carboxyalkyl, cyano, cyanoalkyl, formyl, formylalkyl, haloalkoxy, haloalkyl, halogen, hydroxy, hydroxyalkyl, mercapto, mercaptoalkyl, nitro, 5-tetrazolyl, —NR₇SO₂R₈, —C(NR₇)NR₇R₈, —CH₂C(NR₇)NR₇R₈, —C(NOR₇)R₈, —C(NCN)R₇, —C(NNR₇R₈)R₈, —S(O)₂OR₇, and —S(O)₂R₇; and R₇ and R₈ are independently selected from the group consisting of hydrogen and alkyl;

with the proviso that when V is a covalent bond, then X is a covalent bond, W is CH₂ and Y is CH₂, or when V is CH₂, then X is CH₂ W is a covalent bond, and Y is a covalent bond.

2. A compound according to claim 1 of formula II

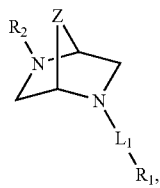

or a pharmaceutically acceptable salt thereof wherein:
Z is CH₂.

3. A compound according to claim 2 selected from the group consisting of:
(1S,4S)-2-(6-chloro-3-pyridazinyl)-2,5-diazabicyclo[2.2.1]heptane;
(1S,4S)-2-(6-chloro-5-methyl-3-pyridazinyl)-2,5-diazabicyclo[2.2.1]heptane;
(1S,4S)-2-(6-chloro-3-pyridazinyl)-5-methyl-2,5-diazabicyclo[2.2.1]heptane;
(1S,4S)-2-(6-chloro-5-methyl-3-pyridazinyl)-5-methyl-2,5-diazabicyclo[2.2.1]heptane;
(1S,4S)-2-(4-chloro-1-phthalazinyl)-2,5-diazabicyclo[2.2.1]heptane;
(1S,4S)-2-(4-chloro-1-phthalazinyl)-5-methyl-2,5-diazabicyclo[2.2.1]heptane;
(1S,4S)-2-(6-chloro-5-methoxycarbonyl-3-pyridazinyl)-2,5-diazabicyclo[2.2.1]heptane;
(1S,4S)-2-(3-pyridazinyl)-2,5-diazabicyclo[2.2.1]heptane;
(1S,4S)-2-(5-pyrimidinyl)-2,5-diazabicyclo[2.2.1]heptane;
(1S,4S)-2-(3-quinolinyl)-2,5-diazabicyclo[2.2.1]heptane;
(1S,4S)-2-(3-methyl-5-isothiazolyl)-2,5-diazabicyclo[2.2.1]heptane;
(1S,4S)-2-(thieno [3,2-b]pyridin-2-yl)-2,5-diazabicyclo[2.2.1]heptane; and
(1S,4S)-2-(furo[3,2-b]pyridin-2-yl)-2,5-diazabicyclo[2.2.1]heptane.

4. A compound according to claim 2 wherein:
Z is CH₂;
L₁ is a covalent bond; and
R₁ is

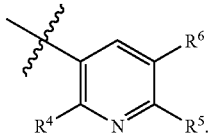

5. A compound according to claim 4 selected from the group consisting of:
(1S,4S)-2-(6-chloro-3-pyridinyl)-2,5-diazabicyclo[2.2.1]heptane;
(1S,4S)-2-(6-amino-3-pyridinyl)-2,5-diazabicyclo[2.2.1]heptane;
(1S,4S)-2-(3-pyridinyl)-2,5-diazabicyclo[2.2.1]heptane;
(1S,4S)-2-[5-hydroxy-3-pyridinyl]-2,5-diazabicyclo[2.2.1]heptane;
(1S,4S)-2-(6-methyl-3-pyridinyl)-2,5-diazabicyclo[2.2.1]heptane;
(1S,4S)-2-(6-nitro-3-pyridinyl)-2,5-diazabicyclo[2.2.1]heptane;
(1S,4S)-2-(6-fluoro-3-pyridinyl)-2,5-diazabicyclo[2.2.1]heptane;
(1S,4S)-2-(5-bromo-3-pyridinyl)-2,5-diazabicyclo[2.2.1]heptane;
(1S,4S)-2-(5-cyano-3-pyridinyl)-2,5-diazabicyclo[2.2.1]heptane;
(1S,4S)-2-(5-aminomethyl-3-pyridinyl)-2,5-diazabicyclo[2.2.1]heptane;
(1S,4S)-2-(5-aminocarbonyl-3-pyridinyl)-2,5-diazabicyclo[2.2.1]heptane;
(1S,4S)-2-(5-methoxy-3-pyridinyl)-2,5-diazabicyclo[2.2.1]heptane;
(1S,4S)-2-(6-chloro-5-hydroxy-3-pyridinyl)-2,5-diazabicyclo[2.2.1]heptane;
(1S,4S)-2-(6-chloro-3-pyridinyl)-5-cyanomethyl-2,5-diazabicyclo[2.2.1]heptane;
(1S,4S)-2-(6-methoxy-3-pyridinyl)-2,5-diazabicyclo[2.2.1]heptane;
(1S,4S)-2-(6-chloro-5-methoxy-3-pyridinyl)-2,5-diazabicyclo[2.2.1]heptane;
(1S,4S)-2-(6-chloro-5-methyl-3-pyridinyl)-2,5-diazabicyclo[2.2.1]heptane;
(1S,4S)-2-(5,6-dichloro-3-pyridinyl)-2,5-diazabicyclo[2.2.1]heptane;
(1S,4S)-2-(6-chloro-5-ethynyl-3-pyridinyl)-2,5-diazabicyclo[2.2.1]heptane;
(1S,4S)-2-(6-chloro-5-cyano-3-pyridinyl)-2,5-diazabicyclo[2.2.1]heptane;
(1S,4S)-2-(6-fluoro-5-methyl-3-pyridinyl)-2,5-diazabicyclo[2.2.1]heptane;
(1S,4S)-2-(5-ethynyl-6-fluoro-3-pyridinyl)-2,5-diazabicyclo[2.2.1]heptane;
(1S,4S)-2-(5-cyano-6-fluoro-3-pyridinyl)-2,5-diazabicyclo[2.2.1]heptane;
(1S,4S)-2-(5-bromo-6-chloro-3-pyridinyl)-2,5-diazabicyclo[2.2.1]heptane;
(1S,4S)-2-(5-hydroxymethyl-6-chloro-3-pyridinyl)-2,5-diazabicyclo[2.2.1]heptane;
(1S,4S)-2-(5-hydroxymethyl-6-fluoro-3-pyridinyl)-2,5-diazabicyclo[2.2.1]heptane;

(1S,4S)-2-(5-hydroxymethyl-3-pyridinyl)-2,5-diazabicyclo[2.2.1]heptane;
(1S,4S)-2-(5-aminomethyl-6-chloro-3-pyridinyl)-2,5-diazabicyclo[2.2.1]heptane;
(1S,4S)-2-(5-aminomethyl-6-fluoro-3-pyridinyl)-2,5-diazabicyclo[2.2.1]heptane;
(1S,4S)-2-(5-aminomethyl-3-pyridinyl)-2,5-diazabicyclo[2.2.1]heptane;
(1S,4S)-2-(5-carboxy-6-chloro-3-pyridinyl)-2,5-diazabicyclo[2.2.1]heptane;
(1S,4S)-2-(5-carboxy-6-fluoro-3-pyridinyl)-2,5-diazabicyclo[2.2.1]heptane;
(1S,4S)-2-(5-carboxy-3-pyridinyl)-2,5-diazabicyclo[2.2.1]heptane;
(1S,4S)-2-(5-aminocarbonyl-6-fluoro-3-pyridinyl)-2,5-diazabicyclo[2.2.1]heptane;
(1S,4S)-2-(5-aminocarbonyl-6-chloro-3-pyridinyl)-2,5-diazabicyclo[2.2.1]heptane;
(1S,4S)-2-(6-chloro-5-hydroxyiminomethyl-3-pyridinyl)-2,5-diazabicyclo[2.2.1]heptane;
(1S,4S)-2-(6-fluoro-5-hydroxyiminomethyl-3-pyridinyl)-2,5-diazabicyclo [2.2.1]heptane;
(1S,4S)-2-(5-hydroxyiminomethyl-3-pyridinyl)-2,5-diazabicyclo[2.2.1]heptane;
(1S,4S)-2-(2-fluoro-3-pyridinyl)-2,5-diazabicyclo[2.2.1]heptane;
(1S,4S)-2-(5-methyl-6-fluoro-3-pyridinyl)-2,5-diazabicyclo[2.2.1]heptane;
(1S,4S)-2-(5-aminosulfonyl-6-fluoro-3-pyridinyl)-2,5-diazabicyclo [2.2.1]heptane;
(1S,4S)-2-(5-aminosulfonyl-6-chloro-3-pyridinyl)-2,5-diazabicyclo[2.2.1]heptane; and
(1S,4S)-2-(5-aminosulfonyl-3-pyridinyl)-2,5-diazabicyclo[2.2.1]heptane.

6. A compound according to claim 1 of formula III

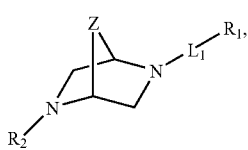

III or a pharmaceutically acceptable salt wherein:
Z is CH$_2$.

7. A compound according to claim 6 selected from the group consisting of:
(1R,4R)-2-(6-chloro-3-pyridazinyl)-2,5-diazabicyclo[2.2.1]heptane;
(1R,4R)-2-(3-pyridazinyl)-2,5-diazabicyclo[2.2.1]heptane;
(1R,4R)-2-(thieno[3,2-b]pyridin-2-yl)-2,5-diazabicyclo[2.2.1]heptane;
(1R,4R)-2-(furo[3,2-b]pyridin-2-yl)-2,5-diazabicyclo[2.2.1]heptane;
(1R,4R)-2-(6-chloro-5-methyl-3-pyridazinyl)-2,5-diazabicyclo[2.2.1]heptane;
(1R,4R)-2-(6-chloro-3-pyridazinyl)-5-methyl-2,5-diazabicyclo[2.2.1]heptane;
(1R,4R)-2-(6-chloro-5-methyl-3-pyridazinyl)-5-methyl-2,5-diazabicyclo[2.2.1]heptane;
(1R,4R)-2-(4-chloro-1-phthalazinyl)-2,5-diazabicyclo[2.2.1]heptane;
(1R,4R)-2-(4-chloro-1-phthalazinyl)-5-methyl-2,5-diazabicyclo[2.2.1]heptane;
(1R,4R)-2-(6-chloro-5-methoxycarbonyl-3-pyridazinyl)-2,5-diazabicyclo[2.2.1]heptane;
(1R,4R)-2-(5 -pyrimidinyl)-2,5-diazabicyclo[2.2.1]heptane;
(1R,4R)-2-(3-quinolinyl)-2,5-diazabicyclo[2.2.1]heptane; and
(1R,4R)-2-(3 -methyl-5-isothiazolyl)-2,5-diazabicyclo[2.2.1]heptane.

8. A compound according to claim 6 wherein:
Z is CH$_2$;
L$_1$ is a covalent bond; and
R$_1$ is

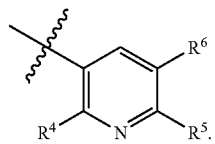

9. A compound according to claim 8 selected from the group consisting of:
(1R,4R)-2-(6-chloro-3-pyridinyl)-2,5-diazabicyclo[2.2.1]heptane;
(1R,4R)-2-(3-pyridinyl)-2,5-diazabicyclo[2.2.1]heptane;
(1R,4R)-2-(6-chloro-3-pyridinyl)-5-cyanomethyl-2,5-diazabicyclo[2.2.1]heptane;
(1R,4R)-2-(6-fluoro-3-pyridinyl)-2,5-diazabicyclo[2.2.1]heptane;
(1R,4R)-2-(5-hydroxy-3-pyridinyl)-2,5-diazabicyclo[2.2.1]heptane;
(1R,4R)-2-(6-chloro-5-hydroxy-3-pyridinyl)-2,5-diazabicyclo[2.2.1]heptane;
(1R,4R)-2-(5-cyano-3-pyridinyl)-2,5-diazabicyclo[2.2.1]heptane;
(1R,4R)-2-(6-methoxy-3-pyridinyl)-2,5-diazabicyclo[2.2.1]heptane;
(1R,4R)-2-(6-chloro-5-methyl-3-pyridinyl)-2,5-diazabicyclo[2.2.1]heptane;
(1R,4R)-2-(5,6-dichloro-3-pyridinyl)-2,5-diazabicyclo[2.2.1]heptane;
(1R,4R)-2-(5-aminocarbonyl-3-pyridinyl)-2,5-diazabicyclo[2.2.1]heptane;
(1R,4R)-2-(6-chloro-5-methoxy-3-pyridinyl)-2,5-diazabicyclo[2.2.1]heptane;
(1R,4R)-2-(5-bromo-3-pyridinyl)-2,5-diazabicyclo[2.2.1]heptane;
(1R,4R)-2-(6-methyl-3-pyridinyl)-2,5-diazabicyclo[2.2.1]heptane;
(1R,4R)-2-(6-nitro-3-pyridinyl)-2,5-diazabicyclo[2.2.1]heptane;
(1R,4R)-2-(6-amino-3-pyridinyl)-2,5-diazabicyclo[2.2.1]heptane;
(1R,4R)-2-(6-chloro-5-ethynyl-3-pyridinyl)-2,5-diazabicyclo[2.2.1]heptane;
(1R,4R)-2-(6-chloro-5-cyano-3-pyridinyl)-2,5-diazabicyclo[2.2.1]heptane;
(1R,4R)-2-(5-ethynyl-6-fluoro-3-pyridinyl)-2,5-diazabicyclo[2.2.1]heptane;
(1R,4R)-2-(5-cyano-6-fluoro-3-pyridinyl)-2,5-diazabicyclo[2.2.1]heptane;
(1R,4R)-2-(5-bromo-6-chloro-3-pyridinyl)-2,5-diazabicyclo[2.2.1]heptane;
(1R,4R)-2-(5-hydroxymethyl-6-chloro-3-pyridinyl)-2,5-diazabicyclo[2.2.1]heptane;

(1R,4R)-2-(5-hydroxymethyl-6-fluoro-3-pyridinyl)-2,5-diazabicyclo[2.2.1]heptane;
(1R,4R)-2-(5-hydroxymethyl-3-pyridinyl)-2,5-diazabicyclo[2.2.1]heptane;
(1R,4R)-2-(5-aminomethyl-6-chloro-3-pyridinyl)-2,5-diazabicyclo[2.2.1]heptane;
(1R,4R)-2-(5-aminomethyl-6-fluoro-3-pyridinyl)-2,5-diazabicyclo[2.2.1]heptane;
(1R,4R)-2-(5-aminomethyl-3-pyridinyl)-2,5-diazabicyclo[2.2.1]heptane;
(1R,4R)-2-(5-carboxy-6-chloro-3-pyridinyl)-2,5-diazabicyclo[2.2.1]heptane;
(1R,4R)-2-(5-carboxy-6-fluoro-3-pyridinyl)-2,5-diazabicyclo[2.2.1]heptane;
(1R,4R)-2-(5-carboxy-3-pyridinyl)-2,5-diazabicyclo[2.2.1]heptane;
(1R,4R)-2-(5-aminocarbonyl-6-fluoro-3-pyridinyl)-2,5-diazabicyclo[2.2.1]heptane;
(1R,4R)-2-(5-aminocarbonyl-6-chloro-3-pyridinyl)-2,5-diazabicyclo[2.2.1]heptane;
(1R,4R)-2-(6-chloro-5-hydroxyiminomethyl-3-pyridinyl)-2,5-diazabicyclo[2.2.1]heptane;
(1R,4R)-2-(6-fluoro-5-hydroxyiminomethyl-3-pyridinyl)-2,5-diazabicyclo[2.2.1]heptane;
(1R,4R)-2-(5-hydroxyiminomethyl-3-pyridinyl)-2,5-diazabicyclo[2.2.1]heptane;
(1R,4R)-2-(2-fluoro-3-pyridinyl)-2,5-diazabicyclo[2.2.1]heptane;
(1R,4R)-2-(5-methyl-6-fluoro-3-pyridinyl)-2,5-diazabicyclo[2.2.1]heptane;
(1R,4R)-2-(5-aminosulfonyl-6-fluoro-3-pyridinyl)-2,5-diazabicyclo[2.2.1]heptane;
(1R,4R)-2-(5-aminosulfonyl-6-chloro-3-pyridinyl)-2,5-diazabicyclo[2.2.1]heptane; and
(1R,4R)-2-(5-aminosulfonyl-3-pyridinyl)-2,5-diazabicyclo[2.2.1]heptane.

10. A compound according to claim 6 wherein:

$Z$ is $CH_2$;

$L_1$ is $(CH_2)n$; and $R_1$ is

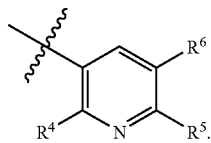

11. A compound according to claim 10 that is (1R,4R)-2-(3-pyridinylmethyl)-2,5-diazabicyclo[2.2.1]heptane.

12. A pharmaceutical composition comprising a therapeutically effective amount of a compound of claim 1 in combination with a pharmaceutically acceptable carrier for treating a disorder selected from the group consisting of pain, Alzheimer's disease, Parkinson's disease, memory dysfunction, Tourette's syndrome, attention deficit hyperactivity disorder, neurodegeneration, neuroprotection, anxiety, depression, schizophrenia, and smoking cessation.

13. A method of treating a disorder in a host mammal in need of such treatment comprising administering a therapeutically effective amount of a compound of claim 1, wherein the disorder is selected from the group consisting of pain, Alzheimer's disease, Parkinson's disease, memory dysfunction, Tourette's syndrome, attention deficit hyperactivity disorder, neurodegeneration, neuroprotection, anxiety, depression, schizophrenia, and, smoking cessation.

14. The method of claim 13 wherein the disorder is pain.

* * * * *